(12) United States Patent
Laux et al.

(10) Patent No.: US 11,512,335 B2
(45) Date of Patent: Nov. 29, 2022

(54) VERTEBRATE CELLS AND METHODS FOR RECOMBINANTLY EXPRESSING A POLYPEPTIDE OF INTEREST

(71) Applicant: Novartis AG, Basel (CH)

(72) Inventors: Holger Laux, Basel (CH); Sandrine Romand, Seyssinet-Pariset (FR); Ursula Bodendorf, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/307,389

(22) PCT Filed: Apr. 29, 2015

(86) PCT No.: PCT/IB2015/053110
§ 371 (c)(1),
(2) Date: Oct. 28, 2016

(87) PCT Pub. No.: WO2015/166427
PCT Pub. Date: Nov. 5, 2015

(65) Prior Publication Data
US 2017/0044587 A1 Feb. 16, 2017

Related U.S. Application Data

(60) Provisional application No. 61/994,310, filed on May 16, 2014, provisional application No. 61/985,589, filed on Apr. 29, 2014.

(51) Int. Cl.
| | | |
|---|---|---|
| *C12P 21/06* | (2006.01) | |
| *C12N 15/63* | (2006.01) | |
| *C12N 5/00* | (2006.01) | |
| *C12P 21/00* | (2006.01) | |
| *C12N 15/90* | (2006.01) | |
| *C12N 9/64* | (2006.01) | |
| *G01N 15/14* | (2006.01) | |
| *A01K 67/00* | (2006.01) | |
| *G01N 15/00* | (2006.01) | |
| *G01N 15/10* | (2006.01) | |

(52) U.S. Cl.
CPC .............. *C12P 21/00* (2013.01); *C12N 5/00* (2013.01); *C12N 9/6424* (2013.01); *C12N 15/907* (2013.01); *C12Y 304/21109* (2013.01); *G01N 15/14* (2013.01); *C12N 2510/02* (2013.01); *G01N 2015/0065* (2013.01); *G01N 2015/1006* (2013.01)

(58) Field of Classification Search
CPC ......... C12P 21/00; C12N 15/907; C12N 5/00; C12N 9/6424; C12N 2510/02; C12Y 304/21109
See application file for complete search history.

(56) References Cited

U.S. PATENT DOCUMENTS

| | | | | |
|---|---|---|---|---|
| 5,648,254 A | * | 7/1997 | Mulvihill ........... | C07K 14/8125 |
| | | | | 435/217 |
| 9,120,853 B2 | * | 9/2015 | Lowman et al. | |
| 9,127,053 B2 | * | 9/2015 | West et al. | |
| 9,365,853 B2 | * | 6/2016 | Richter ................. | A61K 45/06 |
| 10,414,802 B2 | * | 9/2019 | Carfi ...................... | A61K 39/00 |
| 2003/0077739 A1 | | 4/2003 | Simmons et al. | |
| 2007/0059820 A1 | * | 3/2007 | Fang ................... | C07K 16/2863 |
| | | | | 435/320.1 |
| 2010/0287628 A1 | * | 11/2010 | Ostertag ............ | A01K 67/0276 |
| | | | | 800/3 |
| 2014/0086936 A1 | | 3/2014 | Richter et al. | |

FOREIGN PATENT DOCUMENTS

| | | |
|---|---|---|
| JP | 2012-520059 A | 9/2012 |
| WO | 93/13125 A1 | 7/1993 |
| WO | 0208392 A2 | 1/2002 |
| WO | 2009/021754 A2 | 2/2009 |
| WO | 2010096838 A2 | 8/2010 |
| WO | 2012/162828 A1 | 12/2012 |
| WO | 2013/163631 A2 | 10/2013 |
| WO | 2013/192550 A2 | 12/2013 |

OTHER PUBLICATIONS

Sandberg et al. Mapping and partial characterization of proteases expressed by a CHO prodcution cell line. Biotechnology and Boengineering 95:961-971, (Year: 2006).*
Robert et al. Degradation of an Fc-fusion recombinant protein by host cell proteases. Biotechnology and Bioengineering 104:1132-1141, (Year: 2009).*
Dorai et al. Development of mammalian production cell lines expressing CNT0736, a glucagon like peptide-1-MIMETIBODYTM: Factors that influence productivity and product quality. Biotechnology and Bioengineering 103:162-176, (Year: 2009).*
Dorai et al. Characterization of the proteases involved in the N-terminal clipping of Glucagon-like-peptide-1-antibody fusion proteins. AIChE Biotechnol. Prog. 27:220-231, (Year: 2011).*
Zhu J. Mammalian cell protein expression for biopharmaceutical production. Biotechnology Advances 30:1158-1170, (Year: 2012).*
Laux et al. Degradation of recombinant proteins by Chinese hamster ovary host cell proteases is prevented by matriptase-1 knockout. DOI:10.1002/bit.26731, pp. 2530-2540, (Year: 2018).*

(Continued)

*Primary Examiner* — Quang Nguyen
(74) *Attorney, Agent, or Firm* — Nelson Mullins Riley & Scarborough LLP; Jane E. Remillard, Esq.; Christopher L. Frank

(57) ABSTRACT

The present application pertains inter alia to an isolated vertebrate cell suitable for recombinant expression of a polypeptide of interest, wherein the vertebrate cell is altered to impair the function of the endogenous protease matriptase and wherein the cell comprises at least one heterologous polynucleotide encoding a polypeptide of interest and wherein the polypeptide of interest is secreted by the cell. It was found that using respective vertebrate cells for producing a recombinant polypeptide of interest significantly reduces clipping of the polypeptide of interest that is secreted into the cell culture medium. Also provided are improved production and screening methods.

27 Claims, 8 Drawing Sheets

Specification includes a Sequence Listing.

(56) References Cited

OTHER PUBLICATIONS

Lewis et al. Genomic landscapes of Chinese hamster ovary cell lines as revealed by the Cricetulus griseus draft genome. Nature Biotechnology 31:759-765 (with 2 additional pages of Online Methods); (Year: 2013).*

Wurm, F. Cho quasispecies—Implications for manufacturing processes. Processes 1:296-311, (Year: 2013).*

Clark et al. Proteolytic cleavage of human acid-sensing ion channel 1 by the serine protease matriptase. J. Biol. Chem. 285:27130-27143; (Year: 2010).*

Jee Yon Kim et al: "CHO cells in biotechnology for production of recombinant proteins: current state and further potential" Applied Microbiology and Biotechnology, Springer, Berlin, DE, vol. 93, No. 3, Dec. 9, 2011 (Dec. 9, 2011), pp. 917-930, XP035006081,ISSN: 1432-0614, DOI: 10.1007/S00253-011-3758-5.

D. Qiu et al: "Roles and regulation of membrane-associated serine proteases: Figure 1". Biochemical Society Transactions, vol. 35, No. 3, Jun. 1, 2007 (Jun. 1, 2007), pp. 583-587, XP055222770, GB. ISSN: 0300-5127, DOI:10.1042/BST0350583.

List K. et al., Matriptase/MT-SP1 is required for postnatal survival, epidermal barrier function, hair follicle development, and thymic homeostasis, Oncogene, 2002, V. 21, N. 23, p. 3765-3779, p. 3766-3767.

List K. et al., Loss of proteolytically processed filaggrin caused by epidermal deletion of Matriptase/MT-SP1, The Journal of cell biology, 2003, V. 163, N. 4, p. 901-910, c.903-905.

Korot'Ko G. F., Digestive system proteinase-activated receptor,Medical messenger of the south of Russia, 2012, No. 1, p. 23-27.

Yamasaki et al., "Inhibition of Membrane-Type Serine Protease 1/Matriptase by Natural and Synthetic Protease Inhibitors", J Nutr Sci Vitaminol, (2003) 49:27-32.

Analysis of Clipping in CHO-K1 Cells, 5 pages (cited in Opposition of EP Patent 3137595 on Dec. 21, 2020).

Antibody Purification Handbook (2007) Pub: GE Healthcare, 167 pages (cited in Opposition of EP Patent 3137595 on Dec. 11, 2019).

Baycin-Hizal et al., "Proteomic Analysis of Chinese Hamster Ovary Cells", J Proteome Res, vol. 11(11): 5265-5276 (2012) DOI: 10.1021/pr300476w.

Beliveau, F. et al., "Probing the substrate specificities of matriptase, matriptase-2, hepsin and DESC1 with internally quenched fluorescent peptides," FEBS Journal, vol. 276: 2213-2226 (2009) DOI: http://dx.doi.org/10.1111/i.1742-4658.2009.06950.x.

Caliper analysis of antibody-like molecule comprising matriptase linker, 10 pages (cited in Opposition of EP Patent 3137595 on Nov. 13, 2020).

Chen et al., "The Transmembrane Serine Protease Matriptase: Implications for Cellular Biology and Human Diseases," J Med Sci, vol. 32:97-108 (2012).

Clark, E. et.al., "Proteolytic Cleavage of Human Acid-sensing Ion Channel 1 by the Serine Protease Matriptase," The Journal of Biological Chemistry, vol. 285(35): 27130-27143 (2010).

Declaration I concerning caliper analysis of antibody-like molecule comprising matriptase linker, 14 pages (cited in Opposition of EP Patent 3137595 on Nov. 13, 2020).

Declaration II concerning caliper analysis of antibody-like molecule comprising matriptase linker, 14 pages (cited in Opposition of EP Patent 3137595 on Nov. 13, 2020).

Declaration III concerning Analysis of Clipping in CHO-K1 Cells, 9 pages (cited in Opposition of EP Patent 3137595 on Dec. 21, 2020).

Declaration of Dr. Paul Wassmann and Annex thereto, 11 pages (cited in Opposition of EP Patent 3137595 on May 19, 2021).

Declaration of Dr. Thomas Jostock and Annex thereto, 16 pages (cited in Opposition of EP Patent 3137595 on May 19, 2021).

Declaration of Dr. Ursula Bodendorf and Annex thereto, 5 pages (cited in Opposition of EP Patent 3137595 on May 19, 2021).

Desnoyers, L. et al., "Tumor-Specific Activation of an EGFR-Targeting Probody Enhances Therapeutic Index," ScienceTranslationalMedicine, vol. 5 Issue 7 (2013).

Excel Table containing the supplementary data to D16 downloaded Feb. 5, 2020 https://www.ncbi.nlm.nih.gov/pmc/articles/PMC3772721#!po=70.6897, 1391 pages (cited in Opposition of EP Patent 3137595 on Jul. 17, 2020).

Gamper et al., "The use of Chinese hamster ovary (CHO) cells in the study of ion channels", Journal of Pharmacological and Toxicological Methods, (20050000), vol. 51, pp. 177-185, XP004873791 DOI: http://dx.doi.org/10.1016/j.vascn.2004.08.008.

Laux et al. 2018 Biotechnology and Bioengineering 115:2530-2540.

Invitrogen transfection protocol for Calu-3 cells, 3 pages (cited in Opposition of EP Patent 3137595 on Dec. 11, 2019).

Meltzer et al., The Journal of Biological Chemistry,vol. 282 No. 35, p. 25548-25559, 2007.

Najy, A. et al., "Differential Tumorigenic Potential and Matriptase Activation between PDGF B versus PDGF D in Prostate Cancer," Mol Cancer Res, vol. 10(8):1087-1097 (2012) DOI: http://dx.doi.org/10.1158/1541-7786. MCR-12-0071.

Suppressor of tumorigenicity protein 14 [Cricetulus griseus] protein, (Aug. 25, 2011), Database accession No. EGV92965, 2 pages.

Netzel-Arnett et al., "Membrane anchored serine proteases: A rapidly expanding group of cell surf ace proteolytic enzymes with potential roles in cancer", Cancer and Metastasis Reviews, (20030000), vol. 22, pp. 237-258.

New experimental data showing that impairment of matriptase does not reduce clipping of a polypeptide of interest, 17 pages (cited in Opposition of EP Patent 3137595 on Jul. 7, 2021).

Nimishakavi, S. et al., "Activity and inhibition of prostasin and matriptase on apical and basolateral surfaces of human airway epithelial cells," Am J Physiol Lung Cell Mol Physiol., vol. 303: L97-L106 (2012).

Ong, H., et al., "Pharmaceutical applications of the Calu-3 lung epithelia cell line," Expert Opinion on Drug Delivery, vol. 10 (9): (2013).

PhD thesis Sine Godiksen—Towards an understanding of the Role of Matriptase in Normal Physiology; Department of Biology, University of Copenhagen; submitted Sep. 17, 2012, 108 pages.

Redacted declaration by the Opponent's scientists in response to declarations D36 and D37 by the patentee's scientists, 21 pages (cited in Opposition of EP Patent 3137595 on Jul. 7, 2021).

Redacted declaration by the scientist who carried out the experiments in D41, 9 pages (cited in Opposition of EP Patent 3137595 on Jul. 7, 2021).

Supplementary Table 2 of D16, Also available on line at: https://pubs acs .org/doi/10 1021 /pr300476w, 17 pages (cited in Opposition of EP Patent 3137595 on Jul. 17, 2020).

Tans, C. et al., "Evaluation of the Proteolytic Activity Present in Cho Cell Culture Supernatants," Animal Cell Technology, 295-300 (1997).

Warner, T. et al.,"Enhancing therapeutic glycoprotein production in Chinese hamster ovary cells by metabolic engineering endogenous gene control with antisense DNA and gene targeting," Glycobiology, vol. 9(9): 841-850 (1999).

Welman, A. et al., "Diversity of Matriptase Expression Level and Function in Breast Cancer," PLOS ONE, vol. 7 (4):e34182 (2012).

Ong, H. et al., "Pharmaceutical applications of the Calu-3 lung epithelia cell line," Expert Opin. Drug Deliv., vol. 10(9): 1287-1302 (2013).

Wurm and Hacker, "First CHO genome," Nat. Biotech, vol. 29(8): 718-720 (2011).

Declaration of Professor Christopher Mark Smales, filed in EP Opposition EP3137595, dated Dec. 20, 2021, 22 pages.

Declaration of Professor Ray Owens, filed in EP Opposition EP3137595, dated Dec. 19, 2021, 9 pages.

Written Submissions in Direct Response to the Preliminary Opinion of the Opposition Division ("OD") provided with the Summons to attend Oral Proceedings filed in EP Opposition EP 3137595, Notice date Jan. 14, 2021, 12 pages.

Frenzel, A. et al., "Expression of recombinant antibodies," Frontiers in Immunology, vol. 4 (Article 217): pp. 1-20 (2013).

(56) References Cited

OTHER PUBLICATIONS

Roche Applied Science, "The complete Guide for Protease Inhibition," pp. 1-16 (2004) (XP055657663) Roche Diagnostics GmbH.

* cited by examiner

Fig. 2

*tttttgcccagtcctgtt*ctcctccaaactcacagtgtcactgaacctccgggctgggaagctatgtgtcggggagcgtctctgagtcctgaaa
tatcttctgtttagaacatgaatgagttttctgcctgttgaataatgccaagaaagtggagaagtggagaggcccccggcg
ctgtggtgctgctgttgtgctgcagttcctgcctcactgtgttcctctccttcctctgcactgtggcacttcctctgtgtacagtgggg
gctgtggagggcgacagagggtagtgttctctctctctc*tcagaggacagaccaaaggg*

Fig. 3

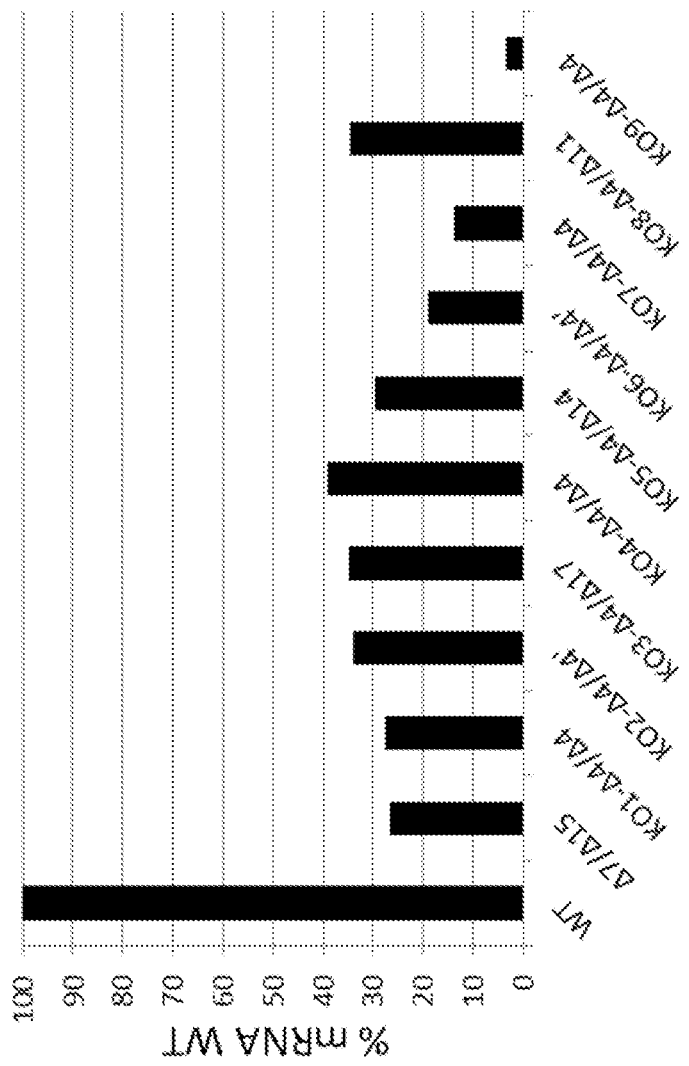

VERTEBRATE CELLS AND METHODS FOR RECOMBINANTLY EXPRESSING A POLYPEPTIDE OF INTEREST

FIELD OF THE DISCLOSURE

The present disclosure concerns the field of recombinant expression technologies. It inter alia pertains to altered vertebrate cells and their use in recombinant expression methods. When recombinantly expressing a polypeptide of interest in said altered cells which is then secreted into the cell culture medium, clipping of the recombinantly expressed polypeptide of interest in the cell culture medium is significantly reduced or even completely prevented.

BACKGROUND OF THE DISCLOSURE

The market for biopharmaceuticals continues to grow at a high rate as biopharmaceuticals become more and more important for today's medicine. Currently, an increasing number of biopharmaceuticals is produced in vertebrate cells such as in particular mammalian cells. Biopharmaceuticals include but are not limited to antibodies, antibody fragments, ADCs (antibody drug conjugate), nanobodies, Fc-fusion proteins, growth factors, hormones, cytokines, enzymes and other therapeutic polypeptides. Especially expression of recombinant non-antibody therapeutic proteins is of increasing importance. Furthermore, the recombinant expression of polypeptides in mammalian cells is also for other fields of use of high interest. Considering the production costs for recombinantly expressed polypeptides, it is important to have high expressing mammalian cell lines. The polypeptide of interest is expressed and secreted by the mammalian cells into the cell culture medium from which it is then harvested.

One major problem that is encountered when using vertebrate cells such as mammalian cells as host cells for recombinant expression is the proteolytic degradation of the expressed and secreted polypeptide of interest in the cell culture medium, also referred to as "clipping". Proteases originating from the vertebrate cells used for production are active in the cell culture medium whose proteolytic activity may degrade the recombinantly expressed and secreted polypeptide of interest, thereby rendering an altered, e.g. non- or less functional polypeptide of interest. This host cell related proteolytic degradation is one of the major hurdles in the recombinant expression of polypeptides. Even though IgG antibodies may also be affected, e.g. because IgG antibodies may be clipped in the variable regions, proteolytic degradation, i.e. clipping, occurs at a much higher frequency with non-IgG polypeptides. Such non-IgG polypeptides, in particular glycopolypeptides, due to their relatively exposed three-dimensional structure, can be very sensitive to proteolytic degradation. Clipping of recombinantly expressed non-IgG polypetides can reach values up to 100%. Clipping can lead to inactive and/or immunogenic polypeptides which are not useful for the intended purpose. Furthermore, even if proteolytic degradation only occurs to a certain percentage, the clipped polypeptide cannot be used for the intended purpose and therefore reduces the yield of useful recombinant polypeptide of interest. Additionally, for many applications the clipped polypeptide has to be removed during purification. This may require the specific development of purifications methods that allow separating the clipped from the intact polypeptide, which can be labor and cost intensive and sometimes are even not successful so that clipped protein remains as impurity. Therefore, proteolytic degradation of the expressed polypeptide of interest in the cell culture medium is a major issue when recombinantly producing a polypeptide of interest in vertebrate cells.

Several studies have investigated the phenomenon of clipping in order to provide solutions to this problem. Clipping was found to be time and temperature dependent and could be inactivated by heat treatment. However, so far little is known about the proteases expressed by the vertebrate host cells used for recombinant expression, and about the proteases responsible for clipping. One of the major challenges is the number of proteases expressed by vertebrate host cells. E.g. more than 700 proteases are known to be present in rodent cell genomes, many of which could be involved in clipping.

Several approaches were suggested in the prior art to overcome the problems of clipping. One approach to avoid clipping is the reengineering of the affected protein in order to eliminate amino acid motifs that are prone to clipping. However, this approach is time consuming, needs extensive testing whether the chosen approach was successful and does not guarantee that the reengineered protein is still functional, does not show clipping at other sites and is not immunogenic. A different way to control protease activity in the cell culture is to add inhibitors or substitute substrates into the culture medium. However, in large-scale manufacturing processes such additives are expensive and have to be removed during purification which may require specific development of purification methods and sensitive assays to monitor that no additives remain. Other ways to reduce proteolytic degradation of the expressed polypeptide of interest in the cell culture medium include timing of the harvest (early harvest) to limit the exposure of the polypeptides of interest to proteases in the cell culture medium, reducing the temperature of the culture, optimizing the pH conditions or improving the cell viability to reduce the release of intracellular proteases into the cell culture medium. Furthermore, it was found that the choice of the vertebrate cell line used as production host cell may have an influence on clipping depending on the proteases that are expressed by the respective cell line and the individual polypeptide of interest to be expressed. Therefore, one option is to screen different cell lines to identify a cell line wherein clipping of the polypeptide of interest does not occur or occurs to a lesser extent, which, however, is time-consuming and may require the adaptation of the production process to the chosen cell line. Even though these different options can reduce clipping, they will rarely completely eliminate the proteolytic degradation. Furthermore, in many cases adaptations of the expression and production process to the individual polypeptide of interest to be expressed is required in order to develop a production method that avoids or at least reduces the problems of clipping and provides the intact polypeptide of interest with sufficient yield and purity. Such adaptations are, however, time consuming and costly. Therefore, improved ways are needed to address the problem of clipping.

Therefore, is an object of the invention to provide an improved method for the recombinant production of a polypeptide of interest in vertebrate cells wherein clipping of the expressed and secreted polypeptide of interest in the cell culture medium is reduced or eliminated. In particular, it is an object of the present invention to provide novel vertebrate cells, wherein clipping of a polypeptide of interest expressed and secreted by said cells is reduced or eliminated.

SUMMARY OF THE DISCLOSURE

The present disclosure is inter alia based on the unexpected finding that altering a vertebrate cell to impair the effect of the endogenous protease matriptase, e.g. by reducing or eliminating the functional expression of the matriptase gene, significantly decreases the proteolytic degradation ("clipping") of a recombinant polypeptide of interest that is expressed and secreted by said cell into the cell culture medium. Thus, impairing the effect of matriptase in said cell reduces clipping of the secreted recombinant polypeptide of interest compared to a corresponding vertebrate cell in which the effect of matriptase is not impaired. With matriptase, a key protease responsible for clipping of recombinantly expressed and secreted polypeptides was identified. Altering the vertebrate cell to impair the effect of matriptase allows to significantly improve the recombinant production of a polypeptide of interest by reducing or eliminating clipping of the recombinantly expressed and secreted polypeptide of interest in the cell culture medium. Thereby, the yield of intact polypeptide of interest is increased. As it is demonstrated by the examples, these advantageous effects are not seen when impairing the function of other proteases which confirms that matriptase is the major protease responsible for clipping. The novel vertebrate cells provided by the present disclosure obviate the need to reengineer the polypeptide of interest to be expressed in order to eliminate proteolytic sites or to laboriously adapt the production process to reduce or prevent clipping or to design specific purification processes to remove clipped protein. Advantageously, these altered vertebrate cells described herein can be used as universal host cells for expressing different polypeptides of interest, including polypeptides of interest that are particularly prone to clipping. Specific adaptations of the polypeptide to be expressed or the expression system become obsolete, which saves time and costs. Furthermore, as is demonstrated by the examples, the altered vertebrate cell provided by the present disclosure show good growth and expression characteristics. Therefore, impairing the effect of matriptase still provides host cells with favorable expression characteristics that are important for the recombinant expression of a polypeptide of interest. Hence, the present invention makes an important contribution to the prior art.

According to a first aspect, the present disclosure provides an isolated vertebrate cell suitable for recombinant expression of a polypeptide of interest, wherein the vertebrate cell is altered to impair the effect of matriptase and comprises at least one heterologous polynucleotide encoding a polypeptide of interest, wherein the vertebrate cell secretes the polypeptide of interest. The vertebrate cell is altered to impair the effect of matriptase e.g. by reducing or eliminating functional expression of the matriptase gene in said vertebrate cell, e.g. by gene silencing, gene deletion or by mutating the matriptase gene so that a non- or less functional protein is expressed. Impairing the effect of matriptase in the vertebrate cell reduces clipping of the secreted recombinant polypeptide of interest compared to a corresponding vertebrate cell in which the effect of matriptase is not impaired. As is shown by the examples inter alia based on spike-in experiments, in the supernatant of the cell culture medium that is obtained when culturing respectively altered vertebrate cells in which the effect of matriptase is impaired, clipping of recombinant polypeptides of interest is surprisingly highly reduced even though other proteases are still active in the supernatant. These results were confirmed by expressing several polypeptides of interest in respectively altered cells wherein the effect of matriptase is impaired. These results confirm that matriptase is a key protease responsible for clipping of a recombinantly expressed and secreted polypeptide of interest. Thus, the vertebrate cells according to the first aspect are particularly suitable as host cells for recombinant production technologies and can be used for recombinant production of a polypeptide of interest that is secreted by the vertebrate cell into the cell culture medium from which it can then be harvested.

According to a second aspect, the present disclosure provides a method for producing a vertebrate cell according to the first aspect, comprising altering a vertebrate cell to impair the effect of matriptase and introducing a polynucleotide encoding a polypeptide of interest to be expressed, wherein said polypeptide of interest is secreted by the vertebrate cell. Impairment of the effect can be achieved e.g. by reducing or eliminating functional expression of the matriptase gene in said cell, e.g. by gene silencing, gene deletion or by mutating the matriptase gene so that a non- or less functional protein is expressed.

According to a third aspect, a method is provided for recombinantly producing a polypeptide of interest, comprising utilizing a vertebrate cell according to the first aspect as host cell for recombinant expression of the polypeptide of interest. As described above, due to the achieved reduced level of polypeptide clipping in the cell culture medium, these altered vertebrate cells are particularly suitable as host cells for recombinant production of a polypeptide of interest, in particular of polypeptides that are prone to clipping such as glycopolypeptides. As preferred embodiment, a method for recombinantly producing a polypeptide of interest is provided, comprising (a) culturing vertebrate host cells according to the first aspect under conditions that allow for the expression and secretion of the polypeptide of interest into the cell culture medium;

(b) isolating the polypeptide of interest from the cell culture medium; and (c) optionally processing the isolated polypeptide of interest.

According to a fourth aspect, a method for recombinantly producing a polypeptide of interest is provided, comprising (a) culturing vertebrate host cells which comprise at least one heterologous polynucleotide encoding a polypeptide of interest under conditions that allow for the expression and secretion of the polypeptide of interest into the cell culture medium, wherein the cell culture medium comprises a protease inhibitor that is selective for matriptase;

(b) isolating the polypeptide of interest from the cell culture medium; and (c) optionally processing the isolated polypeptide of interest.

According to a fifth aspect, a method is provided for selecting a host cell which recombinantly expresses a polypeptide of interest, comprising (a) providing vertebrate cells according to the first aspect as host cells; and (b) selecting one or more host cells expressing the polypeptide of interest.

According to a sixth aspect, the present disclosure pertains to the use of a vertebrate cell for recombinant production of a polypeptide of interest that is secreted from the vertebrate cell, wherein the used cell is altered to impair the effect of the endogenous protease matriptase. Respectively altered cells can be e.g. transfected with a polynucleotide encoding a polypeptide of interest that is supposed to be expressed and secreted by said cell. When using respective vertebrate cells wherein the effect of the endogenous protease matriptase is impaired, no or reduced amounts of functional matriptase are active in the cell culture medium. This significantly reduces or even eliminates proteolytic degradation of the recombinant polypeptide of interest that is secreted by the cells into the cell culture medium. Therefore, it is advantageous to use such altered vertebrate cell for recombinant protein expression.

According to a seventh aspect, the present disclosure pertains to a method for selecting a vertebrate cell for recombinant production of a polypeptide of interest, comprising analyzing if the endogenous protease matriptase is functionally expressed in the vertebrate cell and selecting a vertebrate cell in which the effect of such endogenous matriptase is impaired for recombinant production of the polypeptide of interest. This selection process allows identifying vertebrate cells that are capable of producing a recombinant polypeptide of interest, wherein clipping of the polypeptide of interest in the cell culture medium is reduced. Respective vertebrate cells are particularly suitable for recombinant protein production.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

BRIEF DESCRIPTION OF THE FIGURES

FIG. 2 shows SEQ ID NO: 31, which is the sequence of exon 2 of the matriptase gene plus flanking intron regions in CHO-K1 derived cells. Sequencing primers (cursive, bold and underlined) were designed to target flanking introns to confirm CHO-K1-derived MT-SP1 exon 2 sequence (shaded in grey). Binding sites of DNA binding domains of TALENs used to obtain matriptase knock-out cells are depicted in bold and underlined and the target region for knock-out mutation is shown in bold and double-underlined.

FIG. 3 shows a column diagram representing the relative matriptase mRNA expression measured in the CHO-K1 derived matriptase knock-out cell clones KO-1 to KO-9 and clone Δ7/Δ15 and a CHO-K1 derived wildtype cell line (WT). The matriptase mRNA expression in the wildtype CHO-K1 derived cell line was defined as 100%. As can be seen, matriptase mRNA expression was reduced in all knock-out clones and clone Δ7/Δ15.

FIG. 4D shows the result of a repetition of the experiment with the mAb using conditioned medium obtained from respective cells that had been cultivated for three month. The incubation conditions were identical as in FIG. 4A. The results demonstrate that clipping is efficiently prevented in the conditioned medium obtained from the matriptase knock-out cell clones KO-1 to KO-9 and that these advantageous results are maintained during prolonged culturing.

FIG. 7A shows a Western Blot analysis of mAb (incubation time 24 h), FIG. 7B a capillary gel electrophoresis analysis (Caliper LabChip®) of an Fc-fusion protein (incubation time 2 h) and FIG. 7C a Western Blot analysis of a further recombinant protein (incubation time 1 h). The concentration of the polypeptide of interest was 0.7 μM in all experimental set ups. Each polypeptide of interest was tested with decreasing amounts of the MT-SP1 and Htra1: Molar ratios of protease to polypeptide of interest from left to right are $1/10$, $1/100$ and $1/1000$ for MT-SP1 and $1/3$, $1/10$ and $1/100$ for Htra1. The polypeptides of interest were also incubated for the same time in a chemically defined culture medium "(+)" and in conditioned medium (supernatant) obtained from CHO-K1 derived wildtype cells "(−)". The intact proteins (larger) and the clipped proteins (smaller) are indicated by the arrows in FIGS. 7A and 7C. In FIG. 7B, there are two types of clipped polypeptides beside the intact polypeptide (all marked with an arrow and illustrated at the side). FIG. 7A to FIG. 7C demonstrates that clipping occurs in the presence of matriptase, thereby confirming that matriptase is a key protease responsible for clipping.

DETAILED DESCRIPTION

Figure 1:
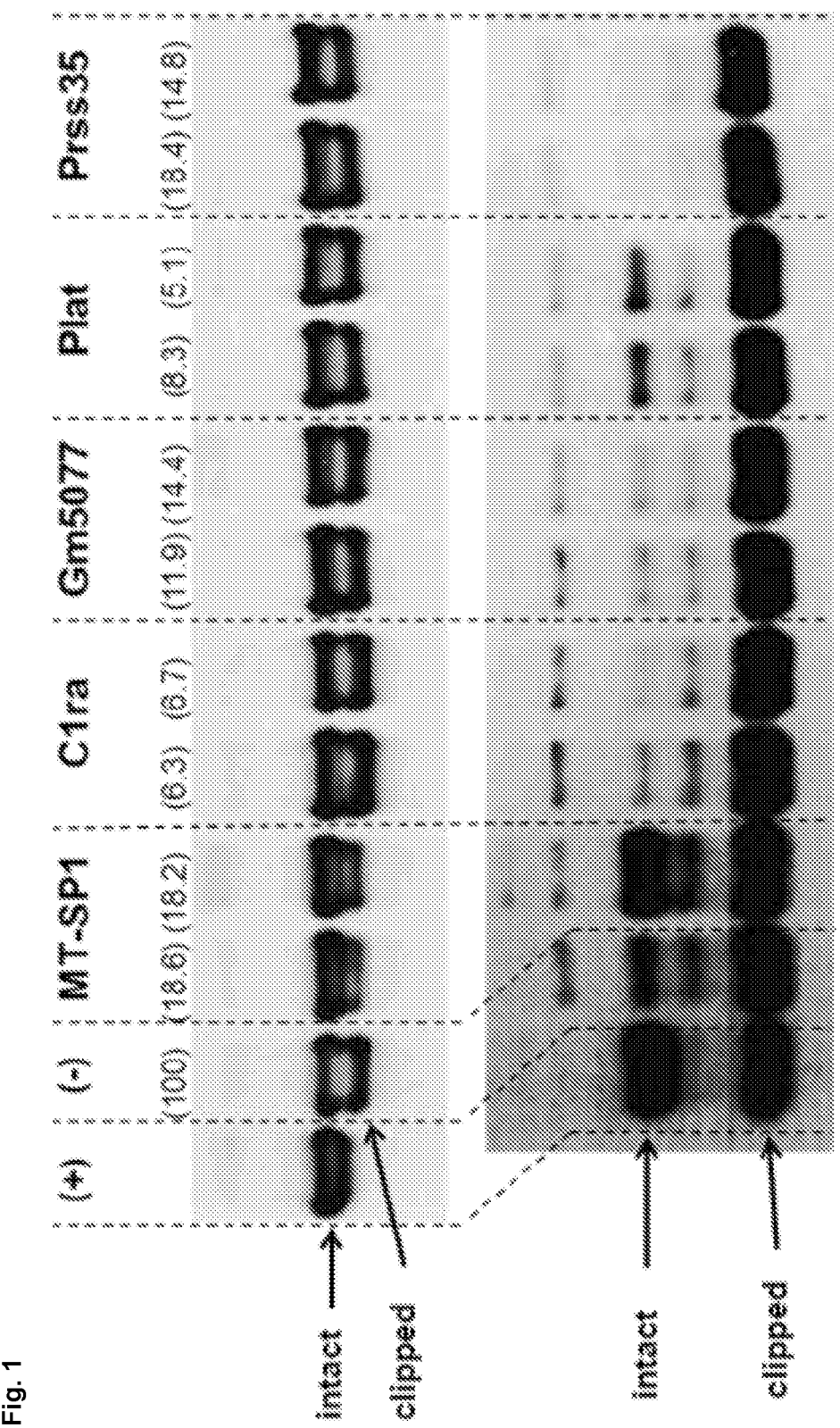
FIG. 1 shows a Western Blot for two therapeutic proteins (upper panel: IgG (mAb), lower panel: Fc-fusion protein) incubated for several days in conditioned medium obtained by cultivating CHO cells transfected with siRNAs directed against different protease target genes (7 days incubation for mAb, 3 days incubation for the Fc-fusion protein). The first control "(+)" represents a sample of the polypeptide of interest incubated for the same time in a chemically defined culture medium which was not in contact with cells. The chemically defined culture medium used as control was the same culture medium as the culture medium in which the cells were cultured to obtain the conditioned medium. The second control "(−)" represents a sample of the polypeptide of interest incubated in the conditioned medium obtained from CHO cells transfected with a non-effective siRNA (125 pmol) which served as siRNA negative control. The names of the target trypsin-like serine proteases and homologs whose expression were silenced by siRNA transfection are given above the upper panel (MT-SP1 (matriptase, also referred to herein as St14), C1r (also referred to as C1ra), C1s (also referred to as Gm5077), Plat, and Prss35). For each of the combinations "polypeptide of interest/conditioned medium of cells with silenced protease expression" results of two experimental set ups with different siRNA concentrations are shown. Also determined and indicated in FIG. 1 below in parenthesis is the percentage of residual protease gene-expression in relation to the protease gene-expression in the siRNA negative control cells which was set as 100%. This means e.g. with respect to MT-SP1 (18.6%) that there was 18.6% residual gene-expression upon silencing. MT-SP1: 125 pmol (18.6%) and 150 pmol (18.2%), C1r (C1ra): 125 pmol (6.3%) and 150 pmol (6.7%), C1s (Gm5077): 100 pmol (11.9%) and 125 pmol (14.4%), Plat: 125 pmol (8.3%) and 150 pmol (5.1%) and Prss35: 100 pmol (18.4%) and 125 pmol (14.8%). The results demonstrate that when the MT-SP1 mRNA level is down-regulated by RNA interference, significantly less clipping occurred in the conditioned medium (detected for mAb and Fc-fusion protein). When other expressed trypsin-like serine proteases were down-regulated, clipping remains the same. The results thus demonstrate that matriptase is the key protease responsible for clipping.

The present disclosure is inter alia based on the unexpected finding that an altered vertebrate cell, in which the effect of the endogenous protease matriptase is impaired, e.g. by reducing or eliminating functional expression of the matriptase gene, is capable of expressing and secreting a recombinant polypeptide of interest into the cell culture medium, wherein, however, clipping of the recombinant polypeptide of interest in the cell culture medium is significantly reduced. Thus, the major protease responsible for clipping of recombinantly expressed and secreted polypeptides was identified among hundreds of different proteases. It was also highly surprising that targeting and impairing the activity of a single protease is sufficient to significantly reduce or even eliminate clipping in the cell culture medium. Using e.g. respectively altered vertebrate cells according to the invention allows to significantly improve the recombinant production of a polypeptide of interest by increasing the yield of intact polypeptide of interest that can be obtained after expression and secretion from the cell culture medium. Therefore, when using the altered vertebrate cell according to the invention for recombinantly producing a polypeptide of interest, it is not necessary to perform additional measures to reduce proteolytic degradation and hence prevent clipping of the polypeptide of interest. Therefore, the present invention makes an important contribution to the prior art.

The individual aspects and suitable and preferred embodiments of the present disclosure will now be described in detail.

A. Altered Vertebrate Cells

According to a first aspect, the present disclosure provides an isolated vertebrate cell suitable for recombinant expression of a polypeptide of interest, wherein the vertebrate cell is altered to impair the effect of matriptase and comprises at least one heterologous polynucleotide encoding a polypeptide of interest, wherein the vertebrate cell secretes the polypeptide of interest. Impairing the effect of matriptase in the vertebrate cell reduces clipping of the secreted recombinant polypeptide of interest compared to a corresponding vertebrate cell in which the effect of matriptase is not impaired.

Matriptase, was first described in 1993 as a new gelatinolytic activity in cultured breast cancer cells. Matriptase belongs to the family of type II transmembrane serine proteases (TTSPs). Orthologs of matriptase are present in different vertebrate species, including mammalian species, and were identified for example in human, chimpanzee, dog, mouse, rat, chicken, zebrafish, spotted green putterfish and tiger putterfish which suggests a conserved evolutionary function. Matriptase is listed in the IUBMB Enzyme nomenclature as EC 3.4.21.109. Matriptase is also known as membrane-type serine protease 1 (MT-SP1) and suppressor of tumorigenicity-14 (ST14) (see Chen et al, The Transmembrane Serine Protease Matriptase: Implications for Cellular Biology and Human Diseases J Med Sci 2012; 32 (3): 097-108). It is an integral membrane protein with a singlespan transmembrane domain close to the cytoplasmatic N-Terminus. The extracellular part consists of a stem region (including a single SEA, 2 CUB and 4 LDLRA domains) and the C-terminal serine protease domain that is structurally highly similar to other TTSPs and includes a conserved histidine/aspartic acid/serine (HDS) catalytic triad essential for catalytic activity (see e.g. List et al, Matriptase: Potent Proteolysis on the cell Surface; MOL MED 12 (1-3) 1-7, JANUARY-MARCH 2006 and Chen et al, The Transmembrane Serine Protease Matriptase: Implications for Cellular Biology and Human Diseases J Med Sci 2012; 32 (3): 097-108). Matriptase is described as being expressed in the epithelia in many organ systems such as skin, breast, lung, epidermis, cornea, salivary gland, oral and nasal cavities, thyroid, thymus, esophagus, trachea, bronchioles, alveoli, stomach, pancreas, gallbladder, duodenum, small intestine, colon, rectum, kidney, adrenals, urinary bladder, ureter, seminal vesicles, epididymis, prostate, ovaries, uterus and vagina (see List et al, 2006 and Chen et al, 2012). Matriptase is synthesized as an inactive zymogen and is converted to its active form via a complicated process. Details regarding the activation process which involves endoproteolytic cleavages are described for the human matriptase in List et al 2006 and Chen et al 2012. Matriptase is bound to the membrane as type II transmembrane protein with the catalytic domain orientated into the extracellular space. Furthermore, it is described in the literature that a significant shedding of matriptase, respectively its extracellular part, occurs in vivo (see List et al, 2006 and Chen et al 2012). It is described in the literature that matriptase is shed in form of a complex, e.g. complexed to the Kunitz-type serine protease inhibitor HAI-1. Different studies suggest that in human cells the specific inhibitor HAI-1 facilitates the transport of the matriptase to the cell membrane as it was shown that removal or even single point mutations in HAI-1 lead to an accumulation of the matriptase in the Golgi compartment. In the literature, several different endogenous inhibitors of matriptase besides HAI-1 have been described such as HAI-2, antithrombin, alpha-1 antitrypsin and alpha-2-antiplasmin. Furthermore, also other inhibitors of matriptase have been described (see e.g. Chen et al, 2012). It is described in the literature that matriptase may play numerous roles in normal physiology such as skin barrier function, epithelial integrity, hair follicle development, and thymus homeostasis, and in human pathologies, such as osteoarthritis, atheroscleorisis, and tumor progression, invasion, and metastasis.

Against this scientific background which is unrelated to the recombinant production of a polypeptide of interest, the present finding that matriptase is a key protease responsible for clipping of recombinantly produced polypeptides of interest that are secreted by the host cells into the cell culture medium was highly surprising. Considering the large number and variety of proteases expressed in vertebrate cells, such as in particular mammalian cells, it was even more surprising that impairing the function of this single protease—matriptase—is sufficient to significantly reduce or even eliminate clipping of the secreted polypeptide of interest in the cell culture medium. These advantageous effects are not seen with other, even closely related proteases what supports the importance of the finding that matriptase is the key enzyme responsible for clipping of secreted recombinant polypeptides in the cell culture medium. As is shown by the examples, when using altered vertebrate cells, wherein the effect of the endogenous protease matriptase is impaired, clipping of a recombinant polypeptide of interest that is secreted by the cell into the cell culture medium is significantly reduced. E.g., impairing the function of the matriptase either by gene silencing (e.g. RNAi as shown in Example 1) or mutation of the endogenous matriptase gene (e.g. knockout of one or both of the two matriptase alleles as shown in Example 2 and 5) leads to a significant reduction or even complete elimination of clipping of the recombinantly expressed and secreted polypeptide of interest in the cell culture medium. A significant reduction of clipping was found for all tested polypeptides that are prone to clipping, such as IgG antibodies, Fc-fusion proteins, glycosylated viral proteins and other therapeutically active proteins. Therefore, using a matriptase deficient cell line for producing a polypeptide of interest by recombinant expression is advantageous. It is further apparent from the examples that matriptase directly cleaves the polypeptide of interest that is secreted into the cell culture medium. Thus, any impairment of the effect of the matriptase reduces clipping of the recombinantly expressed polypeptide that is secreted into the cell culture medium. Furthermore, as is demonstrated by the examples, adding a selective matriptase inhibitor to the cell culture medium may also reduce clipping.

Because the effect of the endogenous protease matriptase is impaired in the vertebrate cell according to the first aspect of the present disclosure, no or less functionally active matriptase is present in the cell culture medium in which said cells are cultured, e.g. because such cells present no or reduced amounts of functional matriptase on the cell surface and/or release (e.g. due to shedding) no or reduced amounts of functional matriptase into the cell culture medium. Thereby, the proteolytic degradation of the recombinant polypeptide of interest that is secreted into the cell culture medium is significantly reduced or even eliminated what is an important advantage when recombinantly producing a polypeptide of interest. Because clipping is significantly reduced, the yield of intact polypeptide of interest is increased. Less or even no non-functional and potentially immunogenic clipped by-product is produced. In addition, it was found that these novel vertebrate host cells generally show good expression yields and have good growth characteristics, which makes them particularly suitable as production cell lines. Further advantages are described in the following and are also apparent from the examples. Thus, these advantageous vertebrate cells allow to recombinantly produce a polypeptide of interest with improved product quality and yield. Furthermore, using the vertebrate cells according to the invention, which preferably are mammalian cells, reduces the time required for developing a production cell line for recombinant production of a polypeptide of interest. Less or even no optimization of the polypeptide of interest is necessary in order to avoid or reduce clipping e.g. by changing the amino acid sequence. In particular, removal of clipping sites becomes obsolete. Furthermore, time consuming purification processes for removing clipped protein can be avoided when using these cells as production cell line. Thus, these vertebrate cells have important advantages when being used as host cell lines for recombinant production technologies.

The sequence listing shows exemplary amino acid sequences of matriptase of different vertebrate species such as hamster (SEQ ID NO: 1—NCBI reference sequence: XP_003495890), human (SEQ ID NO: 2—NCBI reference sequence: NP_068813), mouse (SEQ ID NO: 3—NCBI Reference sequence: NP_035306), rat (SEQ ID NO: 4—NCBI reference sequence: NP_446087) and chimpanzee (SEQ ID NO: 5—NCBI reference sequence: NP_001189434). As is evident from Table 1, matriptase is currently also referred to as "suppressor of tumorigenicity 14 protein" (e.g. for human) and "suppressor of tumorigenicity 14 protein homolog" (e.g. in mouse and Chinese hamster). The term "matriptase" as used herein in particular encompasses any protein that shares at least 50%, at least 60%, at least 70%, at least 75%, at least 80%, at least 85%, at least 90%, at least 95%, at least 96%, at least 97%, at least 98% or at least 99% identity to one or more of the proteins shown in SEQ ID NO: 1 to 5 as matriptase reference protein and which has the same proteolytic activity as said matriptase reference protein. Identity as used herein is calculated over the entire length of the reference protein. Matriptase is distinguished from other proteases. In the literature, matriptase has been assigned a variety of names, a selection of which is provided in Table 1. The corresponding genes encoding the enzyme matriptase have also been assigned a variety of names, a selection of which is provided in Table 1. In the context of the invention, the protease is referred to as "matriptase", "MT-SP1", "suppressor of tumorigenicity 14 protein" or "suppressor of tumorigenicity 14 protein homolog" for the ease of simplicity. However, the term "matriptase" also refers to and encompasses any alternative names of said protein or the corresponding gene e.g. used to characterize the corresponding protein or gene in different species. Homologs and orthologs of matriptase which have the same function are included in the term "matriptase". In this context it is mentioned that matriptase-2 and matriptase-3 relate to proteases that are distinct from matriptase (although structurally related) and thus, are not covered by the term "matriptase" as used herein.

TABLE 1

Exemplary alternative names of matriptase gene and/or the encoded protein product matriptase used in the literature (alphabetical order)

Breast cancer 80 kDa protease
CAP3
Channel-activating protease 3
EC 3.4.21.109
Epithin
HAI
Matriptase
Matriptase-1
Membrane-type serine protease 1
MT-SP1; MTSP1
Prostamin
PRSS14 g.p. (*Homo sapiens*), PRSS14
Serine endopeptidase SNC19
Serine protease 14
Serine protease TADG-15; TADG-15; TADG15
SNC19
ST14 (official gene name in human according to HGNC)
St14 (official gene name in mouse according to MGI)
Suppression of tumorigenicity-14 Protein; suppression of tumorigenicity 14 (colon carcinoma, matriptase, epithin)
Suppressor of tumorigenicity 14 protein
Suppressor of tumorigenicity 14 protein homolog (mouse)
TMPRSS14
Tumor associated differentially expressed gene 15 protein A gene encoding a matriptase protein is also referred to as "matriptase gene" herein. The genomic gene sequence of different mammalian species is known, and is e.g. described in Chinese hamster (NCBI Gene-ID: 100755225); *Homo sapiens* (NCBI Gene-ID: 6768); *Mus musculus* (NCBI Gene-ID: 19143); *Rattus norvegicus* (NCBI Gene-ID: 114093); Pan Troglodytes (NCBI Gene-ID: 100188950) and others. Synonyms for the matriptase gene are listed in Table 1, commonly used is "ST14" or "St14". The term "matriptase gene" as used herein in particular encompasses any endogenous gene of a vertebrate cell which encodes a matriptase protein as shown in SEQ ID NO: 1 to 5 or which encodes a matriptase protein that shares at least 50%, at least 60%, at least 70%, at least 75%, at least 80%, at least 85%, at least 90%, at least 95%, at least 96%, at least 97%, at least 98% or at least 99% identity to one or more of the matriptase proteins shown in SEQ ID NO: 1 to 5 as matriptase reference protein and which has the same proteolytic activity as said matriptase reference protein. Identity as used herein is calculated over the entire length of the reference protein.

The present disclosure inter alia pertains to a modified vertebrate cell, such as preferably a mammalian cell, wherein the effect of the endogenous matriptase, which usually is endogenously expressed by a corresponding unmodified vertebrate cell, is impaired in said cell. Because of this alteration which impairs the effect of the endogenous protease matriptase, the altered vertebrate cell described herein presents or releases no or reduced amounts of functional matriptase into the cell culture medium, whereby clipping of the secreted polypeptide of interest in the cell culture medium is reduced or even completely prevented. As is demonstrated by the examples, this alteration, which can be transient or permanent, significantly reduces proteolytic degradation of a recombinant polypeptide of interest that is secreted by said altered cell into the cell culture medium.

There are several possibilities to alter and hence modify a vertebrate cell to impair the effect of the endogenous matriptase in said cell. The effect of the matriptase may be impaired e.g. on the gene or on protein level. The effect of matriptase can be impaired, for example, by modification of the structure/sequence of matriptase, the transcription, translation and/or cellular trafficking of matriptase. Non-limiting options are described in the following.

According to one embodiment, the effect of matriptase is impaired because functional expression of the matriptase gene is reduced or eliminated in said cell. As is shown by the examples, altering the expression of the matriptase gene by reducing or eliminating the functional expression of the matriptase gene, e.g. by gene silencing or by gene knock-out, is a very efficient measure to provide a vertebrate cell that is suitable for expressing a recombinant polypeptide of interest wherein, however, clipping of the secreted polypeptide of interest in the cell culture medium is reduced or even completely avoided. It was found that when the functional expression of the matriptase gene is reduced or eliminated in a vertebrate cell, clipping of a secreted recombinant polypeptide of interest in the cell culture medium is likewise decreased. This correlation is an unexpected finding.

Reduction or elimination of functional expression of the matriptase may be achieved by various means. Functional expression can be reduced for example by reducing the expression level of the matriptase or by reducing the catalytic activity of the matriptase or by a combination of both. According to one embodiment, the cell is altered so that the functional expression of the matriptase gene is reduced or eliminated by gene knock-out, gene mutation, gene deletion, gene silencing or a combination of any of the foregoing. According to one embodiment, the genome of the vertebrate cell is altered to impair the effect of matriptase.

According to one embodiment, functional expression of the matriptase gene is reduced or eliminated in the cell by gene knockout. A gene knockout is a genetic technique by which a gene is made inoperative by disrupting its function. E.g. a nucleic acid can be inserted into the coding sequence, thereby disrupting the gene function. Furthermore, the complete matriptase gene or a portion thereof can be deleted, whereby no or no functional protein is expressed by the respectively altered cell. Another option is to introduce one or more knock-out mutations into the coding sequence, which renders a non- or a less functional expression product. E.g. one or more frameshift mutations can be introduced that result in a non- or less-functional protein. Alternatively or additionally, one or more stop codons can be introduced into the coding sequence so that a truncated, non- or less functional protein is obtained. Hence, according to one embodiment, the matriptase gene comprises one or more mutations which provide a non- or less functional expression product. According to one embodiment, said one or more mutations are frame-shift or stop codon mutations. According to one embodiment, all or part of the protease domain located at the C-terminus of matriptase is not present due to the introduced one or more mutations. Other options include but are not limited to introducing one or more mutations in the promoter, in the 5'UTR, the 3' UTR and/or other regulatory elements. According to one embodiment, the promoter function of the matriptase gene is disrupted, e.g. by introducing a promoter deletion or by introducing a construct between the promoter and the transcription start. Methods for achieving a gene knockout to suppress or eliminate functional expression of a target gene are also well-known to the skilled person and thus, do not need any detailed description herein. Some non-limiting examples are nevertheless described below.

According to one embodiment, the matriptase gene is functionally knocked out by genetic engineering. Examples include but are not limited to genome editing, such as genome editing with engineered nucleases (GEEN). This is a type of genetic engineering in which DNA is inserted, replaced or removed from a genome using artificially engineered nucleases, or "molecular scissors." The nucleases create specific double-stranded breaks (DSBs) at desired locations in the genome, and harness the cell's endogenous mechanisms to repair the induced break by natural processes of homologous recombination (HR) and nonhomologous end-joining (NHEJ). There are at least four families of engineered nucleases that can be used for this purpose: Zinc finger nucleases (ZFNs), Transcription Activator-Like Effector Nucleases (TALENs), a nuclease recognizing Clustered Regularly Interspaced Short Palindromic Repeats (CRISPR), and engineered meganuclease re-engineered homing endonucleases. TALEN technology was also used in the examples to provide altered mammalian cells wherein the matriptase gene was fully or partially knocked out, thereby impairing the effect of matriptase in said cells.

According to one embodiment, one or more copies of the matriptase gene present in the genome of the vertebrate cell are altered, e.g. knocked-out or deleted, to reduce or eliminate and hence impair the effect of matriptase in the vertebrate cell. Thus, according to one embodiment, at least one copy of the matriptase gene is deleted or functionally inactivated in the genome of the vertebrate cell. According to one embodiment, the vertebrate cell comprises one or more mutations in at least one copy of the matriptase gene to provide a non- or less-functional expression product. In general, a vertebrate cell comprises two allelic copies of the matriptase gene. One or more mutations may be inserted into one or both copies of the matriptase gene. Preferably, one or more mutations are inserted into both, respectively all copies of the matriptase gene to provide a non- or less-functional expression product and, hence to impair the effect of matriptase in the vertebrate cell. Thereby, all copies of matriptase gene are basically impaired or inactivated in the genome. As is shown in the examples, different mutations can be introduced into the different alleles of the matriptase gene to achieve impairment.

According to one embodiment, said one or more mutations are comprised in a coding region of the matriptase gene and result in a non- or less functional expression product. E.g. the function of matriptase may be impaired because the altered vertebrate cell comprises one or more mutations in a region of the matriptase gene that encodes an amino acid sequence present in more than one catalytically active and hence functional splice variant of matriptase. Several splice variants of matriptase have been identified in different species. Several of the matriptase exons are found in the majority or even all identified functional splicing variants. It is advantageous to introduce one or more mutations into a region of the matriptase gene which encodes an exon that is present in more than one, preferably in the majority of, or even all functional matriptase splicing variants of the respective vertebrate cell.

According to one embodiment, one or more mutations are comprised in a polynucleotide sequence that encodes exon 2 of matriptase. Choosing exon 2 as target for alteration to impair the function of the endogenous protease matriptase in the altered vertebrate cell has the advantage that this approach covers several different functional splicing variants. Exons close to the N-terminus of matriptase such as e.g. exon 1, exon 2 and exon 3 are advantageous targets for introducing one or more mutations, in particular one or more frameshift mutations. A frameshift mutation in one of these exons most likely leads to a stop codon early in the sequence. The truncated protein encoded by the mutated gene is most likely short and assumed to be located intracellular and/or be non-active. An inactive truncated protein is advantageous as it can be assumed that its expression is not toxic for the cells. However, one or more mutations may also be introduced in one of the subsequent exons e.g. selected from exons 4 to 19.

In the examples, CHO cells comprising different frameshift mutations in exon 2 were generated. The examples show that respectively altered cells sustained cell growth. Therefore, the encoded truncated version(s) of matriptase tested in the examples were apparently not toxic for the cells. Furthermore, it was found that the overall mRNA expression of the respectively mutated matriptase gene was lower, so that lower levels of the truncated version were obtained (see FIG. 3). Hence, the examples demonstrate that a respective alteration is efficient in order to impair the function of matriptase in a vertebrate cell such as preferably a mammalian cell while maintaining other characteristics that are important for the recombinant production of a polypeptide of interest. Thus, according to one embodiment, the isolated vertebrate cell comprises at least one frameshift mutation in exon 2 of the matriptase gene which results in that a non- or less functional truncated polypeptide is expressed. According to a preferred embodiment, the vertebrate cell is a CHO cell which comprises one or more frameshift mutations in exon 2 of one or preferably both alleles of the matriptase gene, whereby the effect of matriptase is impaired in said CHO cell.

According to one embodiment, the vertebrate cell comprises one or more mutations in a polynucleotide sequence of the matriptase gene that encodes at least part of the catalytic domain of matriptase, whereby a non- or less functional expression product is obtained. The catalytic domain is the region of an enzyme that interacts with its substrate to cause the enzymatic reaction. One or more mutations can be introduced into this domain so that the catalytic activity of the protein is reduced or eliminated. The catalytic domain is coded by amino acids in exons 16, 17, 18 and 19. Thus, according to one embodiment, the vertebrate cell comprises one or more mutations in one or more exons selected from exon 16, exon 17, exon 18 and exon 19. According to one embodiment, the one or more mutations in the catalytic domain lead to a reduction or elimination of the catalytic activity of the matriptase. This may be achieved e.g. by a frameshift mutation, by a specific point mutation, a stop codon mutation and/or a deletion or insertion in the catalytic domain. According to one embodiment, one or more mutations are introduced so that the catalytic triad of matriptase is altered, thereby providing a non- or less functional protein. Catalytic inactive mutants of matriptase such as e.g. G827R-matriptase or S805A-matriptase have also been described in the literature (see Désilets et al, The Journal of Biological Chemistry Vol. 283, No. 16, pp. 10535-10542, 2008). Furthermore, the crystal structure of the catalytic domain of a recombinant matriptase is known. From this structure and sequence data the skilled person can derive further specific targets for mutations to impair the catalytic function of the matriptase.

Altered cells wherein functional expression of matriptase is impaired may also be obtained using random mutagenesis or screening approaches. Respective methods are known in the prior art and therefore, do not need to be described in detail. Altered cells wherein functional expression of matriptase is impaired may then be identified using e.g. the method according to the seventh aspect.

Functional expression of matriptase can also be influenced by altering the promoter and/or enhancer of the matriptase gene so that less or no transcript is produced, or by gene silencing technologies such as transcriptional or post-transcriptional gene silencing. According to one embodiment the isolated vertebrate cell comprises one or more mutations in the promoter region of the matriptase gene. For example, the promoter region may be altered to provide a less functional or non-functional promoter, the promoter may also be completely eliminated. Alternatively or in addition thereto, it is possible to add a polynucleotide sequence encoding a polypeptide including a stop codon between the promoter and the start codon of the matriptase gene which leads to the expression of the other polypeptide instead of the matriptase. The polypeptide encoded by the polynucleotide sequence inserted between the promoter and the start codon may for example be a reporter polypeptide such as green fluorescence protein (GFP). The signal of the reporter will indicate that the heterologous polynucleotide encoding the reporter is expressed instead of the matriptase thereby allowing to easily identify cells wherein the functional expression of matriptase is impaired.

Reduction of functional gene expression may achieve a level wherein functional expression is even eliminated.

Post-transcriptional gene silencing can be achieved e.g. by using antisense molecules or molecules that mediate RNA interference. Non-limiting examples will be briefly described in the following.

Antisense polynucleotides may be designed to specifically bind to RNA, resulting in the formation of RNA-DNA or RNA-RNA hybrids, with an arrest of reverse transcription or messenger RNA translation. Many forms of antisense have been developed and can be broadly categorized into enzyme-dependent antisense or steric blocking antisense. Enzyme-dependent antisense includes forms dependent on RNase H activity to degrade target mRNA, including single-stranded DNA, RNA, and phosphorothioate antisense. Antisense polynucleotides are typically generated within the cell by expression from antisense constructs that contain the antisense strand as the transcribed strand. Trans-cleaving catalytic RNAs (ribozymes) are RNA molecules possessing endoribonuclease activity. Ribozymes may be specifically designed for a particular target and may be engineered to cleave any RNA species site-specifically in the background of cellular RNA. The cleavage event renders the mRNA unstable and prevents protein expression. The genome of the vertebrate cell can be altered so that a respective antisense molecule is e.g. permanently expressed.

Another suitable option for reducing functional expression of the matriptase gene on a post-transcriptional level is based on RNA interference (RNAi). As is shown by the examples based on spike-in experiments, reducing the expression of matriptase by RNAi is effective in order to decrease the degree of clipping of recombinant polypeptides of interest that are expressed and secreted into the cell culture medium by the respectively altered vertebrate cells. Significantly more recombinant polypeptide stays intact in the supernatant/cell culture medium upon silencing of the matriptase gene by RNAi and hence, can be harvested therefrom. In contrast, reduction of the expression levels of other proteases, even closely related serine proteases, had no or little effect on clipping. This emphasizes the importance of having identified with matriptase the major protease responsible for clipping when expressing a recombinant polypeptide of interest in a vertebrate cell such as preferably in a mammalian cell. Methods for silencing a target gene by RNAi are well known to the skilled person and thus, do not need any detailed description here. Examples of RNAi inducing compounds that can be used to silence the expression of the matriptase gene thereby providing an altered cell in which the effect of matriptase is impaired, include but are not limited to short interfering nucleic acids (siNA), short interfering RNA (siRNA), microRNA (miRNA), short hairpin RNAs (shRNA) as well as precursors thereof which are processed in the cell to the actual RNAi inducing compound. According to one embodiment, a siRNA is used for silencing. The siRNA may be provided as double-stranded molecule having 3' overhangs on each strand. Blunt ended molecules may also be used. Said siRNA may comprise desoxy—as well as ribonucleotides and furthermore, may comprise modified nucleotides. Several embodiments and variations of siRNA compounds are known in the prior art and can be used to reduce expression of the matriptase. Suitable siRNAs targeting the chosen/identified target sequences of the target genes on the RNA level can be identified by using proper computational methods, applying certain design-algorithms. In order to obtain a siRNA against the target transcript, the double-stranded molecule can be transfected directly into the cell. As is shown by the examples, even such transient methods that reduce expression of the matriptase are effective to prevent clipping of a polypeptide of interest in the conditioned medium obtained from such vertebrate cells. Alternatively, the siRNA may result from processing by dicer, an enzyme that converts either long dsRNAs or small hairpin RNAs (shRNAs) into siRNAs. These precursors or the final siRNA molecules can be produced exogenously (artificially) and can then be introduced into the vertebrate cells by various transfection methods. According to a further embodiment, the RNAi inducing compound is expressed by a vector that is transfected into the vertebrate cell. For siRNA, this can be done e.g. by the introduction of a loop between the two strands, thus producing a single transcript, which can be then processed into a functional siRNA in the vertebrate cell. Such transcription cassettes typically use an RNA polymerase III promoter (for example U6 or H1) which usually direct the transcription of small nuclear RNAs (e.g. for expressing shRNAs). It is assumed that the resulting shRNA transcript from the vector is then processed by dicer, thereby producing the double-stranded siRNA molecules, preferably having the characteristic 3' overhangs. According to one embodiment, such shRNA providing vector is stably integrated into the genome of the vertebrate cell. This embodiment is advantageous, as the downregulation of the matriptase gene is due to the constantly produced siRNA rather stable and not transient. E.g. cells comprising a respective shRNA providing vector can then be transfected with an expression vector comprising a polynucleotide encoding the polypeptide of interest that is to be expressed and secreted by the vertebrate cell. Furthermore, co-transfection strategies can be used, wherein the vector generating the shRNA is co-transfected with the expression vector comprising the polynucleotide encoding the polypeptide of interest.

Transcriptional gene silencing may e.g. include epigenetic modifications. Furthermore, the sequence of the matriptase gene can be changed to reduce the half-life of the mRNA. This can also achieve a reduction in the functional expression of matriptase.

According to one embodiment, matriptase expression is reduced or eliminated by targeting a regulatory element involved in the regulation of expression of the matriptase gene. E.g. a transcription factor, promoter (see also above), enhancer, UTRs or other regulatory element can be targeted e.g. by knock-out, deletion, mutation, down-regulation or any other alteration that inactivates or reduces the activity of said regulatory element, thereby preventing or reducing functional expression of the matriptase gene and thereby impairing the effect of matriptase in said cells.

According to one embodiment the vertebrate cell is altered to impair the function of the matriptase by heterologous expression of a mutant matriptase which is non- or less functional than the endogenous matriptase. In this embodiment, the isolated vertebrate cell comprises in addition to the heterologous polynucleotide encoding the polypeptide of interest a further heterologous polynucleotide encoding a mutant matriptase. The mutant matriptase has a decreased or even no catalytic activity compared to the endogenous matriptase. By overexpressing a respective mutant matriptase the likelihood is increased that the mutant, inactive form is inserted into the plasma membrane instead of the endogenous matriptase, in order to create a dominant negative phenotype. A further option to impair and hence reduce the effect of matriptase that is normally expressed by the cell is the heterologous expression of a protein such as an antibody or matriptase inhibitor which neutralizes and/or inhibits matriptase and hence impairs the effect of matriptase.

According to one embodiment, the effect of matriptase is impaired in the cell by altering the functional expression of molecules that functionally interact with matriptase in the cell.

According to one embodiment, the function of the matriptase is impaired in the cell by impairing intracellular trafficking of the matriptase.

According to another embodiment the function of the matriptase is impaired by impairing activation of the matriptase zymogen. According to one embodiment the function of the matriptase is impaired by upregulation of one or more endogenous cellular matriptase inhibitors and/or by co-expression of a matriptase inhibitor. Several endogenous inhibitors of the matriptase have been described to date in different vertebrate cells such as HAI-1, HAI-2, alpha1-antitrypsin, alpha2-antiplasmin, antithrombin (see review by Chen et al, 2012). If expressed by the vertebrate cell to be altered, an upregulation of the expression of these inhibitors and/or a co-expression of these inhibitors may also impair the function of the endogenous protease matriptase, thereby reducing clipping of the secreted polypeptide of interest in the cell culture medium.

According to one embodiment, functional expression of matriptase is impaired by recombinant expression of an antagonist such as an antibody or a binding domain thereof. E.g. a respective antagonist can be overexpressed by the vertebrate cell.

According to one embodiment, the coding sequence of matriptase is altered so that the protein remains in the ER. E.g. the matriptase protein can be altered to include a KDEL motiv which has the effect that matriptase remains in the ER. Similar approaches may also be used.

Impairing the effect of the endogenous protease matriptase results in an altered cell wherein clipping of the recombinant polypeptide of interest that is expressed and secreted by said altered cell is reduced or even absent compared to a corresponding vertebrate cell in which the function of the endogenous protease matriptase is not impaired. As described herein, when using respectively altered cells wherein the effect of matriptase is impaired as host cells for recombinant expression, no or less functional matriptase is active in the cell culture medium containing said host cells and into which the polypeptide of interest is secreted.

According to one embodiment, expression of the matriptase gene is 40% or less, 35% or less, 30% or less, 25% or less, 20% or less, 15% or less, 12.5% or less, 10% or less, 5% or less, 2.5% or less, 1.5% or less, 1% or less or 0.05% or less compared to the expression of the matriptase gene in an unaltered corresponding reference vertebrate cell in which the effect of matriptase is not impaired (set as 100%). According to one embodiment, in the altered cell according to the first aspect expression of the matriptase gene is 0.1% or less, or less, 0.075% or less, 0.05% or less, 0.045% or less, 0.04% or less, 0.035% or less, 0.03% or less, 0.025% or less, 0.02% or less, 0.015% or less, 0.01% or less, 0.0075% or less, 0.005% or less, 0.0045% or less, 0.004% or less, 0.0035% or less, 0.003% or less, 0.0025% or less, 0.002% or less, 0.0015% or less or 0.001% or less compared to the expression of the 18S RNA (set as 100%) in said cell. According to one embodiment, expression of the matriptase gene is 0.00075% or less, 0.0005% or less or 0.0004% or less compared to the expression of the 18S RNA (set as 100%) in said cell. The functional expression of the matriptase gene is reduced or eliminated such that clipping of a recombinant polypeptide of interest that is secreted by said cell into the cell culture medium is reduced compared to a corresponding reference vertebrate cell (from which the altered cell derived) wherein the functional expression of the matriptase gene is not reduced or eliminated. E.g. an altered CHO cell in which functional expression of matriptase is reduced is compared to a CHO wildtype cell as reference vertebrate cell in order to analyze said feature. As test polypeptide, a polypeptide that is prone to clipping when expressed by the reference vertebrate cell is used. According to one embodiment, clipping is reduced by at least 2 fold, at least 3 fold, at least 5 fold, at least 7.5 fold, at least 8 fold or at least 10 fold compared to a corresponding reference vertebrate cell in which functional expression of the matriptase gene is not reduced or eliminated. This can be tested using e.g. the assays described in the examples.

The altered vertebrate cell is derived from a species and cell type which endogenously expresses matriptase. The vertebrate cell preferably is a mammalian cell. Thus, all embodiments described herein for a vertebrate cell in general apply and specifically refer to to the preferred embodiment wherein a mammalian cell is used. The term "isolated" is merely used to render clear that the vertebrate cell is not contained in a living organism such as an animal or human. As described herein, the vertebrate cell can be provided in form of a cell culture, cell line, cell clone and the like. Examples are also described below. As is described above, said vertebrate cell is altered to impair the effect of the matriptase compared to a corresponding unaltered vertebrate cell which endogenously expresses matriptase. Impairment is preferably achieved by reducing or eliminating functional expression of the matriptase gene. Embodiments are described above. In order to provide a production cell line with stable, uniform and thus predictable characteristics, it is preferred to alter the genome of the vertebrate cell to achieve matriptase impairment. Suitable embodiments are described above. The respectively altered vertebrate cell can then be transfected with an expression vector comprising a polynucleotide encoding a polypeptide of interest to provide the host cells according to the present disclosure which comprise a heterologous polynucleotide encoding the polypeptide of interest and which secrete the polypeptide of interest into the cell culture medium. The vertebrate cell preferably is a mammalian cell and may be e.g. selected from the group consisting of rodent cells, human cells and monkey cells. Preferred vertebrate cells are rodent cells such as e.g. cells derived from hamster or mouse. The rodent cell can be a cell line selected from the group consisting of a Chinese hamster cell line (such as e.g. a Chinese Hamster Ovary (CHO) cell line), a BHK cell line, a NS0 cell line, a C127 cell line, a mouse 3T3 fibroblast cell line, and a SP2/0 cell line. Particularly preferred is a CHO cell such as a CHO-K1 derived CHO cell. As is shown in the examples, reducing or eliminating the functional expression of matriptase in a CHO cell provides a conditioned cell culture medium in which clipping of the secreted polypeptide of interest is significantly decreased or even eliminated. Matriptase is also expressed in human cells. Thus, according to one embodiment, the vertebrate cell is derived from a human cell, which may be e.g. selected from the group consisting of a HEK293 cell, a MCF-7 cell, a PerC6 cell, a CAP cell, hematopoietic cells and a HeLa cell. Another alternative are monkey cells, which, e.g., may be selected from the group consisting of a COS cells, COS-1, a COS-7 cell and a Vero cell. According to one embodiment the vertebrate cell is provided as cell clone, cell line or cell culture.

The "polypeptide of interest" is the recombinant polypeptide that is supposed to be expressed and secreted by the vertebrate cell in large quantity. The polypeptide of interest is encoded by a heterologous polynucleotide comprised in said cell. Said host cell may comprise more than one heterologous polynucleotide encoding a polypeptide of interest. The polypeptide of interest is secreted by the vertebrate cell into the cell culture medium from which it can be harvested, e.g. isolated and purified.

A "heterologous polynucleotide" or "heterologous nucleic acid" and likewise expressions used herein in particular refer to a polynucleotide sequence that has been introduced into the vertebrate cell e.g. by the use of recombinant techniques such as transfection. A "polynucleotide" in particular refers to a polymer of nucleotides which are usually linked from one deoxyribose or ribose to another and refers to DNA as well as RNA, depending on the context. The term "polynucleotide" does not comprise any size restrictions.

The vertebrate cell may comprise a heterologous polynucleotide encoding a selectable marker and/or a heterologous polynucleotide encoding a reporter in addition to the at least one heterologous polynucleotide encoding the polypeptide of interest. This simplifies the selection of host cells which are successfully transfected and thus express the polypeptide of interest. Furthermore, the vertebrate cell may comprise several polynucleotides encoding different selectable markers and/or reporter polypeptides.

A "selectable marker" allows under appropriate selective culture conditions the selection of host cells expressing said selectable marker. A selectable marker provides the carrier of said marker under selective conditions with a survival and/or growth advantage. Typically, a selectable marker gene will confer resistance to a selection agent such as a drug, e.g. an antibiotic or other toxic agent, or compensate for a metabolic or catabolic defect in the host cell. It may be a positive or negative selection marker. According to one embodiment, the selectable marker is a drug resistance marker encoding a protein that confers resistance to selection conditions involving said drug. A variety of selectable marker genes have been described (see, e.g., WO 92/08796, WO 94/28143, WO2004/081167, WO2009/080759, WO2010/097240). E.g. at least one selectable marker may be used which confers resistance against one or more antibiotic agents. The selectable marker may according to one embodiment be an amplifiable selectable marker. An amplifiable selectable marker allows the selection of vector containing host cells and may promote gene amplification of said vector in the host cells. Selectable marker genes commonly used with vertebrate cells include the genes for aminoglycoside phosphotransferase (APH), hygromycin phosphotransferase (hyg), dihydrofolate reductase (DHFR), thymidine kinase (tk), glutamine synthetase, asparagine synthetase, and genes encoding resistance to neomycin (G418), puromycin, hygromycin, zeocin, ouabain, blasticidin, histidinol D, bleomycin, phleomycin and mycophenolic acid. According to one embodiment, a folate receptor is used as selectable marker in conjunction with the novel vertebrate cells described herein (see e.g. WO2009/080759), which preferably are mammalian cells. The folate receptor can also be used in combination with DHFR as selectable marker as is described in WO10/097240. A "reporter polypeptide" allows the identification of a cell expressing said reporter polypeptide based on the reporting characteristics (e.g. fluorescence). Reporter genes usually do not provide the host cells with a survival advantage. However, the expression of the reporter polypeptide can be used to differentiate between cells expressing the reporter polypeptide and those cells which do not. Therefore, also a reporter gene enables the selection of successfully transfected host cells. Suitable reporter polypeptides include but are not limited to as e.g. green fluorescence protein (GFP), YFP, CFP and luciferase. According to one embodiment, the reporter polypeptide has characteristics that enable the selection by flow cytometry.

According to one embodiment, the at least one heterologous polynucleotide encoding the polypeptide of interest is integrated into the genome of said cell and wherein optionally, at least one heterologous polynucleotide encoding a selectable marker or reporter polypeptide is additionally integrated into the genome of said cell.

An expression vector can be used to introduce a heterologous polynucleotide into the host cell. The polynucleotides can be comprised in an expression cassette. The polynucleotide(s) encoding the polypeptide of interest and the polynucleotide(s) encoding a selectable marker or reporter polypeptide may be located on the same or on different expression vectors. If they are located on different expression vectors, the expression vectors are co-transfected into the host cell. Such co-transfection strategies likewise enable selection as is well-known in the prior art. Introduction into the vertebrate cell may be achieved e.g. by transfecting a suitable expression vector comprising the polynucleotide encoding the polypeptide of interest into the host cells. The expression vector preferably integrates into the genome of the host cell (stable transfection). In case the heterologous nucleic acid is not inserted into the genome, the heterologous nucleic acid can be lost at the later stage e.g. when the cells undergo mitosis (transient transfection). Stable transfection is preferred for generating high expressing cell clones for producing a polypeptide of interest on industrial scale. This is particularly important for therapeutically active or diagnostic polypeptides of interest. Several appropriate methods are known in the prior art for introducing a heterologous nucleic acid such as an expression vector into vertebrate host cells, which preferably are mammalian host cells, and thus, do not need any detailed description herein. Respective methods include but are not limited to calcium phosphate transfection, electroporation, lipofection, biolistic- and polymer-mediated genes transfer and the like. Besides traditional random integration based methods also recombination mediated approaches can be used to transfer the heterologous polynucleotide into the host cell genome. As respective methods are well known in the prior art, they do not need any detailed description here. Non-limiting embodiments of suitable vector designs are also described subsequently and it is referred to the respective disclosure.

Expression vectors used to achieve expression of a polypeptide of interest in the host cell usually contain transcriptional control elements suitable to drive transcription such as e.g. promoters, enhancers, polyadenylation signals, transcription pausing or termination signals usually as element of an expression cassette. Suitable translational control elements are preferably included in the vector, such as e.g. 5' untranslated regions leading to 5' cap structures suitable for recruiting ribosomes and stop codons to terminate the translation process. The resultant transcripts harbour functional translation elements that facilitate protein expression (i.e. translation) and proper translation termination. A functional expression unit, capable of properly driving the expression of an incorporated polynucleotide is also referred to as an "expression cassette". It is well-known to the skilled person how an expression cassette shall be designed in order to allow the expression and secretion of a polypeptide of interest in a vertebrate cell.

To achieve secretion of the recombinant polypeptide of interest into the cell culture medium, an appropriate leader peptide is provided in the polypeptide of interest. Leader sequences and expression cassette designs to achieve secretion of the polypeptide of interest are well known in the prior art and therefore, do not need to be described herein.

Any polypeptide of interest can be expressed in the vertebrate cell according to the invention. The term "polypeptide" refers to a molecule comprising a polymer of amino acids linked together by (a) peptide bond(s). Polypeptides include polypeptides of any length, including proteins (e.g. having more than 50 amino acids) and peptides (e.g. 2-49 amino acids). Polypeptides include proteins and/or peptides of any activity, function or size, and may include e.g. enzymes (e.g. kinases, phosphatases), receptors, transporters, bactericidal and/or endotoxin-binding proteins, structural polypeptides, membrane-bound polypeptides, glycopolypeptides, globular proteins, immune polypeptides, toxins, antibiotics, hormones, growth factors, blood factors, vaccines, viral glycopolypeptides and the like. The polypeptide of interest that is expressed according to the teachings described herein may also be a subunit or domain of a polypeptide, such as e.g. a heavy chain or a light chain of an antibody or a functional fragment or derivative thereof. The term "polypeptide of interest" may refer to such individual subunit or domain or the final protein that is composed of the respective subunits or domains, depending on the context.

According to one embodiment, the polypeptide of interest is selected from a therapeutic or diagnostic polypeptide. Therapeutic and hence therapeutically active polypeptides are particularly important. The term therapeutic polypeptides also encompasses prophylactic polypeptides, e.g. used for vaccination. The polypeptide may be selected from the group consisting of peptide hormones, interleukins, tissue plasminogen activators, cytokines, growth factors, immunoglobulins, in particular antibodies or functional antibody fragments or variants or derivatives thereof and Fc-fusion proteins. In one embodiment the polypeptide of interest is an immunoglobulin molecule such as an antibody. The term "antibody" as used herein particularly refers to a protein comprising at least two heavy chains and two light chains connected by disulfide bonds. The term "antibody" includes naturally occurring antibodies as well as all recombinant forms of antibodies, e.g., humanized antibodies, fully human antibodies and chimeric antibodies. Each heavy chain is usually comprised of a heavy chain variable region (VH) and a heavy chain constant region (CH). Each light chain is usually comprised of a light chain variable region (VL) and a light chain constant region (CL). The term "antibody", however, also includes other types of antibodies such as single domain antibodies, heavy chain antibodies, i.e. antibodies only composed of one or more, in particular two heavy chains, and nanobodies, i.e. antibodies only composed of a single monomeric variable domain. Nanobodies may also be linked to form multivalent structures. As discussed above, the polynucleotide encoding the polypeptide of interest may also encode one or more subunits or domains of an antibody, e.g. a heavy or a light chain or a functional fragment or derivative thereof, as polypeptide of interest. Said subunits or domains can be expressed either from the same or different expression cassettes.

A "functional fragment or derivative" of an antibody in particular refers to a polypeptide which is derived from an antibody and is capable of binding to the same antigen, in particular to the same epitope as the antibody. It has been shown that the antigen-binding function of an antibody can be executed by fragments of a full-length antibody or derivatives thereof. Examples of fragments or derivatives of an antibody include (i) Fab fragments, monovalent fragments consisting of the variable region and the first constant domain of each the heavy and the light chain; (ii) F(ab)$_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)$_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular.

According to one embodiment the polypeptide of interest that is expressed by the altered vertebrate cell is susceptible to clipping by proteases. According to one embodiment, the polypeptide of interest comprises at least one clipping site that is recognized by matriptase. Several polypeptides selected from the group consisting of glycoproteins, antibodies, non-IgG proteins, Fab fragments, protein complexes, peptidases, signal peptides, Fc-fusion proteins, nanobodies, growth factors, hormones, cytokines, viral glycopolypeptides, blood factors and enzymes have been identified that are prone to clipping. Many of these polypeptides contain more than one clipping site and are particularly sensitive to clipping. Expressing a polypeptide that is prone to clipping as polypeptide of interest in an altered vertebrate cell according to the present disclosure is advantageous because clipping of the secreted polypeptide of interest in the cell culture medium is significantly reduced or even eliminated as is demonstrated by the examples.

The vertebrate cell may or may not comprise an endogenous polynucleotide corresponding to, respectively being identical to the polynucleotide encoding the polypeptide of interest. According to one embodiment, the vertebrate cell does not comprise an endogenous gene corresponding to the polypeptide of interest.

According to one embodiment, the polypeptide of interest is not or does not comprise matriptase. According to one embodiment, the polypeptide of interest is not or does not comprise HAI-1.

The expression vector or the combination of expression vectors that are comprised in the vertebrate cell may additionally comprise further vector elements. E.g. at least one additional polynucleotide encoding a further product of interest can be comprised. As explained above and as becomes apparent from the above described examples of polypeptides that can be expressed according to the present teachings, the final polypeptide that is to be produced and secreted by the host cell can also be a protein that is composed of several individual subunits or domains. An example of a respective protein is an immunoglobulin molecule, in particular an antibody that comprises e.g. heavy and light chains. There are several options for producing a respective protein that is composed of different individual subunits or domains and appropriate vector designs are known in the art. According to one embodiment, two or more subunits or domains of said protein are expressed from one expression cassette. In this embodiment, one long transcript is obtained from the respective expression cassette that comprises the coding regions of the individual subunits or domains of the protein. According to one embodiment, at least one IRES element (internal ribosomal entry site) is functionally located between the coding regions of the individual subunits or domains and each coding region is preceded by a secretory leader sequence. Thereby, it is ensured that separate translation products are obtained from said transcript and that the final protein can be correctly assembled and secreted. Respective technologies are known in the prior art and thus, do not need any detailed description herein. For some embodiments such as the expression of antibodies it is even preferred to express the individual subunits or domains from different expression cassettes. According to one embodiment, the expression cassette used for expressing the product of interest is a monocistronic expression cassette. All expression cassettes comprised in the expression vector or combination of expression vectors may be monocistronic. According to one embodiment, accordingly, each expression cassette designed for expressing a product of interest comprises a polynucleotide encoding one subunit or domain of the protein to be expressed as polypeptide of interest. E.g. in case of antibodies, one expression cassette may encode the light chain of an antibody and another expression cassette may encode the heavy chain of the antibody. After expression of the individual subunits or domains from the individual expression cassettes, the final protein such as an antibody is assembled from said subunits or domains and secreted by the host cell. This embodiment is particularly suitable for expressing immunoglobulin molecules such as antibodies.

As described above, the polynucleotide(s) encoding the polypeptide of interest and the polynucleotides encoding the selectable marker(s) and/or reporter polypeptide(s) are preferably comprised in expression cassettes. Several embodiments are suitable. For example, each of said polynucleotide(s) can be comprised in a separate expression cassette. This is also referred to as monocistronic setting. However, it is also within the scope of the present invention that at least two of the respective polynucleotides are comprised in one expression cassette. According to one embodiment, at least one internal ribosomal entry site (IRES) element is functionally located between the polynucleotides that are expressed from the same expression cassette. Respective IRES based expression technologies and other bi- and polycistronic systems are well known and thus need no further description here.

B. Method for Producing a Vertebrate Cell According to the First Aspect

According to a second aspect, a method is provided for producing a vertebrate cell according to the first aspect, said method comprising altering a vertebrate cell to impair the effect of matriptase and introducing a polynucleotide encoding a polypeptide of interest into said cell, wherein said polypeptide of interest is then secreted by the vertebrate cell.

Suitable and preferred embodiments to impair the function of the endogenous protease matriptase are described above in conjunction with the vertebrate cells according to the first aspect and it is referred to the above disclosure, which also applies here. Therefore, the method may comprise impairing the effect of matriptase as described above in conjunction with the altered vertebrate cells according to the first aspect. Non-limiting embodiments are again briefly described in the following.

According to one embodiment, the method comprises reducing or eliminating the functional expression of the matriptase gene thereby impairing the effect of the matriptase. As described above, this impairment has the effect that no or reduced amounts of functional matriptase is present in active form in the cell culture medium containing the altered cells, e.g. because no or reduced amounts of functional matriptase is presented on the cell surface and/or is released, e.g. shedded, by the altered cell. Thereby, no or less matriptase is present in proteolytically active form in the cell culture medium into which the recombinant polypeptide of interest is secreted. As the present disclosure shows that matriptase is a key protease responsible for clipping of the secreted polypeptide of interest, this alteration of the cell advantageously reduces or even eliminates clipping of the polypeptide of interest. Suitable ways for reducing or eliminating functional expression of matriptase are described above in conjunction with the vertebrate cells according to the first aspect and it is referred thereto. According to one embodiment, the genome of the vertebrate cell is altered to reduce or eliminate the functional expression of matriptase gene. For example, a gene knock-out may be introduced into the matriptase gene. According to one embodiment, such gene knock-out is introduced into all copies of the matriptase gene. According to one embodiment, the matriptase gene is deleted or knocked-out by introducing one or more mutations such as e.g. frameshift and/or stop codon mutations. All copies of the matriptase gene may be respectively altered in the genome.

According to one embodiment, said one or more mutations are comprised in a coding region of the matriptase gene and result in a non- or less functional expression product. Details are described above in conjunction with the altered vertebrate cells according to the first aspect and it is referred to the respective disclosure which also applies here. According to one embodiment, one or more mutations are introduced into a region of the matriptase gene that encodes an amino acid sequence present in one or more than one catalytically active splice variant of matriptase. Several of the matriptase exons are found in the majority or even all identified catalytically active splicing variants. As described above and demonstrated in the examples, the polynucleotide sequence of the matriptase gene that encodes exon 2 of matriptase is a suitable target for introducing one or more mutations such as e.g. frame-shift mutations, because exon 2 is expressed in the majority of splice variants of matriptase and a respective mutation renders a non- or less functional expression product. Moreover, exons close to the N-terminus of matriptase such as exon 2 are advantageous targets for introducing one or more frameshift mutations leading to the expression of a non- or less functional truncated protein. Furthermore, one or more mutations can be introduced into the catalytical domain in order to disrupt the function of matriptase.

According to one embodiment, the vertebrate cell is a mammalian cell. According to one embodiment, the vertebrate cell is a rodent cell. Preferably, the rodent cell is a hamster cell such as a CHO cell. According to one embodiment, a CHO cell, preferably derived from the cell line K1, is used in order to provide an altered vertebrate cell line wherein the effect of the endogenous protease matriptase is impaired, preferably by reducing or eliminating the functional expression of the matriptase gene.

If the genome of the host cell is altered to achieve impairment, it is preferred to first alter the vertebrate cell to basically permanently impair the effect and hence function of the endogenous protease matriptase and then introduce the heterologous polynucleotide encoding the polypeptide of interest. In case the alteration is not permanent as is e.g. the case when transiently silencing the matriptase gene, e.g. via RNAi, one may first introduce the heterologous polynucleotide encoding the polypeptide of interest and then alter the vertebrate cell to impair the function of the endogenous protease matriptase, e.g. by post-transcriptional gene silencing. Suitable methods were described above and are known to the skilled person. As described above, according to a preferred embodiment, the genome of the vertebrate cell is altered to achieve impairment. The method according to the seventh aspect can be used in order to identify and select a host cell wherein the effect of matriptase is impaired.

According to one embodiment, the method according to the second aspect further comprises introducing into a vertebrate cell which is altered so that the functional expression of matriptase gene is reduced or eliminated, at least one polynucleotide encoding a polypeptide of interest and preferably at least one polynucleotide encoding a selectable marker. According to one embodiment, the polynucleotide encoding a polypeptide of interest and the polynucleotide encoding a selectable marker are located on the same or on different expression vectors. Suitable and preferred embodiments are described above and it is referred to the respective disclosure, which also applies here. Introduction can be achieved by transfection, wherein stable transfection is preferred. A vertebrate host cell that successfully expresses the polypeptide of interest can be selected using e.g. the method according to the fifth aspect. It is referred to the subsequent disclosure.

C. Methods for Recombinantly Producing a Polypeptide of Interest

According to a third aspect, a method is provided for recombinantly producing a polypeptide of interest, comprising utilizing a vertebrate cell according to the first aspect as host cell for recombinant expression of the polypeptide of interest. As described above, due to the decreased level of proteolytic degradation of the polypeptide of interest in the cell culture medium that is achieved when using these novel vertebrate cells for recombinant expression, these novel vertebrate cells, which preferably are mammalian cells, are particularly suitable as host cells for recombinantly producing a polypeptide of interest. Suitable and preferred examples of the vertebrate host cell, which is altered to impair the effect of the matriptase, preferably by reducing or eliminating functional expression of the matriptase gene, as well as suitable and preferred examples of the polypeptide of interest are described in detail above and it is referred to the above disclosure which also applies here.

According to one embodiment, the method comprises introducing into a vertebrate host cell which is altered so that the effect of the endogenous protease matriptase is impaired at least one polynucleotide encoding a polypeptide of interest and selecting a vertebrate host cell which recombinantly expresses the polypeptide of interest. Introduction can be achieved by transfection as is well-known and also described herein. Selection may occur using the method according to the fifth aspect of the present disclosure. Preferably, host cells are selected wherein the heterologous polynucleotide encoding the polypeptide of interest is stably integrated into the genome of the host cell.

According to one embodiment, the method comprises
(a) culturing vertebrate host cells according to first aspect under conditions that allow for the expression and secretion of the polypeptide of interest;
(b) isolating the polypeptide of interest from the cell culture medium; and
(c) optionally processing the isolated polypeptide of interest.

Hence, as preferred embodiment of the method according to the third aspect, a method for recombinantly producing a polypeptide of interest is provided, comprising
(a) culturing vertebrate host cells according to the first aspect under conditions that allow for the expression and secretion of the polypeptide of interest into the cell culture medium;
(b) isolating the polypeptide of interest from the cell culture medium; and
(c) optionally processing the isolated polypeptide of interest.

Said host cells may be cultured under serum-free conditions. The polypeptide is expressed and secreted into the culture medium and can be obtained therefrom. For the purpose of secretion, an appropriate leader peptide is provided so that the polypeptide of interest is secreted. Leader sequences and expression cassette designs to achieve secretion are well known in the prior art and therefore do not need to be described herein.

As described above, when using the altered vertebrate cells according to the first aspect for production host cells, no or reduced amounts of functional matriptase are effective in the cell culture medium containing said cells, whereby proteolytic degradation of the recombinant polypeptide of interest that is secreted into the cell culture medium is significantly reduced or is even completely avoided. This, because it was surprisingly found that among the hundreds of different proteases expressed by vertebrate cells, matriptase is the key protease that causes clipping of recombinantly expressed polypeptides in the cell culture medium. Therefore, when using the novel vertebrate host cells according to the present disclosure as production host cells, it is not necessary to perform additional measures to reduce or avoid proteolytic degradation and hence clipping of the polypeptide of interest in the cell culture medium. Therefore, according to one embodiment, no protease inhibitor is added to the cell culture medium. According to one embodiment, the cultivation temperature is not lowered to reduce the proteolytic activity in the cell culture medium. The present disclosure encompasses methods wherein the polypeptide of interest is reengineered to remove one or more motives prone to clipping by proteases. However, according to one embodiment, the polypeptide of interest is not reengineered in order to remove one or more amino acid motives that are prone to clipping by matriptase in order to reduce or prevent clipping. According to this embodiment, a respective reengineering may be performed if desired in order to remove one or more amino acid motives that are prone to clipping by a protease different than matriptase. However, according to one embodiment, the polypeptide of interest is not reengineered at all in order to remove one or more amino acid motives that are prone to clipping by a protease in order to reduce or prevent clipping. As is shown by the examples, clipping is effectively reduced or even completely eliminated when using the altered cells described herein so that respective reengineering approached become basically obsolete.

Examples of polypeptides of interest that may be produced with the altered vertebrate cell are described above in conjunction with the first aspect of the invention and it is referred to the respective disclosure, which also applies here. According to one embodiment, the production method is used for producing a polypeptide of interest which has one or more of the following characteristics:
  a) it is therapeutic or diagnostic polypeptide;
  b) it is susceptible to clipping by proteases;
  c) it comprises at least one clipping site for matriptase;
  d) it is a glycopolypeptide;
  e) it is selected from the group consisting of glycoproteins, antibodies, non-IgG proteins, Fab fragments, protein complexes, peptidases, signal peptides, Fc-fusion proteins, nanobodies, growth factors, hormones, cytokines, blood factors and enzymes;
  f) it is not or does not comprise matriptase; and/or
  g) it is not or does not comprise HAI-1.

The polypeptide of interest that is produced is isolated from the cell culture medium and optionally further processed by methods known in the art. For example, the polypeptide may be recovered from the nutrient medium by conventional procedures including, but not limited to, centrifugation, filtration, ultra-filtration, extraction or precipitation. Further processing steps such as purification steps may be performed by a variety of procedures known in the art including, but not limited to, chromatography (e.g. ion exchange, affinity, hydrophobic, chromatofocusing, protein A or protein G chromatography and size exclusion), electrophoretic procedures (e.g., preparative isoelectric focusing), differential solubility (e.g. ammonium sulphate precipitation) or extraction. Furthermore, the isolated and purified polypeptide of interest may be further processed, such as e.g. modified and/or formulated into a composition, e.g. a pharmaceutical composition.

According to a fourth aspect, a method for recombinantly producing a polypeptide of interest is provided, comprising
(a) culturing vertebrate host cells which comprise at least one heterologous polynucleotide encoding a polypeptide of interest under conditions that allow for the expression and secretion of the polypeptide of interest into the cell culture medium, wherein the cell culture medium comprises a protease inhibitor that is selective for matriptase;
(b) isolating the polypeptide of interest from the cell culture medium; and
(c) optionally processing the isolated polypeptide of interest.

The method according to the fourth aspect is also based on the important finding described herein that matriptase is the key protease responsible for the proteolytic degradation of the secreted recombinant polypeptide of interest in the cell culture medium. In the method according to the fourth aspect, the proteolytic degradation of the polypeptide of interest in the cell culture medium, also referred to as "clipping" (see above) is avoided by adding a protease inhibitor that is selective for matriptase to the cell culture medium. A protease inhibitor that is selective for matriptase is also referred to herein as selective matriptase inhibitor. Of course, also more than one selective matriptase inhibitors can be added. As is demonstrated by Example 4, adding a selective matriptase inhibitor to the cell culture medium allows to significantly reduce or even abolish clipping of the polypeptide of interest even when using vertebrate cells that normally express matriptase. Thus, this embodiment allows to use unaltered vertebrate cells wherein accordingly, the effect of matriptase is not impaired because impairment is achieved in the cell culture medium.

The selective matriptase inhibitor present in the cell culture medium leads to a decrease or abolishment of the proteolytic activity of matriptase in the cell culture medium. The matriptase inhibitor may e.g. be a competitive inhibitor that competes with the substrate for the active site of the matriptase or an allosteric inhibitor that modifies the structure of the matriptase to reduce its activity. A matriptase inhibitor is considered selective, if its inhibitory activity against matriptase is higher than its inhibitory activity against other serine proteases, in particular other type II transmembrane serine proteases.

The selective matriptase inhibitor may be of any kind as long as it does not show harmful effects on the host cell that is used for producing the recombinant polypeptide of interest. The selective matriptase inhibitor may be selected from i) biological matriptase inhibitors which include but are not limited to antibody based or antibody derived selective matriptase inhibitors, peptides or proteins and ii) chemical matriptase inhibitors such as small molecules.

According to one embodiment, the selective matriptase inhibitor is at least 5 fold, at least fold, at least 25 fold, at least 50 fold, at least 100 fold or at least 250 fold more selective and thus specific for matriptase than to other proteases. However, the selectivity may also be substantially higher, such as e.g. at least 500 fold, at least 5000 fold, at least 10000 fold, at least 50000 fold, at least 500000 fold and at least 5000000 fold. Ranges include but are not limited to 5 fold to 10 000 000 fold, 10 fold to 5000000 fold, 25 fold to 1000000 fold, 50 fold to 5000000 fold. A higher selectivity of e.g. at least 5000 fold or at least 10 000 fold and higher may be achieved e.g. with selective biological matriptase inhibitors, such as e.g. matriptase specific antibodies or Fab-fragments.

Selectivity may be determined e.g. based on the $k_i$-value, which is for a selective matriptase inhibitor lower than for other tested proteases. According to one embodiment, the matriptase inhibitor inhibits matriptase selective with a $k_i$ value of 200 nM or less, 150 nM or less, 100 nM or less, 50 nM or less, 25 nM or less, 20 nM or less, 15 nM or less, 10 nM or less, 7.5 nM or less, 5 nM or less, 2.5 nm or less, 1 nM or less or 0.75 nM or less.

As mentioned above, several selective matriptase inhibitors are described in the prior art. E.g. Farady et al describe different antibody based selective matriptase inhibitors, namely a Fab fragment (Farady et al., 2008 J. Mol. Biol. (2008) 380, 351-360) and two scFv antibody inhibitors (J Mol Biol. 2007 Jun. 15; 369 (4): 1041-1051). The single chain variable fragment (scFv) antibody inhibitors E2 and S4 with Ki values of 12 μM and 160 μM, were described as particularly selective. An antibody-based selective matriptase inhibitor may be active against matriptase derived from different species. As is demonstrated by Example 4, e.g. the Fab-fragment against human matriptase was also effective against matriptase derived from mouse and hamster. However, respective antibody-based selective matriptase inhibitors may also be generated against the specific matriptase expressed by the concerned host cell in order to ensure a maximal inhibitory effect and allow to use lower concentrations of the selective matriptase inhibitor in the cell culture medium. Moreover, antibodies specific for the catalytic site of the matriptase have been described (US 2006/171884 A1). Peptidomimetic molecule selective matriptase inhibitors such as the 3-amidinophenyl-alanine type molecules CJ-730 and CJ-697 have $k_i$-values for matriptase of 46 nM and 26 nM, respectively (described in Forbs et al. International Journal of Oncology 27: 1061-1070 2005). As is described in Forbs, addition of these compounds to cell culture of tumour cell lines reduces the matriptase activity significantly without influencing the proliferation of the cells. Selective inhibitors of matriptase are also described in Steinmetzer et al, J. Med. Chem. 2006, 49, 4116-4126 and Goswami et al, ACS Med. Chem. Lett., 2013 4 (12) pp 1152-1157. Furthermore, structural variants of the eglin c, a small monomeric protein which is a serine protease inhibitor, have been identified as respective matriptase inhibitors (Desilets et al. FEBS Letters 580 (2006) 2227-2232). Here, in a screening assay different structural variants of eglin c were created and tested for their specificity for matriptase. A single amino acid exchange (L45R) in the reactive site loop makes eglin c matriptase specific ($k_i$=18 nM). Thus, many selective matriptase inhibitors are known that can be used for the purpose of the present disclosure in order to selectively inhibit matriptase in the cell culture medium thereby reducing or preventing clipping of the polypeptide of interest that is recombinantly expressed and secreted into the cell culture medium by the vertebrate host cell.

For impairing the effect of the matriptase in the cell culture medium, the selective matriptase inhibitor may be added to the cell culture medium in which the expression host cells are cultivated. The concentration of an individual selective matriptase inhibitor required to achieve sufficient matriptase inhibition in the cell culture medium so that the proteolytic degradation of the polypeptide of interest is reduced can be determined based on routine experiments. The selective matriptase inhibitor may be added to the cell culture medium before or after addition of the host cells.

According to one embodiment, the selective matriptase inhibitor is added at the start of cell cultivation. According to one embodiment, the selective matriptase inhibitor is added at a point in time, wherein the host cells begin secretion of the polypeptide of interest. The selective matriptase inhibitor may also be added continuously. For example, in fed batch cultivation the selective matriptase inhibitor may be included in the feed.

Details with respect to the polypeptide of interest, the isolation of the polypeptide of interest from the cell culture medium as well as the subsequent processing are described above e.g. in conjunction with the method according to the third aspect and it is referred to the above disclosure which also applies here.

Considering the cell culture volume required for large scale production, large quantities of the (one or more) selective matriptase inhibitor must be added to the cell culture medium even if a matriptase inhibitor with a high selectivity is used in order to efficiently reduce or prevent clipping of the polypeptide of interest in the cell culture medium. This can be costly. Additionally, for many polypeptides of interest such as biopharmaceuticals, the added selective matriptase inhibitor must be eliminated during the subsequent isolation and purification of the polypeptide of interest to avoid contaminations of the final polypeptide of interest with the matriptase inhibitor. Such removal step may comprise any known purification step such as ion exchange, affinity, size exclusion, or reversed phase chromatography. The eligible method of removal is dependent on the type of selective matriptase inhibitor used. As such steps can be laborious and may increase costs, the method according to the third aspect which involves the use of altered vertebrate cells according to the first aspect is preferred.

D. Selection Method

According to a fifth aspect, a method is provided for selecting a host cell which recombinantly expresses a polypeptide of interest, comprising
  (a) providing vertebrate cells according the first aspect of the invention as host cells; and
  (b) selecting one or more host cells expressing the polypeptide of interest.

The vertebrate host cells according to the first aspect, including suitable and preferred embodiments, as well as their advantages are described in detail above and it is referred to the respective disclosure which also applies here. Preferably, the vertebrate cell is a mammalian cell. According to one embodiment, stage (a) of the selection method according to the fifth aspect comprises transfecting vertebrate cells, which are altered to impair the effect of the endogenous protease matriptase with at least one polynucleotide encoding the polypeptide of interest, to provide vertebrate host cells according to the first aspect. According to one embodiment, the cells do not comprise a heterologous polynucleotide encoding a polypeptide of interest prior to transfection of the polynucleotide encoding the polypeptide of interest to be expressed and secreted by the host cell. As described, mammalian cells are preferably used as vertebrate host cells. The polynucleotide encoding the product of interest may be comprised in an expression vector that is then transfected into the vertebrate cell.

According to one embodiment said host cells provided in stage (a) additionally comprise at least one heterologous polynucleotide encoding a selectable marker and stage (b) comprises culturing said plurality of host cells under conditions selective for the selectable marker. Selection stage (b) may be a multi-step selection process comprising several selection steps in order to select and thus identify host cells that express the polypeptide of interest. Thus, according to one embodiment selection stage (b) may comprise several selection steps. For example, stage (b) may include one or more selection steps to select cells that were successfully transfected as well as one or more subsequent selection steps to select high expressing cells from the pool of successfully transfected cells. The appropriate selection strategy depends on the design of the expression vector that is used for introducing the polynucleotide encoding the polypeptide of interest and in particular depends on the used selection marker(s) and/or reporter(s). Non-limiting embodiments will be described in the following.

As described above, the vertebrate host cells may comprise at least one heterologous polynucleotide encoding a selectable marker. The polynucleotide encoding the selectable marker can be introduced into the host cell together with the polynucleotide encoding the polypeptide of interest using either the same or a different, co-transfected expression vector. Stage (b) then comprises culturing said plurality of host cells under conditions providing a selection pressure to the host cells to select successfully transfected host cells, e.g. using an appropriate selection medium. As used herein, a "selection medium" in particular refers to a cell culture medium useful for the selection of host cells that express the selectable marker. It may include e.g. a selection agent such as a toxic agent which allows selecting successfully transfected host cells. Alternatively, an essential compound can be absent or its concentration can be reduced in the selection medium. According to one embodiment, host cells which were not successfully transfected and hence, do not express the selection marker(s) or wherein expression is low cannot proliferate or die under the selective cultivation conditions. In contrast, host cells which were successfully transfected with the expression vector(s) and which express the selection marker(s) (and accordingly the co-introduced polypeptide of interest) with sufficient yield are resistant to or are less affected by the selection pressure and therefore, can proliferate, thereby outgrowing the host cells which were not successfully transfected or wherein the integration site into the genome of the cell is not favourable. The selectable marker may be selected from the group consisting of antibiotic resistance markers, drug resistance markers and metabolic markers. Suitable examples for selectable markers and selection principles are described above in conjunction with the first aspect and appropriate selection conditions for the individual selectable markers are also well-known to the skilled person. As described above, alternatively or additionally, a reporter polypeptide based selection can be performed.

According to one embodiment, the vertebrate cells provided in stage (a) are mammalian cells. According to one embodiment, the mammalian cells are rodent cells, preferably hamster cells such as CHO cells. Suitable and preferred embodiments are described above in conjunction with the first aspect and it is referred to the above disclosure. Further preferred embodiments in particular with respect to the vertebrate host cells according to the first aspect, the expression vector, or combination of expression vectors are likewise described in detail above. It is referred to the above disclosure.

Cells obtained as a result of the selection method according to the fifth aspect can be isolated and cultured as individual cells. It is, however, also possible to use an enriched population of genetically different host cells, i.e. a cell pool, in the downstream process. The obtained host cells can also be subjected to additional qualitative or quantitative analysis, or can be used e.g. in the development of a clonal cell line for protein production. A clonal cell line may be established from a selected host cell which stably expresses the polypeptide of interest with high yield.

According to one embodiment, selected cells are cultivated to provide cell clones, in particular in the form of clonal cell cultures. A clonal cell culture is a cell culture derived from one single ancestral cell. In a clonal cell culture, all cells are clones of each other. Preferably, all the cells in a cell culture contain the same or substantially the same genetic information. In certain embodiments, the amount or concentration of the polypeptide of interest in the cell culture is determined to evaluate the productivity. E.g. the titer can be measured by analysing the culture supernatant. Furthermore, a stability study can be performed with the obtained cell clones.

E. Use of Altered Vertebrate Cells for Recombinant Production

According to a sixth aspect, the use of an isolated vertebrate cell is provided for recombinant production of a polypeptide of interest that is secreted from the vertebrate cell, wherein the used cell is altered to impair the effect of the endogenous protease matriptase. According to one embodiment of the sixth aspect the effect of the matriptase is impaired as is described in detail above in conjunction with the first aspect, preferably by reducing or eliminating functional expression of the matriptase gene as is described above in further detail. The vertebrate cell is preferably a mammalian cell. Thus, according to one embodiment, the effect of the endogenous protease matriptase is impaired as described above in conjunction with the altered vertebrate cells according to the first aspect. According to one embodiment, a polynucleotide encoding a polypeptide of interest is introduced into said cell. After introduction, a vertebrate cell is provided which comprises a heterologous polynucleotide encoding a polypeptide of interest that is then secreted from the vertebrate cell into the cell culture medium. Thus, the use may comprise introducing a heterologous polynucleotide encoding a polypeptide of interest into said vertebrate cell, wherein said polypeptide of interest is secreted by the vertebrate cell. Details with respect to the polypeptide of interest are likewise described in detail above and it is referred to the respective disclosure which also applies here. Methods for introducing a polynucleotide into a vertebrate cell are known to the skilled person and are also briefly described above.

According to one embodiment, the vertebrate cell does not comprise a heterologous polypeptide encoding a polypeptide of interest prior to introducing the polynucleotide encoding the polypeptide of interest to be expressed. According to one embodiment, said cell further does not comprise a heterologous polynucleotide encoding a selectable marker and/or a heterologous polynucleotide encoding a reporter polypeptide. According to one embodiment, the vertebrate cell does not comprise any heterologous polynucleotide prior to introduction of the polynucleotide encoding the polypeptide of interest. A respective "empty" vertebrate cell which is altered to impair the effect of the endogenous protease matriptase can be used e.g. as cloning cell line for recombinant production technologies. A respective cell line can be transfected with a heterologous polynucleotide encoding a polypeptide of interest, e.g. using an appropriate expression vector. Such "empty" vertebrate cells which do not yet express and secrete a recombinant product can thus be transfected with different expression vectors, depending on the desired polypeptide of interest that is supposed to be recombinantly produced. Thus, such vertebrate cell line can be used for different projects, i.e. for the production of different polypeptides of interest. According to one embodiment, the vertebrate cell is a vertebrate cell according to the first aspect. Details are described above and it is referred to the above disclosure.

F. Method for Selecting Vertebrate Host Cells with Impaired Matriptase Function

According to a seventh aspect, the present disclosure pertains to a method for selecting a vertebrate cell for recombinant production of a polypeptide of interest, comprising analyzing if the endogenous protease matriptase is functionally expressed in the vertebrate cell and selecting a vertebrate cell in which the effect of such endogenous matriptase is impaired for recombinant production of the polypeptide of interest. This selection process allows identifying a host cell that is capable of expressing and secreting a recombinant polypeptide of interest, wherein clipping of the secreted polypeptide of interest in the cell culture medium is reduced. Respective host cells are particularly suitable for recombinant production.

This analytical method can be advantageously used e.g. in combination with the method according to the second aspect of the present disclosure in order to identify whether a vertebrate cell was produced wherein the effect of the matriptase gene was impaired. According to a preferred embodiment, the method comprises analyzing whether the functional expression of the matriptase gene is reduced or eliminated in said cells. Non-limiting embodiments are described in the following. Which analytical method is suitable also depends on how the cells are altered to achieve a reduction or elimination of the functional expression of the matriptase.

For example, when introducing a gene knock-out into the matriptase gene in order to reduce or eliminate functional expression of matriptase, one can amplify the corresponding DNA section and sequence the amplified DNA in order to confirm that the gene knock-out was introduced into the matriptase gene. The introduction of one or more mutations can be detected e.g. by sequencing. If functional expression of the matriptase is reduced or eliminated by completely or partly deleting said gene one can detect the deletion on the DNA level, e.g. using suitable amplification based detection methods to detect the deletion (such methods are known to the skilled person).

Furthermore, the method can be used in order to select a suitable cell line wherein naturally functional expression of matriptase is reduced or eliminated, e.g. because the overall expression is reduced or eliminated and/or because the activity of the expressed matriptase is reduced or eliminated e.g. due to at least one mutation. Respective cells can be identified using the method according to the seventh aspect as is described herein. E.g. expression of matriptase can be analysed using PCR based techniques such as RT-PCR and/or sequencing. Alternatively or additionally, the activity of matriptase can be analysed using conditioned medium obtained from the cells to be analysed.

According to one embodiment, cells with no or reduced amount of matriptase on the cell surface are selected by flow cytometry. E.g. an antibody or other detection agent that binds matriptase can be used to mark the cells that express matriptase. Respective cells can then be labelled by adding a labelled agent that binds the antibody or other detection agent, or the antibody or other detection agent may be labelled directly. According to one embodiment, the label is a fluorescent label. Thereby, the cells are marked according to their expression level of matriptase which allows to then identify and sort the cells which show reduced or no expression of matriptase, e.g. by fluorescence activated cell sorting (FACS).

According to one embodiment, the expression profile of the vertebrate cells is analyzed to determine whether functional expression of the matriptase gene is reduced or eliminated. For example, the analysis may comprise performing a qualitative or quantitative RT (reverse transcription) PCR in order to detect the presence, absence, amount or length of matriptase mRNA. In addition or alternatively to the analysis of functional matriptase expression in the cell, the selection process may comprise a step of testing whether there is matriptase activity in conditioned medium obtained from said cell. For example, spike-in experiments as described in the examples may be performed. Accordingly, the cell culture medium may be collected from a variety of potential cell lines in order to analyse whether there is matriptase activity in the respectively obtained conditioned medium. E.g. the conditioned medium may be tested for its clipping activity on a polypeptide that is prone to clipping. By using one or more polypeptides that are known to be clipped as standard for testing the clipping activity, it is possible to qualify or quantify the clipping activity of the potential cell lines relative to each other or to a standard cell line.

According to one embodiment the method according to the seventh aspect is for selecting mammalian cells, in particular rodent cells such as hamster cells, preferably CHO cells.

According to one embodiment, the method according to the seventh aspect comprises selecting at least one cell wherein the function of the matriptase is impaired, preferably by reduction or elimination of functional expression of the matriptase gene for recombinant expression of a polypeptide of interest. Cells having the respective characteristics are particularly suitable for recombinant expression as shown by the examples. Further embodiments of respective cells are also described in detail above and it is referred to the respective disclosure.

Numeric ranges described herein are inclusive of the numbers defining the range. The headings provided herein are not limitations of the various aspects or embodiments of this disclosure which can be read by reference to the specification as a whole. According to one embodiment, subject-matter described herein as comprising certain elements also refers to subject-matter consisting of the respective elements. In particular, the polynucleotides described herein as comprising certain sequences may also consist of the respective sequences. It is preferred to select and combine preferred embodiments described herein and the specific subject-matter arising from a respective combination of preferred embodiments also belongs to the present disclosure. All documents cited herein are incorporated by reference.

EXAMPLES

The following examples serve to illustrate the present invention without in any way limiting the scope thereof. In particular, the examples relate to preferred embodiments of the present invention.

I. Materials and Methods

1. Cell Culture

Unless described otherwise herein, as cell culture, suspension growing CHO cells derived from CHO-K1 were cultivated in shake flasks in a standard medium and cell culture process as disclosed e.g. in WO2011/134920. Cells were passaged 2 times per week into fresh media and were maintained in logarithmic growth phase throughout the study.

The same culture medium that was used for culturing the cells was used as positive control in the examples.

2. Spike-in Experiments Using Conditioned Medium

Cells which do not comprise a heterologous polynucleotide encoding a polypeptide of interest were passaged at a density of $2\times10^5$ viable cells/ml into standard medium (30 ml culture) and grown at 37° C. At the peak of viable cell density (usually 7 or 8 days after passaging; viability still above 95%) cells were removed from the medium. Under these conditions and at this stage of cell growth, the maximum amounts of secreted proteases are expected to be active in the cell culture medium without release of intracellular proteases due to cell death. Also the maximum amount of secreted polypeptide of interest is expected under these conditions if the cells were transfected to express a recombinant polypeptide of interest. For obtaining conditioned medium, the cell cultures were centrifuged for 15 min at 90 g (gentle enough that cells are not releasing intracellular proteases due to centrifugation stress). After centrifugation, the supernatant was transferred and passed through a 0.22 µm filter to remove remaining cell particles from the conditioned medium.

The polypeptide of interest was added to the so obtained conditioned medium with a final concentration of 0.7 µM and incubated at 37° C. with continuous shaking at 500 rpm. The incubation time for each polypeptide of interest was previously determined by removing aliquots periodically in the wild-type sample and analyzing them using SDS-PAGE and Western Blot. A time point at which at least 50% degradation was observed in the wild-type conditioned medium was chosen for each polypeptide of interest. After incubation, all samples of the polypeptide of interest were analyzed by SDS-PAGE usually followed by Western Blot analysis to determine the amount of clipping. In the examples, different therapeutic polypeptides were used as polypeptide of interest in order to analyze clipping.

3. SDS-PAGE and Western Blot

Protein samples were diluted in Pierce Lane Marker Reducing Sample Buffer (10 mM DTT, cat. 39000) and boiled for 5 min at 95° C. About 0.1-0.6 µg protein/lane was loaded into a pre-cast 4-12% Bis-Tris Gel (Invitrogen, cat. NP0322BOX). After electrophoresis, gels were transferred on nitrocellulose membrane (Invitrogen, LC2001) using a Bio-Rad wet electro-blotting system. The polypeptide of interest was detected using an HRP-coupled specific antibody and ECL (Pierce, cat. 32109).

II. Example 1: Clipping of Different Polypeptides of Interest when Silencing Expression of Different Proteases by RNA Interference (RNAi)

First, the proteolytic cleavage site(s) of different recombinant proteins that are prone to clipping were analyzed using different techniques including CE-SDS analysis, mass spectrometry and in silico analysis (data not shown). This analysis combined with further analyses using different protease inhibitors revealed that the majority of tested proteins that are prone to clipping are cleaved by trypsin-like proteases, which is a subfamily of the serine proteases. The RNAi experiment of example 1 was set-up to demonstrate that matriptase is the key protease responsible for clipping and that silencing of the matriptase gene significantly reduces clipping while silencing of other genes encoding different proteases does not reduce clipping of the polypeptide of interest. The siRNAs were designed against the following target mRNAs expressed in CHO cells: 1. Matriptase (MT-SP1; also referred to herein as St14), 2. C1r (complement component activated C1r; also referred to as Ctra), 3. C1s (complement component C1sB; also referred to as Gm5077), 4. Plat (t-plasminogen activator) and 5. Prss35 (protease, serine, 35). These target genes encode trypsin-like proteases that are either secreted or transmembrane proteins and thus could be involved in clipping of recombinantly expressed proteins that are secreted into the cell culture medium. It was confirmed in advance that these proteins are expressed by the CHO cells. Table 2 provides an overview over the respective target genes:

TABLE 2

| Gene symbol | NCBI gene ID (CriGri_1.0 (BioProject: PRJNA72741) | NCBI mRNA Reference Sequence ID (CHO cell line) | Ensembl gene ID (*Mus musculus*) |
|---|---|---|---|
| St14 | 100755225 | XM_007644507.1; XM_007644511.1 (XM_003495842.1 was replaced by NCBI as a result of standard genome annotation processing) | ENSMUSG00000031995 |
| C1ra/C1r | 100768476 | XM_003496099.1 | ENSMUSG00000055172 |
| Gm5077 (C1s) | 100759777 | XM_007613477.1 XM_007646821 | ENSMUSG00000079343 |
| Plat | 100750775 | XM_003503315.1 | ENSMUSG00000031538 |
| Prss35 | 100761989 | XM_003495638 | ENSMUSG00000033491 |

The sense and antisense sequence of the siRNA against matriptase and the other target proteases are listed in Table 3.

TABLE 3

| Target Gene | Sense sequence of siRNA | Anti-sense sequence of siRNA |
|---|---|---|
| Matriptase (MT-SP1, also referred to as St14) | GCAAGAUCACUGU UCGCUUTT (SEQ ID NO: 6) | AAGCGAACAGUGA UCUUGCTG (SEQ ID NO: 7) |

TABLE 3 -continued

| Target Gene | Sense sequence of siRNA | Anti-sense sequence of siRNA |
|---|---|---|
| C1ra (also referred to as C1r) | GAUGUCUUUUCUC AAAAUAUU (SEQ ID NO: 8) | UAUUUUGAGAAAA GACAUCAU (SEQ ID NO: 9) |
| Gm5077 (also referred to as C1s) | CGCUGAACGUGUG AUUAUUU (SEQ ID NO: 10) | AAUAAUCACACGU UCAGCGGU (SEQ ID NO: 11) |
| Plat (siRNA sequences were designed based on internal information on the sequence of the transcript for Chinese hamster) | GAAACAAGAUGAA GACAGAUU (SEQ ID NO: 12) | UCUGUCUUCAUCU UGUUUCCC (SEQ ID NO: 13) |
| Prss35 | GGCCUUAGACUAC GACUAUU (SEQ ID NO: 14) | AUAGUCGUAGUCU AAGGCCGG (SEQ ID NO: 15) |

The detailed set-up of the experiment is described in the following.

1.1. siRNA Transfection

RNAi transfection of CHO-K1 derived cells was performed using Lipofectamine® RNAiMAX Reagent (Life Technology, cat. 13778), following the 'Reverse Transfection Protocol' of the manual MAN0001182, scaled up for 6-well plates. For each mRNA target, the two most efficient concentrations of RNAi duplex molecules were used among 100, 125 and 150 pmol: 125 and 150 pmol for MT-SP1 (St14), 125 and 150 pmol for C1r (C1ra), 100 and 125 pmol for C1s (Gm5077), 125 and 150 pmol for Plat and 100 and 125 pmol for Prss35. RNAi duplex molecules of the two selected concentrations were diluted in 1 ml Opti-MEM® (Gibco, cat. 31985-062). As RNAi negative control (siRNA negative control), the Silencer@ Negative Control No. 1 siRNA (AM4611) was used (at 125 pmol). 5 µl Lipofectamine® RNAiMAX Reagent was added in each well. 2 ml of a cell suspension with a concentration of $0.5 \times 10^6$ cells/ml were added and plates were incubated at 37° C. and 10% $CO_2$. Three days after transfection, cell density was measured, total RNA of $3 \times 10^6$ viable cells was extracted using RNeasy Plus Mini Kit (Qiagen, cat. 74134) and conditioned medium was collected from each well. To control the silencing effect on the target genes, mRNA expression was determined by real-time RT-PCR.

TABLE 4

Primers and probe sequences to determine protease mRNAs expression

| Matriptase/MT-SP1 Forward Primer Sequence | CGCTGAGTACCTGTCCTACGA (SEQ ID NO: 16) |
|---|---|
| Matriptase/MT-SP1 Reverse Primer Sequence | ACCGTCCAGTGTTACACATGAAC (SEQ ID NO: 17) |
| Matriptase/MT-SP1 Reporter 1 Sequence | CCAATGACCCATGCCC (SEQ ID NO: 18) |
| C1ra (C1r) Forward Primer Sequence | ACCTGCAAACAAGGCTACCA (SEQ ID NO: 19) |
| C1ra (C1r) Reverse Primer Sequence | TGGCAAACAGCTGTGAAGGA (SEQ ID NO: 20) |
| C1ra (C1r) Reporter 1 Sequence | CAGCACCTGGTTTCC (SEQ ID NO: 21) |
| Gm5077 (C1s) Forward Primer Sequence | TGCGAGGAGCCATATTACTACATG (SEQ ID NO: 22) |
| Gm5077 (C1s) Reverse Primer Sequence | GCAGCGCAGCGATACTC (SEQ ID NO: 23) |
| Gm5077 (C1s) Reporter 1 Sequence | CCGCCGTGTTCTTCAT (SEQ ID NO: 24) |
| Plat Forward Primer Sequence | AGCTGACATGGGAATACTGTGATG (SEQ ID NO: 25) |
| Plat Reverse Primer Sequence | CCTTTAATTCGAAACTGTGGCTGTT (SEQ ID NO: 26) |
| Plat Reporter 1 Sequence | CCGTGCTCCACCTGC (SEQ ID NO: 27) |
| Prss35 Forward Primer Sequence | AGGAGAGCACCACACAAAGAC (SEQ ID NO: 28) |
| Prss35 Reverse Primer Sequence | ACACGAGTCCACTGGAAGGA (SEQ ID NO: 29) |
| Prss35 Reporter 1 Sequence | CCCCGGACCCCTCCTG (SEQ ID NO: 30) |

The residual protease gene-expression in relation to the protease gene-expression in the siRNA negative control cells which was set as 100% was as follows: MT-SP1: 125 pmol (18.6%) and 150 pmol (18.2%), C1r (C1ra): 125 pmol (6.3%) and 150 pmol (6.7%), C1s (Gm5077): 100 pmol (11.9%) and 125 pmol (14.4%), Plat: 125 pmol (8.3%) and 150 pmol (5.1%) and Prss35: 100 pmol (18.4%) and 125 pmol (14.8%).

1.2. Spike-in Experiments in Conditioned Medium

To collect conditioned medium, 200 µl cell culture medium from the 6-well plates was centrifuged (300 g for 3 min) and the obtained supernatant was used as conditioned medium for spike-in experiments as described in Materials and Methods above. The polypeptide of interest was either a monoclonal IgG antibody (mAb) or a Fc-fusion protein. As described above, a time point at which at least 50% degradation was observed in the wild-type conditioned medium was chosen for each polypeptide of interest. The results led to an incubation time of 3 days for the Fc-fusion protein (wherein, however, degradation was already far above 50%) and to an incubation time of 7 days for the mAb. After incubation, samples of the polypeptide of interest in conditioned medium were analyzed by SDS-PAGE and Western Blot analysis to determine the amount of clipping as described in Material and Methods.

1.3. Protein Clipping: Results of Spike-in Experiments

FIG. 1 shows the Western Blot of the different analyzed polypeptides of interest after incubation as defined above, in the upper panel the mAb and in the lower panel the Fc-fusion protein.

The first lane of the Western Blot in the upper panel shows the mAb after incubation for 7 days in untreated (chemically defined) medium (the same medium was also used for culturing the cells), wherein accordingly, no clipping should occur as the cell culture medium was not in contact with cells and hence, no cellular proteases are present in said medium (positive control (+)). The mAb is displayed as a single strong protein band (marked with an arrow) and no clipping occurred.

The second lane shows the mAb sample after 7 days incubation in the conditioned medium of negative control cells ((−)), which were transfected with a siRNA negative control (no effect on gene expression). As the siRNA negative control has no effect on gene expression, the conditioned medium corresponds in essence to the conditioned medium that is obtained after incubation of the unaltered cells and hence cells which show normal target gene expression and wherein accordingly, the encoded proteases are normally expressed. As can be seen, in addition to the protein band of the intact mAb a second strong protein band appears below that represents the clipped mAb (marked with an arrow). Both protein bands have a similar intensity, thus it can be assumed that about 50% of the mAb was clipped. The same result—significant clipping—is found for the mAb incubated in the cell supernatant of cells in which C1r (C1ra), Cis (Gm5077), Plat and Prss35 were silenced by RNAi (see lanes 5 to 12). That the target genes were effectively silenced was confirmed by real-time RT-PCR. For C1r (C1ra) the strongest mRNA reduction was found with 93.7% and 93.3%. The reduction found for Plat was 91.7% and 94.9%, for Cis (Gm5077) 88.1% and 85.6% and for Prss35 81.6% and 85.2%. Accordingly, all these target genes were successfully silenced by more than 80%. Nevertheless, in all these cases the protein band of the clipped mAb had at least about the same signal intensity as the protein band of the intact mAb. Thus, as in the negative control (−), at least about 50% of the mAb was clipped. Accordingly, downregulation of these protease genes did not reduce clipping of the polypeptide of interest in the conditioned medium.

In contrast, reducing matriptase (MT-SP1) expression in the cells by RNAi (see lanes 3 and 4) considerably reduced clipping of the mAb. In both set-ups in which MT-SP1 was suppressed by 81.4% and 81.8% in comparison to the negative control (remaining MT-SP1 expression 18.6% and 18.2%), the protein band of the clipped mAb is much weaker than the protein band of the intact mAb. This demonstrates that significantly less mAb was clipped and it shows that altering a vertebrate cell to reduce functional expression of the matriptase gene, here by RNAi, significantly reduces the amount of clipping of a polypeptide of interest in the conditioned cell culture medium obtained from said cells.

Results for the Fc-fusion protein as a further example of a polypeptide of interest are shown in the lower panel of FIG. 1. In contrast to the mAb, the comparative sample "(+)" of the Fc-fusion protein contains in addition to the protein band of the intact protein a second strong band corresponding to the Fc portion alone, which is also the main clipping product (both bands are marked with an arrow). The clipped Fc portion is also found in the positive control, because the starting material (Fc-fusion protein produced in CHO cells), contains even after purification a high percentage of the clipped Fc-fusion protein. During the purification process of the Fc-protein, not all of the clipped material can be removed. Therefore, the Fc-fusion protein used in the positive control as starting material already contains significant amounts of the clipped Fc portion as impurity. In the conditioned medium of cells wherein expression of C1r (C1ra), C1s (Gm5077), Plat or Prss35 was silenced, the signal for the intact Fc-fusion protein ranges from weak (Plat) to very weak (Prss35). Accordingly, clipping of the Fc-fusion protein was very high in these cases and reached values up to almost 100% even though expression of these proteases was suppressed. Therefore, silencing of these protease genes was ineffective in order to reduce clipping. In contrast, in the conditioned medium obtained from cells in which expression of matriptase (MT-SP1) was silenced (only one siRNA concentration was used), about the same intensity of the intact protein as in the positive control (+) is found. Therefore, clipping was significantly reduced. The lane representing the siRNA negative control (−) also comprises intact protein. However, this result is a contamination of the siRNA negative control lane by the positive control which spilled over upon loading.

In summary, this RNAi experiment demonstrates that silencing expression of matriptase in the host cells results in a significant decrease in clipping of different exemplary polypeptides of interest in the conditioned medium obtained from said cells. In contrast, silencing expression of other trypsin-like proteases expressed by the host cells does not have any positive effect on clipping. Example 1 therefore supports the importance of the finding that matriptase is the major protease responsible for clipping of recombinantly expressed and secreted polypeptides of interest. Furthermore, it was found that the cells wherein matriptase was down-regulated by RNAi had the same growth characteristics as the siRNA negative control cells. Therefore, down-regulation of matriptase expression did not affect cell growth.

III. Example 2: Matriptase Gene Knock-Out (KO) in CHO Cells Leads to a Decrease in Clipping A. KO Performed with TALEN Technology Nine matriptase (MT-SP1) knock-out cell clones on the basis of CHO-K1 derived cells were generated using TALEN (Transcription Activator-Like Effector Nucleases) technology. For the knockout, matriptase exon 2 was targeted on a region located before the coding region of the transmembrane domain. Exon 2 was chosen because it covers different alternative splicing variants. Adding frameshift mutations in exon 2 has the advantage that the truncated protein will be short and will be located intracellularly and furthermore, unstable and not toxic for the cells.

2.A.1. Design/Production and Use of TALENs which are Specific for Exon 2 of Matriptase Exon 2 of matriptase and the flanking introns were sequenced in the CHO-K1 derived parental cell line (see FIG. 2, SEQ ID NO: 31).

Two truncated TAL FokI targeting matriptase exon 2 were designed. Each TALEN is targeting and binding to 19 nucleotides on either the 5' (on the forward) or the 3' (on the reverse) DNA strand, respectively. The two binding sites are separated by the sixteen nucleotides of the cutting site. Each designed TAL was synthetized and cloned in Gateway® entry vector and subcloned in a pEXP3-DEST_A302 destination vector. Product description and methods are available from Life Technology/GeneArt. Plasmids coding for the 5' (left) or the 3' (right) strand-recognizing TALEN (subcloned in the backbone vector pEXP3-DEST) were produced. pEXP3-DEST contains a T7 promoter upstream of the TALEN coding sequence, allowing in vitro transcription (IVT) of mRNA coding for TAL-FokI.

2.A.2. In-Vitro Transcription of the TALEN Vectors

TALEN mRNA was produced by in-vitro transcription (IVT) of the TALEN vectors. TALEN vectors were previously linearized with HindIII restriction enzyme (Roche, cat. 10656321001) and purified using isopropanol followed by 70% ethanol precipitations. mRNA was generated using procedures known by the person skilled in the art. Capped IVT product was purified with NH$_4$—Ac precipitation and generated mRNA (containing polyA tail and five-prime cap) was purified using the Qiagen RNeasy Micro kit (cat. 74004).

2.A.3. Transfection of TALEN mRNA

Parental CHO-K1 cells in exponential growth phase with viability over 95% were used for transfection. Electroporation (nucleofection) was performed using the Amaxa™, Nucleofector™ Technology according to the instructions of the manufacturer (Lonza). The transfected cells were expanded at day 4 after transfection and single cells separated at day 7 in 30×96-well plates. Monoclonality and confluence were controlled with the CloneSelect™ Imager (Genetix).

2.A.4. Cel-I-Assay and Screening Strategy

The Cel-I-assay was performed according to the manual of SAFC Biosciences. The Cel-I-assay is a standard assay in order to determine the cutting efficiency. In brief, 3 days after transfection genomic DNA was isolated from the cells and a PCR was performed using the following primers:

```
                                              (SEQ ID NO: 32)
        Fwd: tttttttgcccagtcctggtt (SEQ ID NO: 33)
        Rev: ccctttggtctgtcctctga
```

The amplification product was denatured and allowed to renature. Then, nuclease S and nuclease S enhancer were added and incubated. The digested product was analyzed. Two smaller bands were present indicating TALEN activity within that region of the genome and therefore, supporting that cells wherein the matriptase gene is altered by mutation were present in the analyzed cell pools. From the most positive cell pools (stronger intensity of the two smaller bands), single cells were sorted in 96 well plates.

Genomic DNA (gDNA) was extracted from each clone in 96 well plates using the Extract-N-Amp™ Blood PCR Kits (cat. XNAB2R, Sigma). The gDNA extracts were used to screen for mutated clones, in a 'CutSite PCR' assay using the Reverse Primer (Rev) shown above (SEQ ID NO: 33) in combination with a primer binding on the cutting site (referred to as Cut. Primer) which had the following sequence:

```
                                              (SEQ ID NO: 34)
        Cut. Primer: GTGGAGTTTCTGCCTGTGAA
```

If in the cutting site region a mutation occurred due to the activities of the TALENs, the Cut. Primer will not bind resulting in that no PCR product is obtained. Clones with no PCR product were analysed via sequencing to determine the introduced mutation. Alternatively or additionally, the Surveyor Mutation Detection assay (Transgenomics, cat. 706025) using the Forward (Fwd) and Reverse (Rev) primers shown above was performed. Clones with mutations were transferred in 125 ml shake-flasks and sequenced. In said screening assays clone Δ7/Δ15 was identified. Furthermore, after the first round of transfection and screening using the Cel-1 assay, one clone with the genotype wt/Δ4 was generated, which had a frameshift mutation in one matriptase allele.

To obtain knock-out clones which comprise frameshift mutations in both alleles, two TALEN mRNA transfection and cloning rounds were performed. To obtain knock-out clones with frameshift mutations in both alleles of MT-SP1, the clone with the genotype wt/Δ4 was used in a second TALEN mRNA transfection—cloning round as described above to generate frameshift mutations also in the second allele. In total, nine matriptase knock-out clones (KO-1 to KO-9) containing frameshift mutations in both alleles were generated. The genotypes of the nine clones are disclosed in Table 5. The MT-SP1 exon 2 sequences referring to the wildtype and these mutations are shown in Table 6. Partial sequences of the MT-SP1 product resulting from the mutations are shown in Table 7. The amino acids encoded by exon 2 are highlighted in bold.

According to Table 5 there are four clones, KO-1, KO-4 and KO-7 and KO-9, with the genotype Δ4/Δ4. The matriptase genotype of these clones is identical. KO-1, KO-4 and KO-7 are derived from the same TALEN re-transfected pool, KO-9 is derived from a different one. FISH analysis of clones showed that there are some differences in the karyogram of KO-1, KO-4 and KO-7. Thus, it is assumed that they are not derived from the same mother cell.

A frameshift mutation is inserted into both alleles of the matriptase gene in all clones KO-1 to KO-9. Furthermore, mutated clone Δ7/Δ15 was obtained which has the genotype Δ7/Δ15 and has a frameshift mutation in only one allele (Δ7). In the second allele, the mutation Δ15, a deletion of 15 base pairs, results in the deletion of five amino acids in the short intracellular domain of matriptase. However, no frameshift occurs due to the Δ15 deletion. The affected domain does not seem to be necessary for the catalytic function, as it remains attached to the membrane when the extracellular part comprising the catalytic protease domain is shed. Therefore, it is assumed that matriptase expressed from the Δ15 allele is still catalytically active. Therefore, in the cell clone Δ7/Δ15, functional expression of matriptase is reduced, but not abolished. It is further assumed that approx. half of the remaining mRNA expressed by said clone contains the frameshift mutation.

TABLE 5

Mutations in exon 2 of both alleles of the matriptase gene

| clone # | Genotype |
| --- | --- |
| KO-1 | Δ4/Δ4 |
| KO-2 | Δ4/Δ4' |
| KO-3 | Δ4/Δ17 |
| KO-4 | Δ4/Δ4 |
| KO-5 | Δ4/Δ14 |
| KO-6 | Δ4/Δ4' |
| KO-7 | Δ4/Δ4 |
| KO-8 | Δ4/Δ11 |
| KO-9 | Δ4/Δ4 |
| Δ7/Δ15 | Δ7/Δ15 |

TABLE 6

Matriptase gene sequences encoding exon 2 from CHO-K1 derived WT and the different KO clones.

```
WT          aacatgaatggctttgaggagggtgtggagtttctgcctgtgaataatgccaagaaagtggagaagcg
            aggcccccggcgctgtgtggtgcttgtggtcctgctggtcagtttcctcttttctct-
            cactcgtggctggcttcc
            tggtgtggcacttcctct (SEQ ID NO: 35)
```

TABLE 6 -continued

Matriptase gene sequences encoding exon 2 from CHO-K1 derived WT and the different KO clones.

| | |
|---|---|
| Δ4 | aacatgaatggctttgaggagggtgtggagtt(Δtctg)cctgtgaataatgccaagaaagtggagaa gcgaggcccccggcgctgtgtggtgcttgtggtcctgctggtcagtttcctctttctctcactcgtggctggc ttcctggtgtggcacttcctct (SEQ ID NO: 36) |
| Δ4' KO-2 nucleotide exchange (c/t) | aacatgaatggctttgaggagggtgtggagtt(Δtctg)tctgtgaataatgccaagaaagtggagaa gcgaggcccccggcgctgtgtggtgcttgtggtcctgctggtcagtttcctctttctctcactcgtggctggc ttcctggtgtggcacttcctct (SEQ ID NO: 37) |
| Δ17 | aacatgaatggctttgaggagggtg(Δtggagtttctgcctgt#)aataatgccaagaaagtggag aagcgaggcccccggcgctgtgtggtgcttgtggtcctgctggtcagtttcctctttctctcactcgtggctg gcttcctggtgtggcacttcctct (SEQ ID NO: 38) #(SEQ ID NO: 39) |
| Δ14 | aacatgaatggctttgaggagggtgtgga(Δgtttctgcctga#)ataatgccaagaaagtggag aagcgaggcccccggcgctgtgtggtgcttgtggtcctgctggtcagtttcctctttctctcactcgtggctg gcttcctggtgtggcacttcctct (SEQ ID NO: 40) #(SEQ ID NO: 41) |
| Δ4' KO-6 nucleotide exchange (t/g) | aacatgaatggctttgaggagggtgtggagg(Δtctg)cctgtgaataatgccaagaaagtggaga agcgaggcccccggcgctgtgtggtgcttgtggtcctgctggtcagtttcctctttctctcactcgtggctgg cttcctggtgtggcacttcctct (SEQ ID NO: 42) |
| Δ11 | aacatgaatggctttgaggagggtgtggagt(Δttctgcctgtg#)aataatgccaagaaagtggaga agcgaggcccccggcgctgtgtggtgcttgtggtcctgctggtcagtttcctctttctctcactcgtggctgg cttcctggtgtggcacttcctct (SEQ ID NO: 43) #(SEQ ID NO: 44) |
| Δ7 | aacatgaatggctttgaggagggtgtgg(Δagtttct)gcctgtgaataatgccaagaaagtggagaa gcgaggcccccggcgctgtgtggtgcttgtggtcctgctggtcagtttcctctttctctcactcgtggctggc ttcctggtgtggcacttcctct (SEQ ID NO: 45) |
| Δ15 | aacatgaatggctttgaggagggtgtg(Δgagtttctgcctgtg#)aataatgccaagaaagtggag aagcgaggcccccggcgctgtgtggtgcttgtggtcctgctggtcagtttcctctttctctcactcgtggctg gcttcctggtgtggcacttcctct (SEQ ID NO: 46) #(SEQ ID NO: 47) |

Δ indicates a deletion.
The number behind the Δ indicates how many nucleotides were deleted.
In parentheses and marked in bold, the deleted nucleotides are shown.

TABLE 7

Partial matriptase amino acid sequences of CH WT and KO clones including exons 1, 2 and 3 with exon 2 amino acids in bold.

| | |
|---|---|
| WT | mgsnrgrkaggsskdfgarlkyssglenmngfeegveflpvnnakkvekrgprrcvvlv vllvsflflslvagflvwhflysnvriqkvfnghlrvtnenfldayensnstefkd- lanqvkeal... exon 4 (SEQ ID NO: 48) |
| Δ4 | mgsnrgrkaggsskdfgarlkyssgle**nmngfeegvefl\*imprkwrseapgavwclw scwsvssfshswlaswcgtss**tqmfgskrssmvi\*gsqmrtfwmpmrtqtpqssktwpt r\* (SEQ ID NO: 49-51) |
| Δ4' KO-2 | mgsnrgrkaggsskdfgarlkyssgle**nmngfeegvefl\*imprkwrseapgavwclw scwsvssfshswlaswcgtss**tqmfgskrssmvi\*gsqmrtfwmpmrtqtpqssktwpt r\*rkr\* (SEQ ID NO: 52-54) |
| Δ17 | mgsnrgrkaggsskdfgarlkyssgle**nmngfeege\*cqesgearppalcgacgpagq fplsltrgwlpgvalpl**lkcsdpkglqwsseghk\*elsgcl\*elklhrvqrpgqpgegsaeavv q\* (SEQ ID NO: 55-58) |
| Δ14 | mgsnrgrkaggsskdfgarlkyssgle**nmngfeegve\*cqesgearppalcgacgpag qfplsltrgwlpgvalpl**lkcsdpkglqwsseghk\*elsgcl\*elklhrvqrpgqpgegsaeav vq\* (SEQ ID NO: 59-62) |
| Δ4' KO-6 | mgsnrgrkaggsskdfgarlkyssgle**nmngfeegvecl\*imprkwrseapgavwclw scwsvssfshswlaswcgtss**tqmfgskrssmvi\*gsqmrtfwmpmrtqtpqssktwpt r\*rkr\* (SEQ ID NO: 63-65) |
| Δ11 | mgsnrgrkaggsskdfgarlkyssgle**nmngfeegve\*\*cqesgearppalcgacgpa gqfplsltrgwlpgvalpl**lkcsdpkglqwsseghk\*elsgcl\*elklhrvqrpgqpgegsae avvq\* (SEQ ID NO: 66-69) |

A star \* represents a stop codon in Table 7.

2.A.5. Matripase mRNA Expression

In order to test the effect of the introduced mutations on matriptase expression quantitative reverse transcription real-time PCR (qRT-PCR) was performed. Matriptase mRNA expression measured in the individual clones by qRT-PCR was compared to the mRNA expression in a wild-type CHO-K1 derived cell. The result of this experiment is shown in FIG. 3. According to FIG. 3, in the cell clones with mutated matriptase, mRNA is only expressed in the range of 5 to 40% compared to the wild-type. This result suggests that expression of the mutated matriptase is reduced. Thus less (non-functional) matriptase protein is expressed by the cells. Also cell clone Δ7/Δ15 shows only low matriptase mRNA expression in the cells.

2.A.6. Spike-in Experiments with Cell Supernatant from the Nine Matriptase (MT-SP1) Knockout Clones To evaluate the effect of the matriptase knock-out, spike-in experiments were performed with five different polypeptides of interest, which are prone to clipping. Conditioned medium of cell cultures from the CHO knockout clones was obtained according to the protocol described under Material and Methods. For the spike-in experiments, the polypeptide of interest was added to the conditioned medium with a final concentration of 0.7 µM and incubated at 37° C. with continuous shaking at 500 rpm. The incubation time was dependent on the type of polypeptide of interest tested. After incubation, samples of the polypeptide of interest in conditioned medium were analyzed by SDS page and Western Blot analysis as described under Material and Methods.

Figure 4:
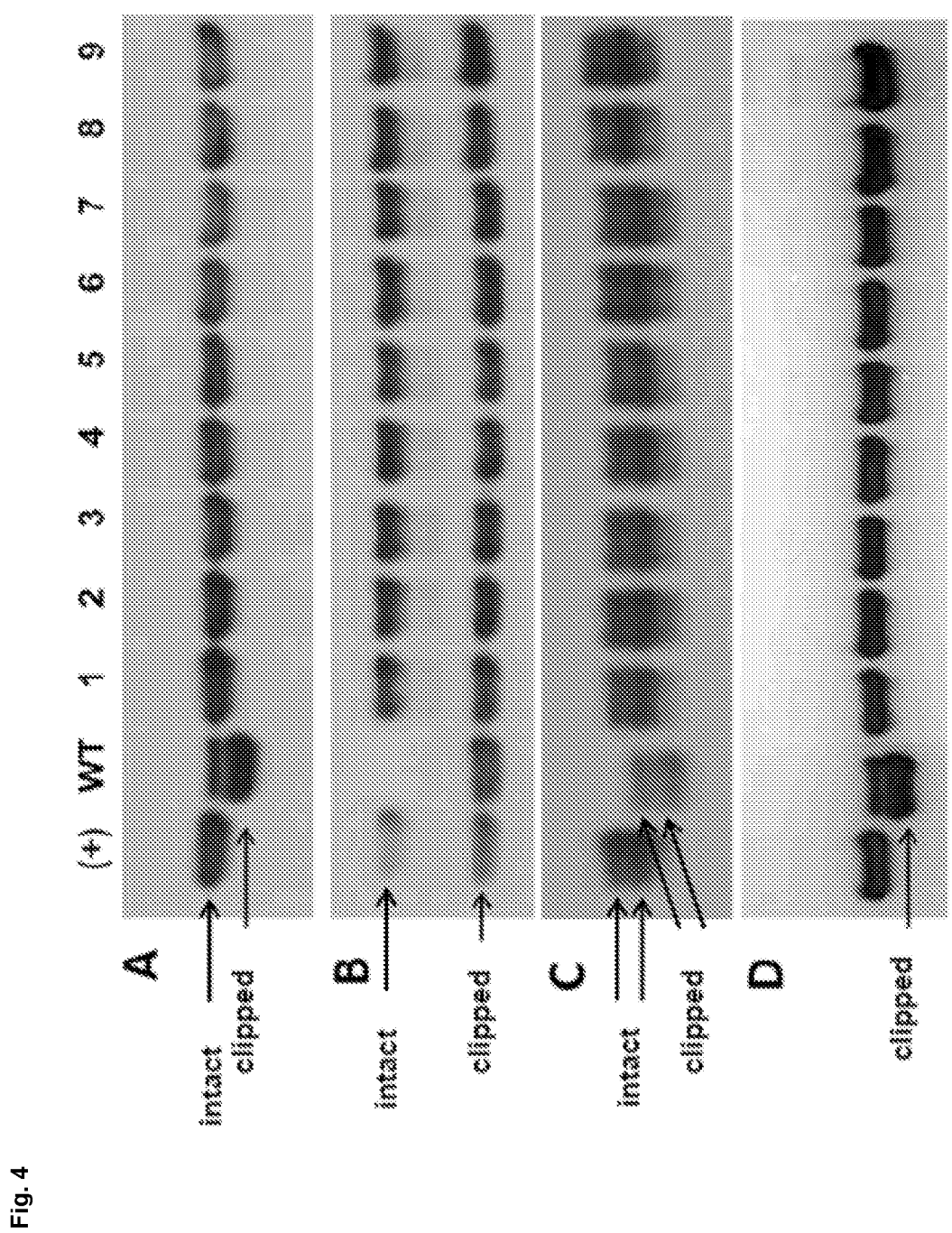
FIG. 4 shows a Western Blot of three different polypeptides of interest that are prone to clipping incubated in the cell culture medium supernatant of wild-type CHO-K1 cells (WT) and a variety of different CHO-K1 derived cell clones in which matriptase was knocked out by different mutations (see Example 2, in particular Table 5). The polypeptides of interest (concentration 0.7 μM each) were incubated in conditioned medium obtained from wildtype CHO-K1 cells (WT), the knock-out clones KO-1 to KO-9 shown in Table 5 (indicated in FIG. 4 by the numbers 1 to 9, respectively) or a chemically defined medium that was not in contact with cells (+). The polypeptide of interest in FIG. 4A is an IgG (mAb) and the incubation time was 48 h. The polypeptide of interest in FIG. 4B is a Fc-fusion protein, the incubation time was 24 h. The polypeptide of interest in FIG. 4C is a further recombinant protein with two glycovariants, the incubation time was 1 h. Both glycovariants were clipped in conditioned medium obtained from wildtype CHO-K1 cells (WT). The intact and the clipped proteins are indicated by the arrows.

FIG. 4A shows the Western Blot analysis of a spike-in experiment with a monoclonal IgG antibody (mAb) as polypeptide of interest. As reference control, the first lane from the left of the Western Blot (indicated by "(+)") shows the mAb after incubation in chemically defined medium (the same culture medium was also used for obtaining the conditioned medium). No clipping of the product is detected; the intact protein is marked with an arrow. The second lane (WT) shows the monoclonal antibody after 48 h of incubation in conditioned medium obtained from CHO-K1 derived cells which normally express matriptase. Here, a second strong band is detected, representing the clipped antibody (marked by an arrow). As the protein band of the clipped antibody is stronger than the protein band of the intact protein, more than 50% of the protein is clipped. In contrast, after incubation of the monoclonal antibody in the conditioned medium obtained from the nine knockout cell lines KO-1 to KO-9 (1 to 9 in FIG. 4), respectively, no clipped product is detected. Therefore, a knock-out of the matriptase gene in the vertebrate host cell is a significant improvement, because clipping of the mAb in the cell culture medium could be efficiently prevented.

The results of a corresponding spike-in experiment with an Fc-fusion protein are shown in FIG. 4B. The incubation time was 24 h. In contrast to the monoclonal antibody, already the positive control in chemical defined medium (+) contained a large portion of clipped protein (marked with an arrow). This is, because the Fc-fusion protein that was added as polypeptide of interest was produced in CHO cells and is heavily clipped in the culture medium from which it is harvested. Not all clipped protein could be removed during the purification process so that the starting material already contained some clipped protein contamination. While in the experiments with the matriptase knockout clones (1 to 9), the amounts of intact protein and clipped protein are comparable to the starting material incubated in the positive control (+), incubation in the conditioned medium of the unaltered CHO-K1 derived wildtype cells (WT) completely abolished and hence degraded the intact protein. Thus, basically 100% clipping was observed in the conditioned medium from cells which were not altered to impair the function of matriptase.

A comparable result is found for a further recombinant therapeutic protein that was incubated in the conditioned media for 1 h (FIG. 4C). Two glycovariants of the protein are present. Again, in the conditioned medium of the wildtype CHO-K1 cells (WT) more than 50% of the both protein glycovariants are clipped (marked by arrows), while incubation in the conditioned media of the KO-1 to KO-9 cells (1 to 9), wherein the function of the endogenous protease matriptase is impaired due to the gene knock-out, preserved the state of the intact protein as observed after incubation in a chemical defined medium (positive control (+)).

The KO clones were also analysed over months in order to analyse whether prevention, respectively reduction of clipping is a stable characteristic of the altered vertebrate cells in which the matriptase gene was knocked out. Accordingly, the spike-in experiment with the mAb was repeated with conditioned medium obtained from the matriptase knock-out cell clones which had been cultivated for 3 month. The result of the experiment, again compared with conditioned medium from CHO wildtype cell as negative control "(WT)" and chemically defined medium as positive control "(+)", is shown in FIG. 4D. The Western Blot reveals the exact same protein band pattern as the seen in FIG. 4A. The same result was also seen after 3 month for the Fc-fusion protein (data not shown). Hence, it was confirmed that with the KO clones, no clipping appeared after several months. Furthermore, it was found that the KO cell lines grew well and cell growth even improved over 3 month culture.

Figure 5:
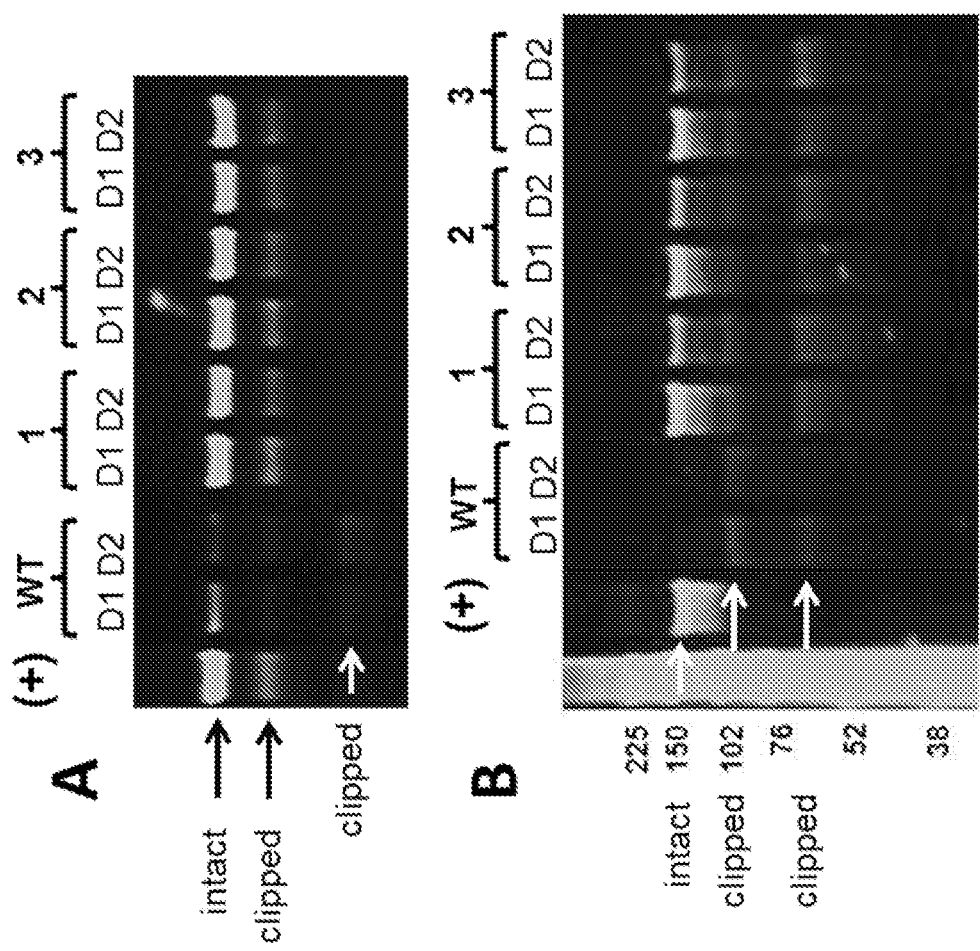
FIGS. 5A and B show Western Blots of two different viral glycoproteins (polypeptides of interest) that are prone to clipping. The polypeptides of interest were incubated in conditioned medium obtained from a CHO-K1 derived cell line which expresses matriptase (WT) and different cell clones in which matriptase was knocked out (KO-1 to KO-3). The polypeptides of interest were incubated in a concentration of 0.7 μM in conditioned medium obtained from wildtype cells (WT), conditioned medium from the knock-out clones KO-1 to KO-3 shown in Table 5 (indicated by the numbers 1 to 3, respectively) or a chemically defined culture medium that was not in contact with cells (+). D1 indicates an incubation time of 24 h and D2 an incubation time of 48 h. Intact and clipped proteins are indicated by arrows (white and black arrows). The numbers on the left side of the Western Blot in FIG. 5B represent the molecular weight in kDa as determined. The results again demonstrate that clipping is significantly reduced in the conditioned medium obtained from matriptase KO clones.

The results of the spike-in experiments with two glycosylated viral proteins using conditioned medium of the matriptase knock-out clones KO-1 to KO-3 (1-3) are shown in FIG. 5 after 24 h (D1) and 48 h of incubation (D2). In the first lane of the Western Blot (FIG. 5A) representing the protein after incubation in chemical defined medium (+), two protein bands are visible. The upper band represents the intact protein, the lower band a clipped version of the protein which makes up about 5% of the total protein in the sample. In the conditioned medium of CHO-K1 wildtype (WT lanes) a strongly reduced amount of intact protein is present after 24 h (D1) of incubation. After 48 h (D2) the protein band is almost invisible, i.e. almost all protein was clipped. In addition, the protein band of the clipped protein completely disappeared suggesting that the protein was further degraded. In contrast, no difference in the protein band pattern is found for proteins incubated for 24 h or 48 h in the conditioned media of the matriptase knockout clones KO-1 to KO-3 (see 1 to 3). Accordingly, with conditioned medium obtained from the matriptase knock-out cell lines, no or significantly reduced proteolytic degradation of the therapeutic proteins was detected. The second viral protein shows a comparable result (FIG. 5B). Here, the intact protein is represented by the single protein band shown in lane "(+)". Already after 24 h of incubation in conditioned medium of CHO-K1 derived wildtype cells (WT, D1) almost no trace of the intact protein can be detected. Instead, two lower protein bands appear, representing clipped versions of the protein. These protein bands are also seen in the experiment with the medium obtained from matriptase knockout clones KO-1 to KO-3. However, the majority of the viral protein is preserved with all tested knock-out clones even after 48 h of incubation.

Confirming the experiments above, spike-in experiment with five additional Fc-fusion proteins, which are prone to clipping, were performed as described above. The cell free harvest supernatant was captured by Protein A affinity liquid chromatography using 1 mL HiTrap MabSelect Sure (GE Healthcare). A residence time of 2 minutes was applied for equilibration, load and wash. For the elution a residence time of 4 minutes was applied. The eluate was titrated to pH 5 with 1 M Tris prior to sterile filtration with a Millex-GV Syringe Filter Unit (0.22 µm, PVDF, 13 mm; Millipore). The protein concentration was determined using a NanoDrop 2000 spectrophotometer (Thermo Scientific) at 280 nm wavelength. All steps were performed at room temperature. Table 8 shows the mass spectrometry analysis data. As can be seen, all tested Fc-fusion proteins were completely or almost completely clipped when expressed in the parental cells. In contrast thereto, clipping was considerably reduced when being expressed in the knock-out cell line.

TABLE 8

Clipping analysis of different Fc-fusion proteins

| Candidates | WT Clipped Fc-fusion protein [%] | KO-4 Clipped Fc-fusion protein [%] |
|---|---|---|
| Fc-fusion protein 1 | 100% | 81% |
| Fc-fusion protein 2 | 97% | 48% |
| Fc-fusion protein 3 | 98% | 63% |
| Fc-fusion protein 4 | 100% | 68% |
| Fc-fusion protein 5 | 100% | 67% |

These examples demonstrate that the altered vertebrate cells according to the present disclosure wherein the function of the endogenous protease matriptase is impaired, present or release no or reduced amounts of functional matriptase into the cell culture medium. Therefore, proteolytic degradation of the recombinant polypeptide of interest that is present in (normally secreted into) the cell culture medium is significantly reduced when using these altered cells for producing a polypeptide of interest.

2.A.7. Spike-in Experiments with Cell Supernatant from the Matriptase Mutant Clone Δ7/Δ15

To evaluate the effect of reduced functional matriptase expression, the spike-in experiments with the Fc-fusion protein and the monoclonal IgG antibody (mAb) were repeated with conditioned medium obtained from the Δ7/Δ15 clone. Conditioned medium of the cell culture was obtained according to the protocol described under Material and Methods. For the spike-in experiment, the polypeptide of interest was added to the conditioned medium with a final concentration of 0.7 µM and incubated at 37° C. with continuous shaking at 500 rpm. The Fc-fusion protein was incubated for 2 h, the mAb for 24 h. After incubation, samples of the polypeptides of interest in conditioned medium were analysed by SDS-PAGE and Western Blot analysis as described under Materials and Methods.

Figure 6:
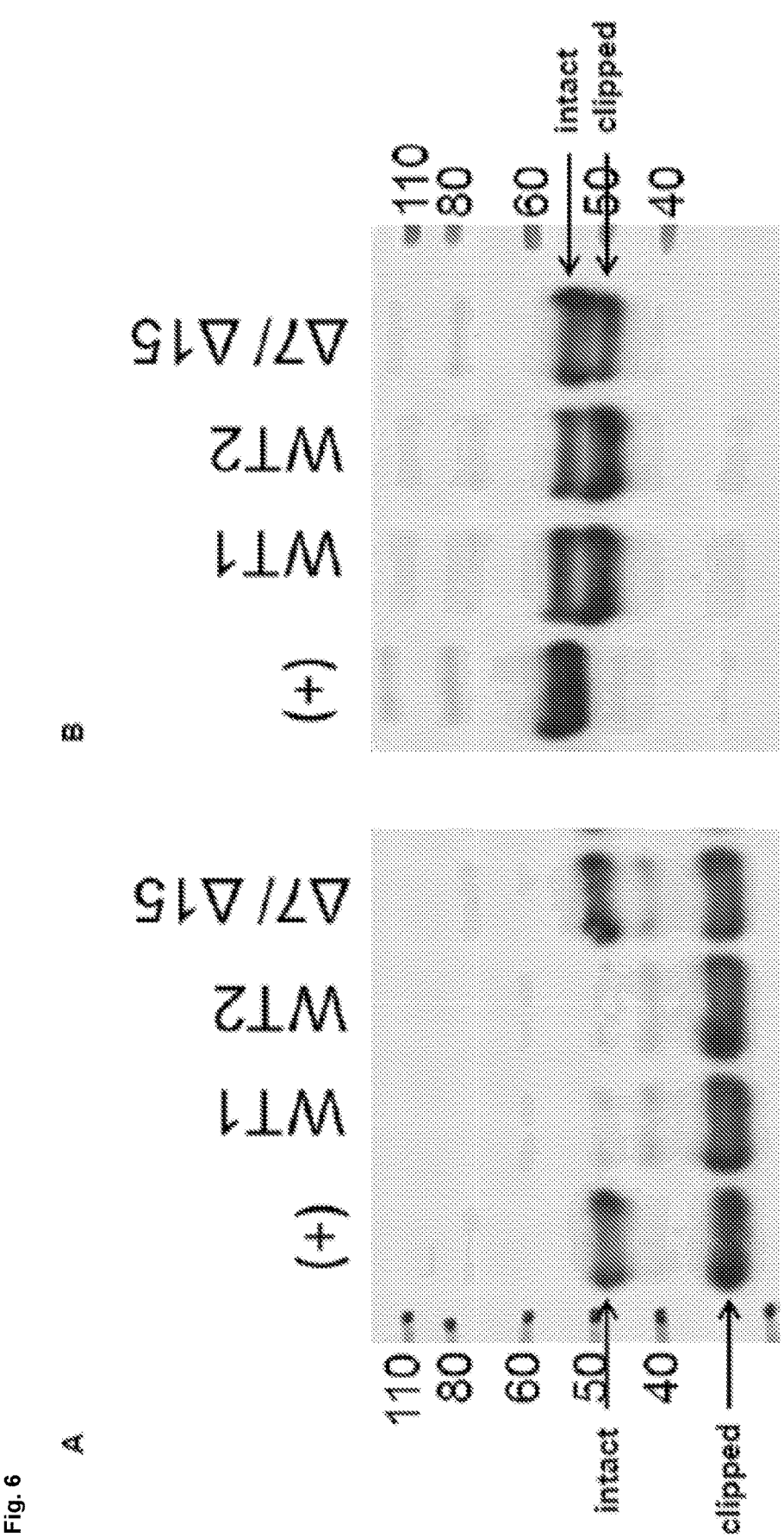
FIG. 6 shows a Western Blot of a Fc-fusion protein (FIG. 6A) and a IgG (mAb) (FIG. 6B) incubated in the cell culture medium supernatant obtained from CHO cells expressing wildtype matriptase ("WT1" and "WT2") and a CHO clone in which the matriptase was mutated ("Δ7/Δ15") so that functional expression of matriptase was reduced. A corresponding chemically defined culture medium ("(+)") that was not in contact with the cells served as positive control. The Fc-fusion protein and the mAb (concentration of 0.7 μM each) were incubated for 2 h and 24 h, respectively. The numbers at the side of the Western Blot represent the approx. molecular weight in kDa as determined on the gel. The results demonstrate that clipping is reduced in the conditioned medium obtained from the mutant cell clone Δ7/Δ15 in which functional expression of active matriptase is reduced.

The results of the spike-in experiment with the Fc-fusion protein are shown in FIG. 6A. As reference, the first lane of the Western Blot shows the Fc-fusion protein after incubation in chemically defined medium (indicated by "(+)"). The second and third lane ("WT1" and "WT2") shows the Fc-fusion protein after incubation in conditioned medium from two different CHO-K1 derived wild-type cell lines which normally express the unmodified, functional matriptase. As discussed above, the starting material contained the intact Fc-fusion protein as well as clipped Fc-fusion protein as impurity. In the protein samples derived from incubation with conditioned medium from CHO cells with wild-type matriptase ("WT1" and "WT2"), basically no intact Fc-fusion protein is observed. In contrast, incubation in conditioned medium obtained from the Δ7/Δ15 cell clone ("Δ7/Δ15") in which functional expression of matriptase is significantly reduced (for details regarding the clone see Example 2.4), clipping is significantly reduced as can be concluded from the strong protein band representing the intact Fc-fusion protein.

FIG. 6B shows the Western Blot analysis of a spike-in experiment with the IgG mAb as polypeptide of interest. As reference, the first lane of the Western Blot (indicated by "(+)") shows the mAb after incubation in chemically defined medium. One strong protein band representing the intact antibody is visible. The second and third lane ("WT1" and "WT2") shows the monoclonal antibody after incubation in conditioned medium from two different CHO-K1 derived wild-type cell lines which express the unmodified matriptase. In this second and third lane, an additional strong protein band having a lower molecular weight appears representing the clipped antibody. According to the signal strength, more than 50% of the antibody appears to be clipped. In the fourth lane ("Δ7/Δ15") showing the mAb after incubation in conditioned medium from the cell clone Δ7/Δ15, the intensities of the signals are reversed. Thus, although clipping is not completely abolished, it is strongly reduced compared to the matriptase wild-type cell clones. This result confirms that reducing functional expression of matriptase, significantly reduces clipping of the polypeptide of interest in the cell culture medium.

These experiments show that when using a cell clone wherein only one matriptase allele is knocked-out and wherein functional matriptase expression is reduced also leads to a reduced clipping of the polypeptide of interest in the cell culture medium. Thus, it can be concluded that the clipping activity is proportional to the degree of functional matriptase expression.

B. KO Performed with ZFN Technology

One ZFN (MT-SP1) knock-out cell clone on the basis of CHO parental cells was generated using ZFN (Zinc Finger Nucleases) technology. For the knockout, matriptase exon 2 was targeted on a region located before the coding region of the transmembrane domain (as described in Example 2 A).

2.B.1. Design/Production and Use of TALENs which are Specific for Exon 2 of Matriptase A pair ZFNs targeting matriptase exon 2 were designed. One ZFN is targeting and binding to 12 nucleotides, the other one is targeting 18 nucleotides. The two binding sites are separated by the five nucleotides of the cutting site.

2.B.2. In-Vitro Transcription of the TALEN Vectors

ZFN mRNA was produced by in-vitro transcription (IVT) of the ZFN vectors. mRNA was generated using procedures known by the person skilled in the art. Capped IVT product was purified with NH4-Ac precipitation and generated mRNA (containing polyA tail and five-prime cap) was purified using the Qiagen RNeasy Micro kit (cat. 74004).

2.B.3. Transfection of ZFN mRNA

Parental CHO cells in exponential growth phase with viability over 95% were used for transfection. Electroporation (nucleofection) was performed using the Amaxa™, Nucleofector™ Technology according to the instructions of the manufacturer (Lonza).

2.B.4. Cel-I-Assay and Screening Strategy

The Cel-I-assay was performed according to the manual of SAFC Biosciences and a similar screen as described in example 2A.4 was performed.

To obtain a knock-out clone which comprise frameshift mutations in both alleles, two ZFN mRNA transfection and cloning rounds were performed. One matriptase knock-out clones (KO-10) containing frameshift mutations in both alleles was generated (A13/A13).

2.B.5. Spike-in Experiments with Cell Supernatant from Matriptase (MT-SP1) Knockout Clone To evaluate the effect of the matriptase knock-out, spike-in experiments were performed with two different polypeptides of interest, which are both prone to clipping. Conditioned medium of cell cultures from the CHO knockout clones was obtained according to the protocol described under Material and Methods. For the spike-in experiments, the polypeptides of interest (one Fc-fusion protein and one recombinant therapeutic protein) was added to the conditioned medium with a final concentration of 0.7 µM and incubated at 37° C. with continuous shaking at 500 rpm. The incubation time was dependent on the type of polypeptide of interest tested. After incubation, samples of the polypeptide of interest in conditioned medium were analyzed by SDS page as described under Material and Methods.

The results are corresponding to the spike-in experiments performed with KO clones generated with TALEN technology. An Fc-fusion protein and a recombinant therapeutic protein as described in example section 2.A.6 were used. While in the experiments with the matriptase knockout clone, the amounts of intact proteins and clipped proteins are comparable to the starting material incubated in the positive control (+), incubation in the conditioned medium of the unaltered CHO-K1 derived wildtype cells (WT) completely abolished and hence degraded the intact proteins.

The KO clones were also analysed over several months in order to analyse whether prevention, respectively reduction of clipping is a stable characteristic of the altered vertebrate cells in which the matriptase gene was knocked out. Accordingly, the spike-in experiment with the Fc-fusion protein was repeated with conditioned medium obtained from the matriptase knock-out cell clones which had been cultivated for 6 months. The result of the experiment confirmed that with the KO clone, no clipping appeared even after several months. Furthermore, it was found that the KO cell line grew well and cell growth even improved over culture time.

IV. Example 3: Recombinant Proteins are Directly Cleaved by Matriptase

In order to further demonstrate that matriptase directly cleaves recombinantly expressed and secreted proteins (clipping targets), commercially available proteases were used, namely mouse MT-SP1 and human Htra1. A monoclonal IgG antibody mAb (FIG. 7A), an Fc-fusion protein (FIG. 7B) and a further recombinant protein (FIG. 7C) were incubated for 24 h, 2 h and 1 h, respectively, with the two trypsin-like proteases mouse MT-SP1 and human Htra1, which were added to the chemically defined culture medium. Coincubation was performed at 37° C. with continuous shaking at 500 rpm. The polypeptides of interest were used at a concentration of 0.7 µM each. Each polypeptide of interest was tested with decreasing amounts of the proteases MT-SP1 and Htra1: Molar ratios of protease/polypeptide of interest from left to right are 1/10, 1/100, 1/1000 for MT-SP1 and 1/3, 1/10 and 1/100 for Htra1. As controls, additional samples of the polypeptide of interest are incubated with conditioned medium from CHO-K1 wildtype derived cells as negative control (lane "(−)") and a chemically defined medium which was not in contact with cells as positive control (lane "(+)").

Figure 7:
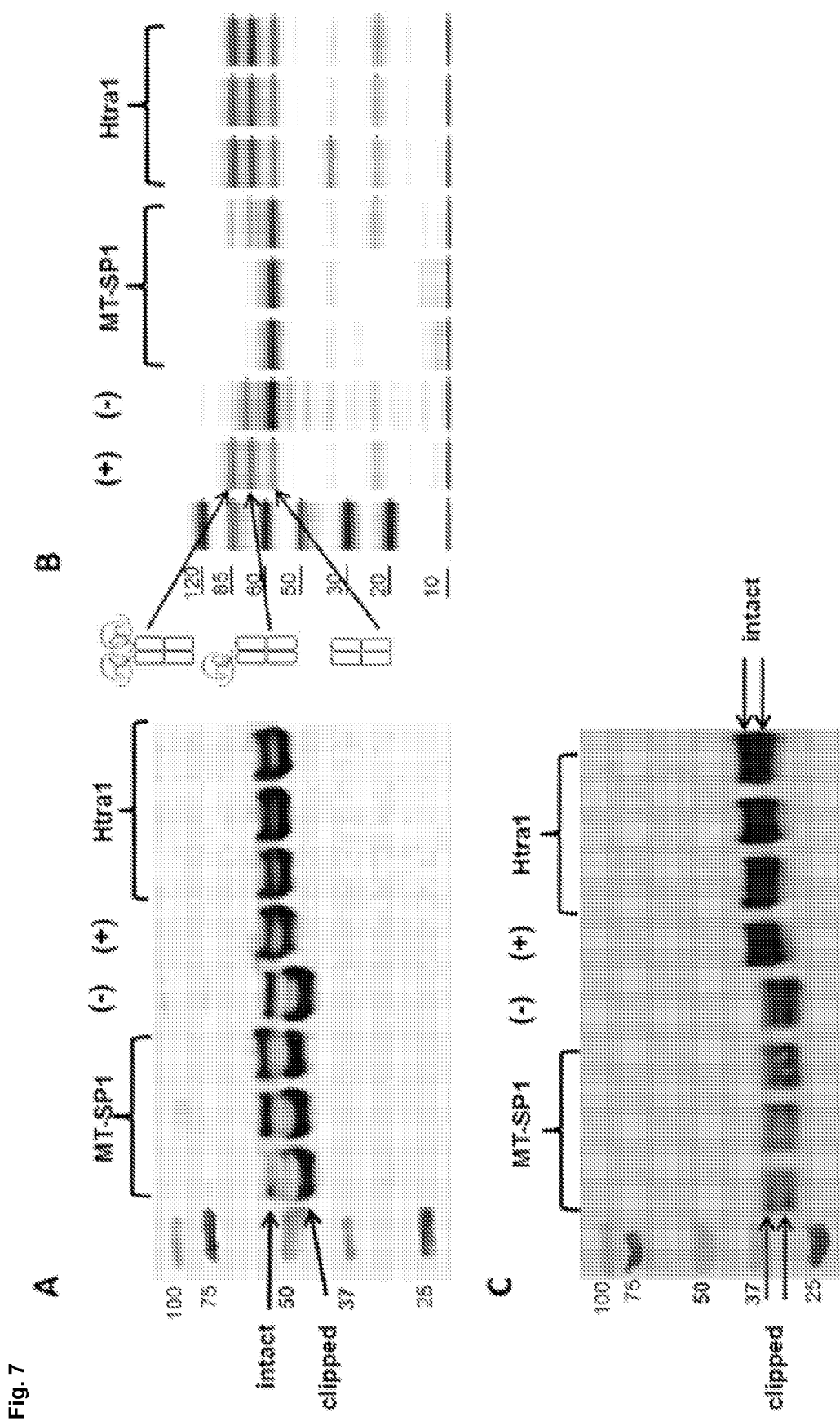
FIG. 7 shows the results of a coincubation of different polypeptides of interest with two different trypsin-like proteases, namely matriptase from mouse (MT-SP1) and human Htra1.

From the Western Blots in FIG. 7A to C it is evident that the recombinant Htra1 that was added to the cell culture medium cleaves none of the tested polypeptides of interest. Even at higher Htra1 concentrations, the protein bands look exactly like in the positive control ("(+)"). In contrast, all recombinant polypeptides of interest were significantly clipped even at the lowest concentration of MT-SP1 added. The protein band either resembled that of the negative control ("−") or was even worse. Therefore, significant degrees of clipping occurred under all conditions tested when MT-SP1 was added.

In the experiment with the Fc-fusion protein a concentration dependent effect of the protease MT-SP1 was observed (FIG. 7B). While at the lowest concentration of matriptase/MT-SP1 the protein band of the intact Fc-fusion protein at about 85 kDa is only slightly reduced in comparison to the positive control, at higher concentrations of MT-SP1 the protein band at approx. 85 kDa completely disappears. Consequently, the degree of clipping of the Fc-fusion protein correlates with the concentration of matriptase/MT-SP1 in the cell culture medium.

To determine the clipping site induced by the commercial mouse MT-SP1 used in this example, the antibody sample (mAb) with MT-SP1 concentration 1/100 was subjected to mass spectrometry. The identified clipping site was the same as when the mAb was produced by the wildtype CHO cell line. This shows that the clipping site of mouse matriptase on the mAb is the same as the clipping site of the protease responsible for clipping when producing the mAb in CHO cells. These results further confirm that matriptase is the clipping protease.

V. Example 4: Inhibition of the Matriptase Clipping Action by a Selective Matriptase Inhibitor To further confirm that clipping of the recombinant polypeptide of interest is caused by matriptase as key protease responsible for clipping, spike-in experiments were performed with a specific anti-MT-SP1 Fab fragment which specifically inhibits human matriptase/MT-SP1. The inhibitory Fab structure and binding details on human MT-SP1 are published in Farady et al., 2008 J. Mol. Biol. (2008) 380, 351-360).

The therapeutic polypeptides of interest as clipping targets were in this case a monoclonal IgG antibody (mAb) and a recombinant non-antibody glycoprotein with two glycovariants. The polypeptide of interest was added in a concentration of 0.7 µM in each case. Table 9 describes the further details of experimental set-up corresponding to the Western Blot results shown in FIG. 8 for the mAb (FIG. 8, upper panel) and the recombinant protein (FIG. 8, lower panel):

TABLE 9

| | |
|---|---|
| Lane 1 | Marker |
| Lane 2 | Chemically defined medium (+) |
| Lane 3 | Conditioned medium obtained from CHO-K1 derived wildtype cells (−) |
| Lane 4 | Chemically defined medium with 3.45 nM recombinant mouse MT-SP1 added |
| Lane 5 | Chemically defined medium with 3.45 nM recombinant mouse MT-SP1 and 1 µM anti-MT-SP1 Fab fragment added |
| Lane 6 | Chemically defined medium with 3.45 nM recombinant mouse MT-SP1 and 10 µM anti-MT-SP1 Fab fragment added |
| Lane 7 | Chemically defined medium with 3.45 nM recombinant mouse MT-SP1 and 50 µM anti-MT-SP1 Fab fragment added |
| Lane 8 | Conditioned medium obtained from CHO-K1 derived wildtype cells |

TABLE 9-continued

| | |
|---|---|
| Lane 9 | Conditioned medium obtained from CHO-K1 derived wildtype cells and 1 μM anti-MT-SP1 Fab fragment added |
| Lane 10 | Conditioned medium obtained from CHO-K1 derived wildtype cells and 10 μM anti-MT-SP1 Fab fragment added |
| Lane 11 | Conditioned medium obtained from CHO-K1 derived wildtype cells and 50 μM anti-MT-SP1 Fab fragment added |

Conditioned medium was prepared as described under Materials and Methods. The incubation time was 24 h in case of the monoclonal IgG antibody and 1 h for the recombinant non-antibody protein.

Figure 8:
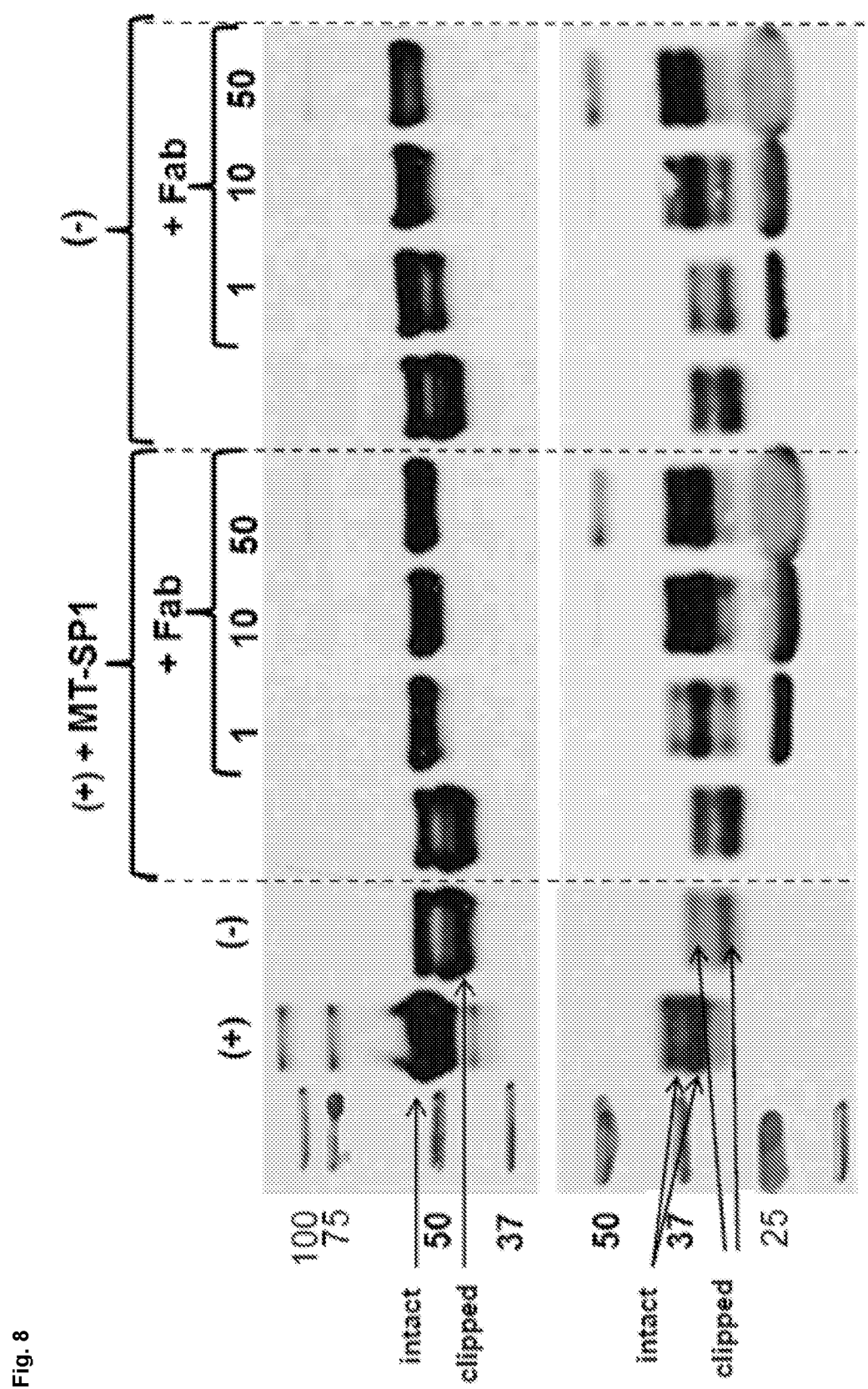
FIG. 8 shows a Western Blot analysis of two polypeptides of interest, a monoclonal IgG-antibody (upper panel, incubation time 24 h) and a recombinant protein (lower panel, incubation time 1 h). The polypeptides of interest (concentration 0.7 μM each) were incubated in either a chemically defined culture medium "(+)", in conditioned medium obtained from CHO-K1 derived wildtype cells "(−)", or in a chemically defined culture medium with recombinant matriptase from *Mus musculus* added ((+)+MT-SP1). To several samples an anti-MT-SP1 inhibitory Fab fragment was added as indicated ("+Fab"). The concentration of the Fab in the sample is shown above the lane (1 μM, 10 μM or 50 μM). Arrows indicate protein bands representing the intact or the clipped protein. The protein band at approx. 25 kD in the lanes wherein the Fab fragment was added represent the Fab fragment. The results demonstrate that addition of the anti-MT-SP1 Fab fragment (which is a selective matriptase inhibitor) to a cell culture medium in which matriptase is active reduces or even completely prevents clipping. The results further confirm that matriptase is the key protease responsible for clipping.

FIG. 8 (see upper panel) shows that a strong protein band of the intact mAb is present in the positive control (+) (see lane 2). No clipped mAb is observed. In the negative control (−) (see lanes 3 and 8), a second protein band of higher intensity appears slightly below the intact protein indicating that the monoclonal antibody is significantly clipped in the conditioned medium of CHO-K1 derived wildtype cells. The intact and the clipped mAb are marked with arrows. The same pattern as in the negative control (−) is seen in the chemically defined medium wherein mouse MT-SP1 was added (see lane 4). With respect to the recombinant non-antibody protein (see FIG. 8, lower panel), in the positive control (+) (see lane 2), a strong band is seen for the two intact protein glycovariants at about 37 kDa. Those protein bands for the intact protein glycovariants seen in the positive control disappeared in the negative control (−) and new protein bands for the clipped protein glycovariants appeared (see lanes 3 and 8).

With respect to the samples that were incubated in the presence of anti-MT-SP1 Fab, already 1 μM of the Fab was sufficient to completely abolish degradation of the mAb by the mouse MT-SP1 (FIG. 8, upper panel, lane 5). 1 μM of the anti-MT-SP1 Fab also reduced but could not completely prevent clipping of the mAb in conditioned medium (see upper panel, lane 9). Clipping of the mAb was abolished in conditioned medium at a Fab concentration of 10 μM and 50 μM (FIG. 8, upper panel, lanes 10 and 11). For the recombinant protein incubated with recombinant mouse MT-SP1 in chemically defined medium, clipping was reduced already at a concentration of 1 μM Fab (see FIG. 8, lower panel, lane 5). A further reduction of clipping was seen at 10 μM Fab and a complete stop of clipping was seen with 50 μM Fab in the chemically defined medium with recombinant mouse MT-SP1 added as well as in the conditioned medium (see FIG. 8, lower panel, lanes 6, 7 and 10 and 11). Therefore, the Fab raised against human matriptase also effectively inhibited mouse as well as hamster matriptase. However, higher concentrations were necessary to see full inhibition of the mouse and hamster matriptase. It is assumed that this is attributable to amino acid differences between the human and the mouse and hamster matriptase within the epitope binding site so that the inhibitory Fab against the human matriptase is less potent on mouse and hamster matriptase so that higher concentrations of the Fab are needed to inhibit them.

VI. Example 5: Protein Production in Matriptase Knock-Out Cell Lines

In order to confirm the results from the spike-in experiments, several polypeptide of interest were expressed in a matriptase knock-out cell clone in fed batch cultivation and the clipping of the expressed and secreted polypeptide of interest was analyzed and compared to the results obtained with a corresponding CHO wildtype cell line which endogenously expresses intact matriptase.

5.1. Transfection of the mAb Coding Vector

A CHO wild-type cell line which expresses matriptase (derived from CHO-K1) and the matriptase knock-out CHO cell clone 4 (KO-4, see Table 5) were transfected with an expression vector comprising a polynucleotide encoding a monoclonal antibody (mAb) and two selectable marker genes, namely neo and DHFR. For transfection, cells were grown to exponential phase and $5 \times 10^6$ cells were transfected with 3 μg vector DNA. Five transfection replicates were performed using the wild-type cell line and four transfection replicates were performed using the KO-4 cell line. Selection of cells stably transfected with the vector encoding the protein of interest was performed with G418 (G418 concentration 0.8 mg/ml) followed by two consecutive steps of MTX selection (500 nM and 1 μM MTX). The selection conditions were identical for all pools and both cell lines. At the end of the selection (cell viability >95%) cells were frozen. During the selection process, titers of expressed mAb in the medium were determined. The titer in the supernatant of the matriptase knock-out cells was compared to the titer of the CHO wild-type cells. The results demonstrated that the matriptase knockout has no negative effect on the production capacity of the cells but even had a tendency to increase the titer.

5.2. Fed Batch Production Procedure

For fed batch production, all four pools of the matriptase knock-out clone KO-4 and three CHO wild-type cell line pools with the highest antibody titer were selected. The frozen cells of the seven pools were thawed at the same time and passaged once before inoculation into the individual fed batch reactors.

The cells were cultivated in fed batch shakers containing a chemical defined medium enriched in amino acids, vitamins and trace elements (Fed Batch Medium). The fed batch cultivation was performed at temperature of 37° C. and shaking. During the fed batch cultivation, a feed containing glucose, and amino acids (Fed Batch Feed) was regularly added along the process. During the fed batch cultivation process, samples of the fed batch culture material were regularly collected to determine the viable cell density (vcd) using a Vi-Cell cell viability analyzer (Beckman Coulter) and to determine the protein titers in the cell culture medium. At the end of the fedbatch (day 13 or 14), the cultivation process was stopped. The conditioned medium from the shake-flask (100 ml culture) was harvested and filtered using a 0.22 μm Steriflip filter. The monoclonal antibody was purified from the filtered conditioned medium using protein A affinity liquid chromatography (Protein A Mini Columns, Proteus, cat. PUR008). The purification was performed using the vendor's protocol. The protein concentration of the samples after protein A purification was determined using NanoDrop™ system (Thermo Scientific) according to the vendors protocol. Analysis of the fed batch cultures revealed that over the 14 days cultivation period, the titer of expressed mAb in the culture medium of the KO-4 pools was similar or even higher than in the culture medium of CHO wild-type cell pools. Moreover, the cell viability was similar or even higher for the KO-4 cell pools. The KO cells also grew at similar or even better cell densities. These results indicate that the matriptase knock-out does not negatively influence the protein expression rate and might even enhance it. In addition cell growth was not negatively affected but may even be improved.

5.3. Clipping Analysis

For clipping analysis two parallel approaches were used: Microchip electrophoresis (ME)—SDS and mass spectrometry.

Microchip Electrophoresis

5 μL of the purified protein is used for sample preparation. Depending on the concentration of the samples, the amount of protein is different. For the sample preparation of reducing microchip assay, 5 μL is mixed with 35 μL of reducing sample buffer. Then the mixed solution is incubated in the heat block for 15 min at 70° C. After cooling it down, 70 μL of MilliQ water was added to a final volume of 110 μL. The LabChip® GX II instrument from PerkinElmer was used as system. The used protocol is a revised version from the vendor's protocol. The main difference is the ratio of sample/reducing sample buffer, which is 1:7 in the present protocol for better denaturation instead of 1:3.5 in the vendor's protocol.

Figure 9:
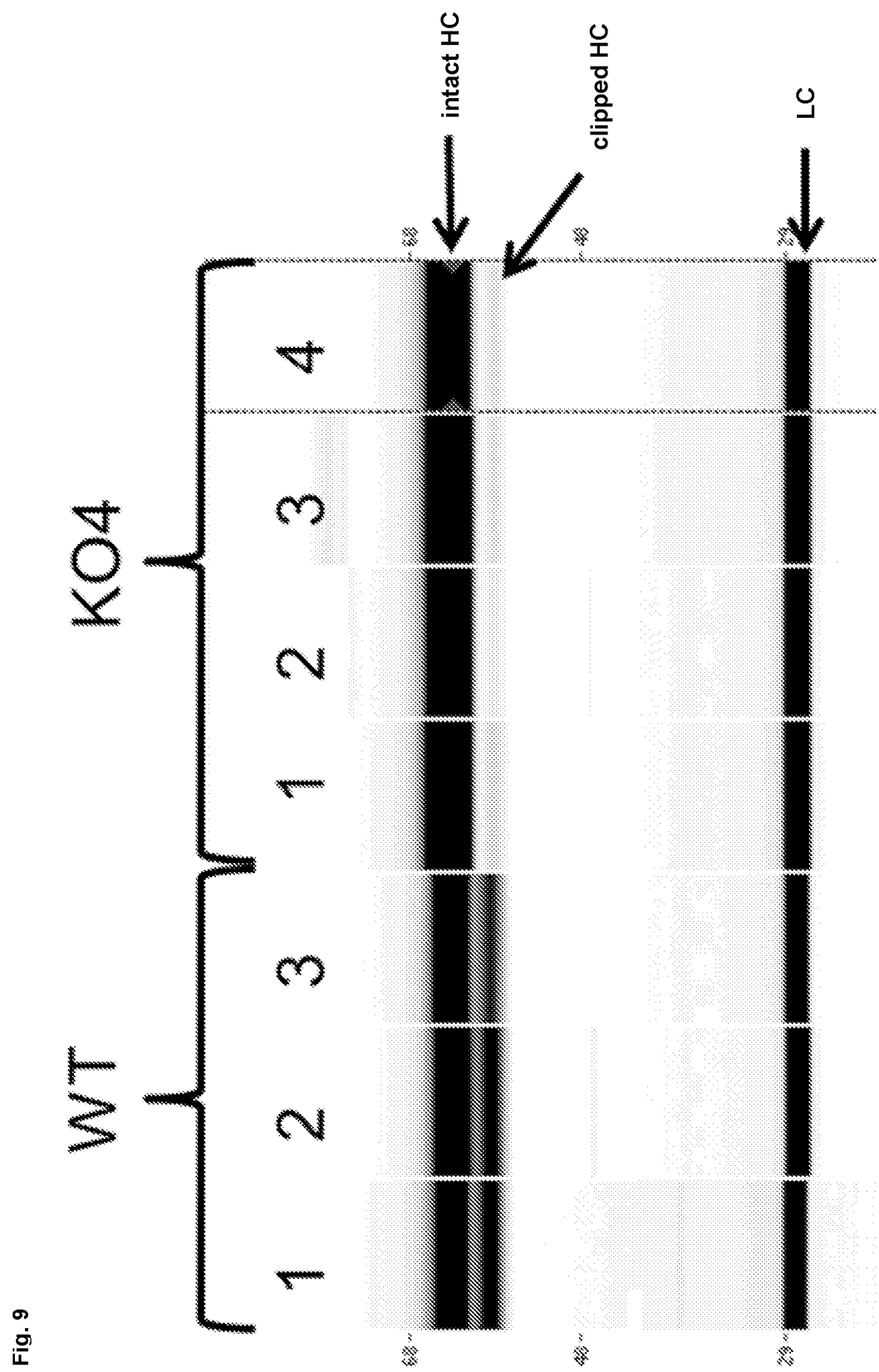
FIG. 9 shows the result of a microchip capillary electrophoresis (Caliper LabChip®). A recombinant mAb was expressed in CHO-K1 derived wild-type cells (WT) and in matriptase knock-out cells (KO-4, see also Table 5) and was purified using affinity chromatography (protein A). The numbers above the lanes present different mAb production cell pools obtained from parallel transfection and selection processes. In each lane three protein bands are visible as indicated by arrows. The upper protein band represents the intact mAb heavy chain, the second band (directly below the first) represents the clipped antibody heavy chain and the band at the bottom represents the light chain of the mAb. The results show that clipping is significantly reduced when expressing a polypeptide of interest in matriptase knock-out cells.

FIG. 9 shows the result of the microchip electrophoresis. The first three lanes from the left (identified as WT 1, 2 and 3) represent the protein sample composition of the protein A purified cell culture from the three productions with CHO wild-type cell pools. In each sample the same protein band pattern is observed. A broad protein band representing the intact heavy chain (HC) of the monoclonal antibody was observed (the size from the Labchip assay is not accurate and usually overestimated). Directly below this protein band a second thinner protein band representing the clipped heavy chain is observed. The clipped HC species co-migrates with non-glycosylated HC. In addition, a third protein band representing the light chain is observed at about 29 kDa. In the protein samples of the monoclonal antibody produced in the matriptase knock-out cell pools (identified as KO-4 1, 2, 3, and 4), both, the protein band of the intact heavy chain and of the light chain, are at least comparable if not stronger compared to the protein bands found in the samples produced by the CHO wild-type cell lines. However, the band of the clipped heavy chain identified by the second arrow from the top in FIG. 9 is hardly visible in all four antibody samples K04-1, K04-2, K04-3 and K04-4. This demonstrates that clipping of the mAb is almost abolished when being produced in matriptase knock-out cell lines.

In order to quantify the result the intensity of the protein bands of clipped antibody heavy chain and intact antibody heavy chain was determined and from this the percentage of clipping was calculated. The result of this analysis is summarized in Table 10. It shows that the amount of clipping of the monoclonal antibody is drastically reduced when using the matriptase knock-out clone as production cell line. According to the analysis, on average 16.1% of the monoclonal antibody heavy chain produced by the three CHO wild-type cell pools was clipped. In contrast, only 1% or less of clipping occurred on average for the mAb HC produced in the four matriptase knock-out fed batch cultivations. Due to the comigration of the non-glycosylated HC, exact values cannot be determined based on LabChip® analysis.

TABLE 10

Clipping Analysis based on protein band intensity

| Sample | Clipped mAb Heavy Chain [%] |
|---|---|
| WT 1 | 20.2 |
| WT 2 | 15.6 |
| WT 3 | 12.4 |
| KO-4 1 | 0.9 |
| KO-4 2 | 0.9 |
| KO-4 3 | 1.0 |
| KO-4 4 | 0.7 |

Thus, using microchip electrophoresis, merely 1% or less clipping is detected in mAb expressed by matriptase KO cells while 12% to 20% clipping is detected in WT cells expressing the same mAb (clipping detected in HC).

Mass Spectrometry Analysis

Samples were deglycosylated and reduced prior to mass spectrometry analysis. From each of the seven protein A purified protein samples an aliquot with a total protein of 50 μg was incubated overnight at 37° C. with 1.25 μl PNGase F at a concentration of 0.3 mg/ml in 50 mM Tris/HCl pH 7.5. The final concentration of the sample was about 0.5 mg/ml. After deglycosylation 88 μl of the PNGase F digested samples were reduced by adding 112 μl reducing buffer (8M GuHCl, 10 μl 1M Tris/HCl pH 7.5 and 2 μl 1M DTT) and incubation for one hour at 37° C. The reduction was quenched by addition of 2 μl of 10% trifluoroacetic acid.

The so obtained samples with a total volume of 202 μl and a concentration of about 0.22 mg/ml protein was then used for analysis by combined liquid chromatography and mass spectroscopy. The LC/MS instrument was Waters Synapt G2 system coupled with UPLC (software: MassLynx 4.1). LC method used a flow rate of 0.2 mL/min and buffers MPA (0.1% TFA in water) and MPB (0.09% TFA in acetonitrile). UV detection was performed at 214 nm and 280 nm. Sample temperature was ~5° C. 14 μl of the deglycosylated and reduced sample (protein amount 3 μg) were loaded onto a BEH C4 1.7 μm, 2.1×100 mm column (Waters). The column temperature was 80° C. Prior to sample loading the column was equilibrated with the buffer MPA. Elution was performed with buffer MPB.

The eluted protein was then further analyzed by mass spectrometry. Using LC/MS data, the clipping sites were identified and the percentage of clipped species quantified. Table 11 shows the percentage of clipped antibody heavy chains based on LC/MS assay in each protein sample. While in the wild-type samples 20 to 29% clipping was observed, only 2% or less of the antibody heavy chain was clipped when using the matriptase knock-out cells for production. The results calculated based on UV214 nm data are slightly higher compared to the ones obtained from reducing LabChip assay (see Table 10). However, the strong reduction of clipping that is achieved when applying the teachings of the present disclosure is again confirmed. The LC/MS results demonstrate a 15-fold decrease in clipping for the mAbs produced in matriptase knock-out cell lines. Analysis of the clipping site revealed that the mAb heavy chain produced in the matriptase knock-out cells is clipped at the same position as the mAb HC produced in the CHO wild-type cell lines. Protein modelling further revealed that the clipping site is located in a very flexible area of the mAb which is exposed to the cell culture medium. Thus, even proteases with a low affinity for this clipping site can easily access and cleave it. These findings may explain the residual clipping events in matriptase knock-out strains.

TABLE 11

Clipping analysis based on LC/MS assay

| Sample | Clipped mAb Heavy Chain [%] |
|---|---|
| WT 1 | 28.5 |
| WT 2 | 23.5 |
| WT 3 | 19.6 |
| KO-4 1 | 2.0 |
| KO-4 2 | 1.5 |
| KO-4 3 | 1.8 |
| KO-4 4 | 1.7 |

5.4. Transfection of WT and KO-4 with Further Glycoproteins

Further examples were performed to again demonstrate that the introduced matriptase knock-out does not negatively affect the production level and product quality of recombinant glycoproteins. Two glycoproteins different from an antibody (here a Fc-fusion protein as well as one recombinant therapeutic protein) were expressed. The matriptase knock-out cell line KO-4 and the CHO wildtype cell line from which clone KO-4 was derived were transfected with suitable expression vectors. After transfection and selection, titer and protein analytics (e.g. as described above in chapter 5.3) were performed.

The protein titers achieved by the matriptase KO cell line KO-4 were in the same range or higher as in the corresponding WT cell line from which clone KO-4 was derived (see also Table 12). Clipping was again significantly reduced in the proteins such as the Fc-fusion protein obtained from the KO cells vs. the proteins such as the Fc-fusion protein obtained from the WT cells (see also Table 13). This clearly shows that a KO of the matriptase gene reduced proteolytic degradation for a variety of further polypeptides.

TABLE 12

Expression analysis of a Fc-fusion protein and a recombinant therapeutic protein

| Candidates | WT | KO-4 |
|---|---|---|
| Fc-fusion protein | 1.32 g/L | 1.24 g/L |
| Recombinant therapeutic protein | 0.59 g/L | 1.11 g/L |

TABLE 13

Clipping analysis of a Fc-fusion protein and a recombinant therapeutic protein

| Candidates | WT Clipped protein [%] | KO-4 Clipped protein [%] |
|---|---|---|
| Fc-fusion protein | 12.4% | 4.5% |
| Recombinant therapeutic protein | 70.2% | 53.9% |

In general, the matriptase KO cell line showed similar or even improved features for the production of glycoproteins. Therefore, the respective cell lines are suitable for the production of proteolytic sensitive polypeptides, as well as for the production of proteolytic insensitive polypeptides. Thus, a universal cell line is provided which simplifies the production of different polypeptides of interest.

VII. Example 6: Upstream Process Suitability and Bioreactor Scale-Up

In order to show suitability of the matriptase knock-out cell line to be scaled-up for large scale therapeutic production, 12 parental clones derived from two different matriptase KO approaches (ZFN and TALEN technology) were evaluated in a three stage screening approach. CHO wildtype cell line was used for comparison.

6.1. Assessment of Parental Clone Performance 6.1.1. Comparison of Parental Clone Performance During Cell Expansion In order to assess the performance of 12 not transfected KO clones (seven ZFN subclones (generated through single cell sorting of the ZFN KO clone described in Example 2b) and five TALEN-derived) and the comparator wild-type cell line during expansion for large-scale production, the seed train was evaluated in shake-flasks using two cell culture expansion media, which differed in the concentration of an essential vitamin. Therefore the clones were inoculated to both expansion media at defined viable cell density and cultured for four days at 36.5° C. The clones were analysed with respect to the final viable cell densities, average growth rates, as described in Table 14. Along with the results from a suitability assessment of the parental clones using production stage medium (Chapter 6.1.2), the seven best performing clones were selected for further comparison with respect to production capabilities (see Chapter 6.2).

TABLE 14

Results of parental clone performances during cell expansion

| Clone ID | Mue [$d^{-1}$] in expansion. medium No. 1 | Mue [$d^{-1}$] in expansion. medium No. 2 | VCD [cells/ml] in expansion. medium No. 1 | VCD [cells/ml] in expansion. medium No. 2 |
|---|---|---|---|---|
| ZFN KO1 | 0.87 | 0.83 | 6.75E+06 | 4.57E+06 |
| ZFN KO1 | 0.83 | 0.80 | 5.50E+06 | 6.88E+06 |
| ZFN KO3 | 0.79 | 0.84 | 4.06E+06 | 8.90E+06 |
| ZFN KO4 | 0.73 | 0.91 | 6.00E+06 | 7.70E+06 |
| ZFN KO5 | 0.86 | 0.86 | 8.99E+06 | 5.03E+06 |
| ZFN KO6 | 0.85 | 0.84 | 7.23E+06 | 5.57E+06 |
| ZFN KO7 | 0.78 | 0.90 | 4.08E+06 | 6.48E+06 |
| TALEN KO-1 | 0.87 | 0.85 | 6.24E+06 | 6.35E+06 |
| TALEN KO-2 | 0.88 | 0.80 | 4.97E+06 | 6.01E+06 |
| TALEN KO-3 | 0.85 | 0.81 | 5.55E+06 | 4.11E+06 |
| TALEN KO-4 | 0.80 | 0.86 | 5.91E+06 | 7.08E+06 |
| TALEN KO-7 | 0.84 | N.A. | 6.19E+06 | N.A. |
| wildtype | 0.81 | N.A. | 6.18E+06 | N.A. |

6.1.2. Comparison of Parental Clone Performance Under Production Conditions

The 12 parental clones and the reference wild-type cell line were further compared in a shake flask fed-batch production process. The cells from the expansion study described in chapter 6.1.1. were cultivated at 36.5° C. for 14 days using two different cultivation conditions (two different chemically defined production media, inoculation cell densities and feeding regimens). Feeding with two independent feed solutions was carried out throughout the process in pre-defined profile and a temperature shift was applied. Cell densities, viabilities and key metabolites were monitored on a daily basis and used to compare the KO clones to the WT clones with respect to suitability for production. Seven clones were identified which achieved a growth performance similar or superior to the wildtype cell line, while the metabolite profiles were comparable.

6.2. Shake Flask Screening of Transfected Pools

The best 7 parental clones as identified in Chapter 6.1 and the CHO wildtype were transfected in triplicate with a monoclonal IgG antibody as polypeptide of interest that was known to be sensitive to proteolytic degradation in the background of the wildtype cell line. The transfected cells were assessed using shake flask cultivation and two different conditions as described in Chapter 6.1.2. Cell growth (viable cell densities, cell viabilities) and product formation was monitored during the cultivation. Cells derived from the TALEN-knock-out approach showed similar or increased cell growth compared to the CHO wildtype cells, whereby ZFN-derived pools showed slightly lower cell growth during exponential phase compared to the TALEN-derived pools. However, cell viability at end of cultivation was comparable for all clones. Volumetric productivity at end of cultivation was on average 19% higher for TALEN and 9% higher for zinc-finger-nuclease pools compared to the productivity of the CHO wildtype pools.

At the end of the cultivation (day 14), the monoclonal IgG antibody was analysed for integrity. Therefore, the supernatants were harvested by centrifugation and sterile filtered. The monoclonal IgG antibody was captured from the supernatants and analyzed by CE-SDS (Capillary Electrophoresis-Sodium Dodecyl Sulfate) for proteolytic degradation and by CEC (cation exchange chromatography) to assess charge variant distribution. All pools derived from knock-out clones showed a similarly low level of ca. 1% of polypeptide clipping, whereas the product derived from the CHO wildtype was cleaved at around 21%.

6.3. Bioreactor Screening of Parental Subclones and Transfected Pools

The four best performing parental clones and transfected pools as identified in chapters 6.1. and 6.2. were selected for in-depth characterization using the controlled cultivation conditions of 7 L glass bioreactors. The cultivation process was essentially as described in Chapter 6.1.2., though only the preferred cultivation conditions as identified in Chapter 6.2 was used. A slightly lower growth was seen for the transfected pools compared to the non-transfected parental clones, which is a known phenomenon ascribed to the metabolic burden caused by the polypeptide expression. However, no significant differences in cell growth behavior were found compared to the WT cell line. Metabolites such as lactate and ammonium were within the common ranges and similar to the wildtype cell line.

The product quality was analytically assessed for purity by SEC, CEC and CE-SDS and N-glycosylation by a proprietary method. The results showed that all KO clones achieved comparable product quality in terms of aggregation and degradation products, charge variant distribution and glycosylation pattern. CE-SDS reduced results showed that clipped species are presents for all KO subclones at a low level of 0.7%. All KO clones not only showed similar or preferred growth characteristics compared the reference wildtype cell line and but also produced polypeptide of consistently better quality.

---

The invention claimed is:

1. An isolated recombinant CHO-K1 derived CHO cell suitable for recombinant expression of a polypeptide of interest, wherein the CHO-K1 derived CHO cell is altered to impair the effect of matriptase, wherein the effect of matriptase is impaired because functional expression of the matriptase gene is reduced or eliminated in said cell by gene knock-out, gene mutation, gene deletion, gene silencing or a combination thereof, wherein the CHO-K1 derived CHO cell comprises at least one heterologous polynucleotide encoding a polypeptide of interest operatively linked to a secretory leader sequence and the polypeptide of interest is secreted from the CHO-K1 derived CHO cell, and wherein impairing the effect of matriptase in said cell reduces clipping of the secreted polypeptide of interest.

2. The isolated CHO-K1 derived CHO cell of claim 1, wherein the genome of the CHO-K1 derived CHO cell is altered to impair the function of endogenous protease matriptase, and/or wherein at least one or all copies of the matriptase gene are deleted or functionally inactivated.

3. The isolated CHO-K1 derived CHO cell of claim 2, wherein
   a) the CHO-K1 derived CHO cell comprises one or more mutations in at least one copy or all copies of the matriptase gene to provide a non- or less-functional expression product; or
   b) the CHO-K1 derived CHO cell comprises one or more mutations in the promoter, in the 5'UTR, the 3'UTR and/or other regulatory elements of the matriptase gene.

4. The isolated CHO-K1 derived CHO cell of claim 3, wherein said one or more mutations are comprised in a coding region of the matriptase gene and result in a non- or less functional expression product, wherein optionally the one or more mutations are comprised in a polynucleotide sequence of exon 2 of the matriptase gene or wherein the one or more mutations are comprised in a polynucleotide sequence of the matriptase gene that encodes at least part of the catalytic domain of matriptase whereby a non- or less functional expression product is obtained.

5. The isolated CHO-K1 derived CHO cell of claim 1, wherein the unaltered endogenous matriptase comprises the amino acid sequence of SEQ ID NO: 1.

6. The isolated CHO-K1 derived CHO cell of claim 1, wherein the CHO-K1 derived CHO cell is provided as cell clone or cell line.

7. The isolated CHO-K1 derived CHO cell of claim 1, wherein the CHO-K1 derived CHO cell comprises one or more frame-shift mutations in exon 2 of one or both alleles of the matriptase gene.

8. The isolated CHO-K1 derived CHO cell of claim 1, wherein the polypeptide:
   a) is a therapeutically active or diagnostic polypeptide;
   b) is susceptible to clipping by proteases;
   c) comprises at least one clipping site for matriptase;
   d) is a glycopolypeptide; and/or
   e) is selected from the group consisting of glycoproteins, antibodies, non-IgG proteins, Fc-fusion proteins, Fab fragments, protein complexes, peptidases, signal peptides, nanobodies, growth factors, hormones, cytokines, blood factors and enzymes.

9. The isolated CHO-K1 derived CHO cell of claim 1, wherein (i) the at least one heterologous polynucleotide encoding the polypeptide of interest operatively linked to a secretory leader sequence is integrated into the genome of said cell and wherein optionally, at least one heterologous polynucleotide encoding a selectable marker or reporter polypeptide is additionally integrated into the genome of said cell; and/or (ii) the at least one heterologous polynucleotide encoding the polypeptide of interest operatively linked to a secretory leader sequence is comprised in an expression cassette.

10. A method for producing a CHO-K1 derived CHO cell of claim 1, comprising altering a CHO-K1 derived CHO cell to impair the effect of matriptase by reducing or eliminating functional expression of the matriptase gene in said cell by gene knock-out, gene mutation, gene deletion, gene silencing or a combination thereof, and introducing a polynucleotide encoding a polypeptide of interest operatively linked to a secretory leader sequence, wherein said polypeptide of interest is secreted by the CHO-K1 derived CHO cell.

11. A method for recombinantly producing a polypeptide of interest, comprising
   (a) culturing CHO-K1 derived CHO cells of claim 1 under conditions that allow for the expression and secretion of the polypeptide of interest into the cell culture medium;
   (b) isolating the polypeptide of interest from the cell culture medium; and
   (c) optionally processing the isolated polypeptide of interest.

12. A method for selecting a host cell which recombinantly expresses a polypeptide of interest, comprising
   (a) providing CHO-K1 derived CHO cells of claim 1 as host cells; and
   (b) selecting one or more host cells expressing the polypeptide of interest;
   wherein optionally step (a) comprises transfecting CHO-K1 derived CHO cells in which the function of the endogenous protease matriptase is impaired with at least one polynucleotide encoding a polypeptide of interest operatively linked to a secretory leader sequence to provide the CHO-K1 derived CHO host cells.

13. The method of claim 12, having one or more of the following characteristics:
   a) said CHO-K1 derived CHO cells provided in step (a) additionally comprise at least one heterologous polynucleotide encoding a selectable marker and step (b) comprises culturing said plurality of host cells under conditions selective for the selectable marker;
   b) polynucleotides are introduced into the CHO-K1 derived CHO cells by transfecting one or more expression vectors;
   c) step (b) comprises one or multiple selection steps; and/or
   d) step (b) comprises performing a flow cytometry based selection.

14. A method for selecting a CHO-K1 derived CHO cell for recombinant production of a secreted polypeptide of interest, comprising
   (i) analyzing if endogenous protease matriptase is functionally expressed in a CHO-K1 derived CHO cell,
   (ii) selecting a CHO-K1 derived CHO cell in which the effect of said endogenous protease matriptase is impaired by reduction or elimination of functional expression of the matriptase gene by gene knock-out, gene mutation, gene deletion, gene silencing or a combination thereof for recombinant production of the secreted polypeptide of interest, and
   (iii) introducing a polynucleotide encoding the polypeptide of interest operatively linked to a secretory leader sequence into the CHO-K1 derived CHO cell,
   wherein step (iii) can occur before or after steps (i) and (ii), and wherein the polypeptide of interest is secreted by the CHO-K1 derived CHO cell.

15. The method of claim 11, wherein the genome of said CHO-K1 derived CHO cells is altered to impair the function of the endogenous protease matriptase, and/or wherein at least one or all copies of the matriptase gene are deleted or functionally inactivated.

16. The method of claim 11, wherein the unaltered endogenous matriptase comprises the amino acid sequence of SEQ ID NO: 1.

17. The method of claim 11, wherein said CHO-K1 derived CHO cells are provided as a cell clone or cell line.

18. The method of claim 11, wherein the polypeptide:
   a) is a therapeutically active or diagnostic polypeptide;
   b) is susceptible to clipping by proteases;
   c) comprises at least one clipping site for matriptase;
   d) is a glycopolypeptide; and/or
   e) is selected from the group consisting of glycoproteins, antibodies, non-IgG proteins, Fc-fusion proteins, Fab fragments, protein complexes, peptidases, signal peptides, nanobodies, growth factors, hormones, cytokines, blood factors and enzymes.

19. The method of claim 11, wherein (i) at least one heterologous polynucleotide encoding the polypeptide of interest operatively linked to a secretory leader sequence is integrated into the genome of said CHO-K1 derived CHO cells and wherein optionally, at least one heterologous polynucleotide encoding a selectable marker or reporter polypeptide is additionally integrated into the genome of said cells; and/or (ii) said CHO-K1 derived CHO cells comprise at least one heterologous polynucleotide encoding the polypeptide of interest operatively linked to a secretory leader sequence comprised in an expression cassette.

20. The method of claim 11, wherein
   (a) said CHO-K1 derived CHO cell comprises one or more mutations in at least one copy or all copies of the matriptase gene to provide a non- or less-functional expression product; or
   (b) said CHO-K1 derived CHO cell comprises one or more mutations in the promoter, in the 5'UTR, the 3'UTR and/or other regulatory elements of the matriptase gene.

21. The method of claim 20, wherein said one or more mutations are comprised in a coding region of the matriptase gene and result in a non- or less functional expression product, wherein optionally the one or more mutations are comprised in a polynucleotide sequence of exon 2 of the matriptase gene or wherein the one or more mutations are comprised in a polynucleotide sequence of the matriptase gene that encodes at least part of the catalytic domain of matriptase whereby a non- or less functional expression product is obtained.

22. The method of claim 11, wherein said CHO-K1 derived CHO cell comprises one or more frame-shift mutations in exon 2 of one or both alleles of the matriptase gene.

23. The method of claim 14, wherein
(i) the genome of said selected CHO-K1 derived CHO cell is altered to impair the function of said endogenous protease matriptase, and/or wherein at least one or all copies of said matriptase gene are deleted or functionally inactivated;
(ii) said CHO-K1 derived CHO cell is provided as a cell clone or cell line;
(iii) at least one heterologous polynucleotide encoding the polypeptide of interest operatively linked to a secretory leader sequence is integrated into the genome of said CHO-K1 derived CHO cell and wherein optionally, at least one heterologous polynucleotide encoding a selectable marker or reporter polypeptide is additionally integrated into the genome of said CHO-K1 derived CHO cell; and/or
(iv) said CHO-K1 derived CHO cell comprises at least one heterologous polynucleotide encoding the polypeptide of interest operatively linked to a secretory leader sequence comprised in an expression cassette.

24. The method of claim 14, wherein the unaltered endogenous matriptase comprises the amino acid sequence of SEQ ID NO: 1.

25. The method of claim 14, wherein
(a) said CHO-K1 derived CHO cell comprises one or more mutations in at least one copy or all copies of the matriptase gene to provide a non- or less-functional expression product; or
(b) said CHO-K1 derived CHO cell comprises one or more mutations in the promoter, in the 5'UTR, the 3'UTR and/or other regulatory elements of the matriptase gene.

26. The method of claim 25, wherein said one or more mutations are comprised in a coding region of the matriptase gene and result in a non- or less functional expression product, wherein optionally the one or more mutations are comprised in a polynucleotide sequence of exon 2 of the matriptase gene or wherein the one or more mutations are comprised in a polynucleotide sequence of the matriptase gene that encodes at least part of the catalytic domain of matriptase whereby a non- or less functional expression product is obtained.

27. The method of claim 14, wherein said CHO-K1 derived CHO cell comprises one or more frame-shift mutations in exon 2 of one or both alleles of the matriptase gene.

* * * * *

SEQUENCE LISTING

```
<160> NUMBER OF SEQ ID NOS: 69

<210> SEQ ID NO 1
<211> LENGTH: 855
<212> TYPE: PRT
<213> ORGANISM: Cricetulus griseus

<400> SEQUENCE: 1

Met Gly Ser Asn Arg Gly Arg Lys Ala Gly Gly Ser Ser Lys Asp Phe
1               5                   10                  15

Gly Ala Arg Leu Lys Tyr Ser Ser Gly Leu Glu Asn Met Asn Gly Phe
            20                  25                  30

Glu Glu Gly Val Glu Phe Leu Pro Val Asn Asn Ala Lys Lys Val Glu
        35                  40                  45

Lys Arg Gly Pro Arg Arg Cys Val Val Leu Val Val Leu Leu Val Ser
    50                  55                  60

Phe Leu Phe Leu Ser Leu Val Ala Gly Phe Leu Val Trp His Phe Leu
65                  70                  75                  80

Tyr Ser Asn Val Arg Ile Gln Lys Val Phe Asn Gly His Leu Arg Val
                85                  90                  95

Thr Asn Glu Asn Phe Leu Asp Ala Tyr Glu Asn Ser Asn Ser Thr Glu
            100                 105                 110

Phe Lys Asp Leu Ala Asn Gln Val Lys Glu Ala Leu Lys Leu Leu Tyr
        115                 120                 125

Ser Glu Val Pro Val Leu Gly Pro Tyr His Lys Arg Ser Ala Val Thr
    130                 135                 140

Ala Phe Ser Glu Gly Ser Val Ile Ala Tyr Tyr Trp Ser Glu Phe Ser
145                 150                 155                 160

Ile Pro Pro His Leu Ala Glu Glu Val Asp Arg Ala Met Ala Val Glu
                165                 170                 175
```

```
Arg Val Val Thr Leu Pro Pro Arg Ala Arg Ala Leu Lys Ser Phe Val
            180                 185                 190

Leu Thr Ser Val Val Ala Phe Pro Thr Asp Pro Arg Leu Leu Gly Arg
        195                 200                 205

Thr Gln Asp Asn Ser Cys Asn Phe Ala Leu His Ala His Gly Gly Glu
    210                 215                 220

Val Met Arg Phe Thr Thr Pro Gly Phe Pro Asn Ser Pro Tyr Pro Ala
225                 230                 235                 240

His Ala Arg Cys Gln Trp Val Leu Arg Gly Asp Ala Asp Ser Val Leu
                245                 250                 255

Ser Leu Thr Phe Arg Ser Phe Asp Val Ala Pro Cys Asp Glu Leu Gly
            260                 265                 270

Asn Asp Leu Val Thr Val Tyr Asp Thr Leu Ser Pro Met Glu Pro His
        275                 280                 285

Ala Val Val Arg Leu Cys Gly Thr Tyr Pro Pro Ser Tyr Asn Leu Thr
    290                 295                 300

Phe Leu Ser Ser Gln Asn Val Phe Leu Val Thr Leu Ile Thr Asn Thr
305                 310                 315                 320

Asp Arg Arg His Pro Gly Phe Glu Ala Thr Phe Phe Gln Leu Pro Lys
                325                 330                 335

Met Arg Ser Cys Gly Gly Ser Leu Ser Glu Ala Gln Gly Leu Phe Ser
            340                 345                 350

Ser Pro Tyr Tyr Pro Gly His Tyr Pro Pro Asn Ile Asp Cys Thr Trp
        355                 360                 365

Asn Ile Lys Val Pro Asn Asn Arg Asn Val Lys Val Arg Phe Lys Leu
    370                 375                 380

Phe Tyr Leu Val Asp Pro Asn Ile Pro Leu Gly Thr Cys Pro Lys Asp
385                 390                 395                 400

Tyr Val Glu Ile Asn Gly Glu Arg Tyr Cys Gly Glu Lys Ser Gln Phe
                405                 410                 415

Val Val Ser Ser Asn Ser Ser Lys Ile Thr Val Arg Phe His Ser Asp
            420                 425                 430

His Ser Tyr Thr Asp Thr Gly Phe Leu Ala Glu Tyr Leu Ser Tyr Asp
        435                 440                 445

Ser Asn Asp Pro Cys Pro Gly Met Phe Met Cys Asn Thr Gly Arg Cys
    450                 455                 460

Ile Arg Lys Asp Leu Arg Cys Asp Gly Trp Ala Asp Cys Pro Asp Tyr
465                 470                 475                 480

Ser Asp Glu His Phe Cys Arg Cys Asn Thr Thr His Gln Phe Met Cys
                485                 490                 495

Lys Asn Lys Leu Cys Lys Pro Leu Phe Trp Val Cys Asp Asn Ile Asn
            500                 505                 510

Asp Cys Gly Asp Gly Ser Asp Glu Glu Gly Cys Ser Cys Pro Ala Glu
        515                 520                 525

Thr Phe Lys Cys Ser Asn Gly Lys Cys Leu Pro Gln Ser Gln Lys Cys
    530                 535                 540

Asp Gly Lys Asp Asn Cys Gly Asp Gly Ser Asp Glu Ala Ser Cys Asp
545                 550                 555                 560

Arg Val Lys Val Val Ser Cys Thr Lys Tyr Thr Tyr Arg Cys His Asn
                565                 570                 575

Gly Leu Cys Leu Ser Lys Gly Asn Pro Glu Cys Asp Gly Lys Lys Asp
            580                 585                 590
```

-continued

```
Cys Ser Asp Gly Ser Asp Glu Lys Asn Cys Asp Cys Gly Leu Arg Ser
            595                 600                 605
Phe Thr Lys Gln Ala Arg Val Val Gly Thr Asn Ala Asp Glu Gly
    610                 615                 620
Glu Trp Pro Trp Gln Val Ser Leu His Ala Leu Gly Gln Gly His Leu
625                 630                 635                 640
Cys Gly Ala Ser Leu Ile Ser Pro Asn Trp Leu Val Ser Ala Ala His
                645                 650                 655
Cys Phe Met Asp Asp Arg Asn Phe Lys Tyr Ser Asp His Thr Lys Trp
            660                 665                 670
Thr Ala Phe Leu Gly Leu Leu Asp Gln Ser Lys Arg Ser Ser Thr Gly
        675                 680                 685
Val Gln Glu His Lys Leu Lys Arg Ile Ile Thr His Pro Leu Phe Asn
    690                 695                 700
Glu Ile Thr Phe Asp Tyr Asp Ile Ala Leu Leu Glu Leu Glu Lys Pro
705                 710                 715                 720
Ala Glu Tyr Ser Thr Val Val Arg Pro Ile Cys Leu Pro Asp Thr Thr
                725                 730                 735
His Val Phe Pro Ala Gly Lys Ala Ile Trp Val Thr Gly Trp Gly His
            740                 745                 750
Thr Gln Glu Gly Gly Thr Gly Ala Leu Ile Leu Gln Lys Gly Glu Ile
        755                 760                 765
Arg Val Ile Asn Gln Thr Thr Cys Glu Asp Leu Met Pro Gln Gln Ile
    770                 775                 780
Thr Pro Arg Met Met Cys Val Gly Phe Leu Ser Gly Gly Val Asp Ser
785                 790                 795                 800
Cys Gln Gly Asp Ser Gly Gly Pro Leu Ser Ser Val Glu Thr Glu Gly
                805                 810                 815
Arg Ile Phe Gln Ala Gly Val Val Ser Trp Gly Gly Cys Ala Gln
            820                 825                 830
Arg Asn Lys Pro Gly Val Tyr Thr Arg Leu Pro Ala Val Arg Asp Trp
        835                 840                 845
Ile Lys Glu Gln Thr Gly Val
    850                 855

<210> SEQ ID NO 2
<211> LENGTH: 855
<212> TYPE: PRT
<213> ORGANISM: Homo sapiens

<400> SEQUENCE: 2

Met Gly Ser Asp Arg Ala Arg Lys Gly Gly Gly Gly Pro Lys Asp Phe
1               5                   10                  15
Gly Ala Gly Leu Lys Tyr Asn Ser Arg His Glu Lys Val Asn Gly Leu
                20                  25                  30
Glu Glu Gly Val Glu Phe Leu Pro Val Asn Asn Val Lys Lys Val Glu
            35                  40                  45
Lys His Gly Pro Gly Arg Trp Val Val Leu Ala Ala Val Leu Ile Gly
        50                  55                  60
Leu Leu Leu Val Leu Leu Gly Ile Gly Phe Leu Val Trp His Leu Gln
65                  70                  75                  80
Tyr Arg Asp Val Arg Val Gln Lys Val Phe Asn Gly Tyr Met Arg Ile
                85                  90                  95
Thr Asn Glu Asn Phe Val Asp Ala Tyr Glu Asn Ser Asn Ser Thr Glu
            100                 105                 110
```

```
Phe Val Ser Leu Ala Ser Lys Val Lys Asp Ala Leu Lys Leu Leu Tyr
            115                 120                 125

Ser Gly Val Pro Phe Leu Gly Pro Tyr His Lys Glu Ser Ala Val Thr
            130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
                180                 185                 190

Val Thr Ser Val Val Ala Phe Pro Thr Asp Ser Lys Thr Val Gln Arg
            195                 200                 205

Thr Gln Asp Asn Ser Cys Ser Phe Gly Leu His Ala Arg Gly Val Glu
    210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
            260                 265                 270

Ser Asp Leu Val Thr Val Tyr Asn Thr Leu Ser Pro Met Glu Pro His
            275                 280                 285

Ala Leu Val Gln Leu Cys Gly Thr Tyr Pro Pro Ser Tyr Asn Leu Thr
    290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
            340                 345                 350

Ser Pro Tyr Tyr Pro Gly His Tyr Pro Pro Asn Ile Asp Cys Thr Trp
            355                 360                 365

Asn Ile Glu Val Pro Asn Asn Gln His Val Lys Val Arg Phe Lys Phe
            370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Gly Glu Arg Ser Gln Phe
                405                 410                 415

Val Val Thr Ser Asn Ser Asn Lys Ile Thr Val Arg Phe His Ser Asp
            420                 425                 430

Gln Ser Tyr Thr Asp Thr Gly Phe Leu Ala Glu Tyr Leu Ser Tyr Asp
            435                 440                 445

Ser Ser Asp Pro Cys Pro Gly Gln Phe Thr Cys Arg Thr Gly Arg Cys
    450                 455                 460

Ile Arg Lys Glu Leu Arg Cys Asp Gly Trp Ala Asp Cys Thr Asp His
465                 470                 475                 480

Ser Asp Glu Leu Asn Cys Ser Cys Asp Ala Gly His Gln Phe Thr Cys
                485                 490                 495

Lys Asn Lys Phe Cys Lys Pro Leu Phe Trp Val Cys Asp Ser Val Asn
            500                 505                 510

Asp Cys Gly Asp Asn Ser Asp Glu Gln Gly Cys Ser Cys Pro Ala Gln
            515                 520                 525
```

-continued

Thr Phe Arg Cys Ser Asn Gly Lys Cys Leu Ser Lys Ser Gln Gln Cys
    530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
                565                 570                 575

Gly Leu Cys Leu Ser Lys Gly Asn Pro Glu Cys Asp Gly Lys Glu Asp
            580                 585                 590

Cys Ser Asp Gly Ser Asp Glu Lys Asp Cys Asp Cys Gly Leu Arg Ser
        595                 600                 605

Phe Thr Arg Gln Ala Arg Val Val Gly Gly Thr Asp Ala Asp Glu Gly
    610                 615                 620

Glu Trp Pro Trp Gln Val Ser Leu His Ala Leu Gly Gln Gly His Ile
625                 630                 635                 640

Cys Gly Ala Ser Leu Ile Ser Pro Asn Trp Leu Val Ser Ala Ala His
                645                 650                 655

Cys Tyr Ile Asp Asp Arg Gly Phe Arg Tyr Ser Asp Pro Thr Gln Trp
            660                 665                 670

Thr Ala Phe Leu Gly Leu His Asp Gln Ser Gln Arg Ser Ala Pro Gly
        675                 680                 685

Val Gln Glu Arg Arg Leu Lys Arg Ile Ile Ser His Pro Phe Phe Asn
    690                 695                 700

Asp Phe Thr Phe Asp Tyr Asp Ile Ala Leu Leu Glu Leu Glu Lys Pro
705                 710                 715                 720

Ala Glu Tyr Ser Ser Met Val Arg Pro Ile Cys Leu Pro Asp Ala Ser
                725                 730                 735

His Val Phe Pro Ala Gly Lys Ala Ile Trp Val Thr Gly Trp Gly His
            740                 745                 750

Thr Gln Tyr Gly Gly Thr Gly Ala Leu Ile Leu Gln Lys Gly Glu Ile
        755                 760                 765

Arg Val Ile Asn Gln Thr Thr Cys Glu Asn Leu Leu Pro Gln Gln Ile
    770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Val Glu Ala Asp Gly
                805                 810                 815

Arg Ile Phe Gln Ala Gly Val Val Ser Trp Gly Asp Gly Cys Ala Gln
            820                 825                 830

Arg Asn Lys Pro Gly Val Tyr Thr Arg Leu Pro Leu Phe Arg Asp Trp
        835                 840                 845

Ile Lys Glu Asn Thr Gly Val
    850                 855

<210> SEQ ID NO 3
<211> LENGTH: 855
<212> TYPE: PRT
<213> ORGANISM: Mus musculus

<400> SEQUENCE: 3

Met Gly Ser Asn Arg Gly Arg Lys Ala Gly Gly Gly Ser Gln Asp Phe
1               5                   10                  15

Gly Ala Gly Leu Lys Tyr Asn Ser Arg Leu Glu Asn Met Asn Gly Phe
            20                  25                  30

Glu Glu Gly Val Glu Phe Leu Pro Ala Asn Asn Ala Lys Lys Val Glu
        35                  40                  45

-continued

Lys Arg Gly Pro Arg Arg Trp Val Val Leu Val Ala Val Leu Phe Ser
 50                  55                  60

Phe Leu Leu Leu Ser Leu Met Ala Gly Leu Leu Val Trp His Phe His
 65                  70                  75                  80

Tyr Arg Asn Val Arg Val Gln Lys Val Phe Asn Gly His Leu Arg Ile
                 85                  90                  95

Thr Asn Glu Ile Phe Leu Asp Ala Tyr Glu Asn Ser Thr Ser Thr Glu
             100                 105                 110

Phe Ile Ser Leu Ala Ser Gln Val Lys Glu Ala Leu Lys Leu Leu Tyr
             115                 120                 125

Asn Glu Val Pro Val Leu Gly Pro Tyr His Lys Lys Ser Ala Val Thr
130                 135                 140

Ala Phe Ser Glu Gly Ser Val Ile Ala Tyr Tyr Trp Ser Glu Phe Ser
145                 150                 155                 160

Ile Pro Pro His Leu Ala Glu Glu Val Asp Arg Ala Met Ala Val Glu
                 165                 170                 175

Arg Val Val Thr Leu Pro Pro Arg Ala Arg Ala Leu Lys Ser Phe Val
             180                 185                 190

Leu Thr Ser Val Val Ala Phe Pro Ile Asp Pro Arg Met Leu Gln Arg
             195                 200                 205

Thr Gln Asp Asn Ser Cys Ser Phe Ala Leu His Ala His Gly Ala Ala
210                 215                 220

Val Thr Arg Phe Thr Thr Pro Gly Phe Pro Asn Ser Pro Tyr Pro Ala
225                 230                 235                 240

His Ala Arg Cys Gln Trp Val Leu Arg Gly Asp Ala Asp Ser Val Leu
                 245                 250                 255

Ser Leu Thr Phe Arg Ser Phe Asp Val Ala Pro Cys Asp Glu His Gly
             260                 265                 270

Ser Asp Leu Val Thr Val Tyr Asp Ser Leu Ser Pro Met Glu Pro His
             275                 280                 285

Ala Val Val Arg Leu Cys Gly Thr Phe Ser Pro Ser Tyr Asn Leu Thr
290                 295                 300

Phe Leu Ser Ser Gln Asn Val Phe Leu Val Thr Leu Ile Thr Asn Thr
305                 310                 315                 320

Asp Arg Arg His Pro Gly Phe Glu Ala Thr Phe Phe Gln Leu Pro Lys
                 325                 330                 335

Met Ser Ser Cys Gly Gly Phe Leu Ser Asp Thr Gln Gly Thr Phe Ser
             340                 345                 350

Ser Pro Tyr Tyr Pro Gly His Tyr Pro Pro Asn Ile Asn Cys Thr Trp
             355                 360                 365

Asn Ile Lys Val Pro Asn Asn Arg Asn Val Lys Val Arg Phe Lys Leu
370                 375                 380

Phe Tyr Leu Val Asp Pro Asn Val Pro Val Gly Ser Cys Thr Lys Asp
385                 390                 395                 400

Tyr Val Glu Ile Asn Gly Glu Lys Tyr Cys Gly Glu Arg Ser Gln Phe
                 405                 410                 415

Val Val Ser Ser Asn Ser Ser Lys Ile Thr Val His Phe His Ser Asp
             420                 425                 430

His Ser Tyr Thr Asp Thr Gly Phe Leu Ala Glu Tyr Leu Ser Tyr Asp
             435                 440                 445

Ser Asn Asp Pro Cys Pro Gly Met Phe Met Cys Lys Thr Gly Arg Cys
450                 455                 460

Ile Arg Lys Glu Leu Arg Cys Asp Gly Trp Ala Asp Cys Pro Asp Tyr
465                 470                 475                 480

Ser Asp Glu Arg Tyr Cys Arg Cys Asn Ala Thr His Gln Phe Thr Cys
            485                 490                 495

Lys Asn Gln Phe Cys Lys Pro Leu Phe Trp Val Cys Asp Ser Val Asn
            500                 505                 510

Asp Cys Gly Asp Gly Ser Asp Glu Glu Gly Cys Ser Cys Pro Ala Gly
            515                 520                 525

Ser Phe Lys Cys Ser Asn Gly Lys Cys Leu Pro Gln Ser Gln Lys Cys
            530                 535                 540

Asn Gly Lys Asp Asn Cys Gly Asp Gly Ser Asp Glu Ala Ser Cys Asp
545                 550                 555                 560

Ser Val Asn Val Val Ser Cys Thr Lys Tyr Thr Tyr Arg Cys Gln Asn
            565                 570                 575

Gly Leu Cys Leu Ser Lys Gly Asn Pro Glu Cys Asp Gly Lys Thr Asp
            580                 585                 590

Cys Ser Asp Gly Ser Asp Glu Lys Asn Cys Asp Cys Gly Leu Arg Ser
            595                 600                 605

Phe Thr Lys Gln Ala Arg Val Val Gly Gly Thr Asn Ala Asp Glu Gly
            610                 615                 620

Glu Trp Pro Trp Gln Val Ser Leu His Ala Leu Gly Gln Gly His Leu
625                 630                 635                 640

Cys Gly Ala Ser Leu Ile Ser Pro Asp Trp Leu Val Ser Ala Ala His
            645                 650                 655

Cys Phe Gln Asp Asp Lys Asn Phe Lys Tyr Ser Asp Tyr Thr Met Trp
            660                 665                 670

Thr Ala Phe Leu Gly Leu Leu Asp Gln Ser Lys Arg Ser Ala Ser Gly
            675                 680                 685

Val Gln Glu Leu Lys Leu Lys Arg Ile Ile Thr His Pro Ser Phe Asn
            690                 695                 700

Asp Phe Thr Phe Asp Tyr Asp Ile Ala Leu Leu Glu Leu Glu Lys Ser
705                 710                 715                 720

Val Glu Tyr Ser Thr Val Val Arg Pro Ile Cys Leu Pro Asp Ala Thr
            725                 730                 735

His Val Phe Pro Ala Gly Lys Ala Ile Trp Val Thr Gly Trp Gly His
            740                 745                 750

Thr Lys Glu Gly Gly Thr Gly Ala Leu Ile Leu Gln Lys Gly Glu Ile
            755                 760                 765

Arg Val Ile Asn Gln Thr Thr Cys Glu Asp Leu Met Pro Gln Gln Ile
            770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Ala Glu Lys Asp Gly
            805                 810                 815

Arg Met Phe Gln Ala Gly Val Val Ser Trp Gly Glu Cys Ala Gln
            820                 825                 830

Arg Asn Lys Pro Gly Val Tyr Thr Arg Leu Pro Val Val Arg Asp Trp
            835                 840                 845

Ile Lys Glu His Thr Gly Val
            850                 855

<210> SEQ ID NO 4
<211> LENGTH: 855
<212> TYPE: PRT

<213> ORGANISM: Rattus norvegicus

<400> SEQUENCE: 4

```
Met Gly Asn Asn Arg Gly Arg Lys Ala Gly Gly Ser Gln Asp Phe
1               5                   10                  15

Gly Ala Gly Leu Lys Tyr Asn Ser Arg Leu Glu Asn Met Asn Gly Phe
                20                  25                  30

Glu Glu Gly Val Glu Phe Leu Pro Val Asn Asn Ala Lys Gln Val Glu
                35                  40                  45

Lys Arg Gly Pro Arg Arg Trp Val Val Met Val Ala Val Val Phe Ser
            50                  55                  60

Phe Leu Leu Leu Ser Leu Met Ala Gly Leu Leu Val Trp His Phe His
65                  70                  75                  80

Tyr Arg Asn Val Arg Ile Gln Lys Val Phe Asn Gly His Leu Arg Ile
                85                  90                  95

Thr Asn Glu Asn Phe Leu Asp Ala Tyr Glu Asn Ser Thr Ser Thr Glu
            100                 105                 110

Phe Ile Ser Leu Ala Ser Gln Val Lys Glu Ala Leu Lys Leu Met Tyr
                115                 120                 125

Ser Glu Val Pro Val Leu Gly Pro Tyr His Lys Lys Ser Thr Val Thr
130                 135                 140

Ala Phe Ser Glu Gly Ser Val Ile Ala Tyr Tyr Trp Ser Glu Phe Ser
145                 150                 155                 160

Ile Pro Pro His Leu Glu Glu Val Asp Arg Ala Met Ala Val Glu
                165                 170                 175

Arg Val Val Thr Leu Pro Pro Arg Ala Arg Ala Leu Lys Ser Phe Val
                180                 185                 190

Leu Thr Ser Val Val Ala Phe Pro Ile Asp Pro Arg Met Leu Gln Arg
            195                 200                 205

Thr Gln Asp Asn Ser Cys Ser Phe Ala Leu His Ala Arg Gly Arg Thr
            210                 215                 220

Val Thr Arg Phe Thr Thr Pro Gly Phe Pro Asn Ser Pro Tyr Pro Ala
225                 230                 235                 240

His Ala Arg Cys Gln Trp Val Leu Arg Gly Asp Ala Asp Ser Val Leu
                245                 250                 255

Ser Leu Thr Phe Arg Ser Phe Asp Val Ala Pro Cys Asp Gly His Asp
                260                 265                 270

Ser Asp Leu Val Thr Val Tyr Asp Ser Leu Ser Pro Met Glu Pro His
            275                 280                 285

Ala Val Val Arg Leu Cys Gly Thr Phe Ser Pro Ser Tyr Asn Leu Thr
            290                 295                 300

Phe Leu Ser Ser Gln Asn Val Phe Leu Val Thr Leu Ile Thr Asn Thr
305                 310                 315                 320

Asp Arg Arg His Pro Gly Phe Glu Ala Thr Phe Phe Gln Leu Pro Lys
                325                 330                 335

Met Ser Ser Cys Gly Gly Leu Leu Ser Glu Ala Gln Gly Thr Phe Ser
            340                 345                 350

Ser Pro Tyr Tyr Pro Gly His Tyr Pro Pro Asn Ile Asn Cys Thr Trp
                355                 360                 365

Asn Ile Lys Val Pro Asn Asn Arg Asn Val Lys Val Arg Phe Lys Leu
            370                 375                 380

Phe Tyr Leu Val Asp Pro Asn Ile Pro Val Gly Ser Cys Thr Lys Asp
385                 390                 395                 400
```

```
Tyr Val Glu Ile Asn Gly Glu Lys Phe Cys Gly Arg Ser Gln Phe
                405                 410                 415

Val Val Ser Ser Asn Ser Ser Lys Ile Thr Val His Phe His Ser Asp
            420                 425                 430

His Ser Tyr Thr Asp Thr Gly Phe Leu Ala Glu Tyr Leu Ser Tyr Asp
            435                 440                 445

Ser Asn Asp Pro Cys Pro Gly Met Phe Met Cys Lys Thr Gly Arg Cys
450                 455                 460

Ile Arg Lys Asp Leu Arg Cys Asp Gly Trp Ala Asp Cys Pro Asp Tyr
465                 470                 475                 480

Ser Asp Glu Arg His Cys Arg Cys Asn Ala Thr His Gln Phe Met Cys
            485                 490                 495

Lys Asn Gln Phe Cys Lys Pro Leu Phe Trp Val Cys Asp Ser Val Asn
            500                 505                 510

Asp Cys Gly Asp Gly Ser Asp Glu Glu Gly Cys Ser Cys Pro Ala Gly
            515                 520                 525

Ser Phe Lys Cys Ser Asn Gly Lys Cys Leu Pro Gln Ser Gln Gln Cys
            530                 535                 540

Asn Gly Lys Asp Asp Cys Gly Asp Gly Ser Asp Glu Ala Ser Cys Asp
545                 550                 555                 560

Asn Val Asn Ala Val Ser Cys Thr Lys Tyr Thr Tyr Arg Cys Gln Asn
                565                 570                 575

Gly Leu Cys Leu Asn Lys Gly Asn Pro Glu Cys Asp Gly Lys Lys Asp
            580                 585                 590

Cys Ser Asp Gly Ser Asp Glu Lys Asn Cys Asp Cys Gly Leu Arg Ser
            595                 600                 605

Phe Thr Lys Gln Ala Arg Val Val Gly Gly Thr Asn Ala Asp Glu Gly
            610                 615                 620

Glu Trp Pro Trp Gln Val Ser Leu His Ala Leu Gly Gln Gly His Leu
625                 630                 635                 640

Cys Gly Ala Ser Leu Ile Ser Pro Asp Trp Leu Val Ser Ala Ala His
                645                 650                 655

Cys Phe Gln Asp Glu Thr Ile Phe Lys Tyr Ser Asp His Thr Met Trp
            660                 665                 670

Thr Ala Phe Leu Gly Leu Leu Asp Gln Ser Lys Arg Ser Ala Ser Gly
            675                 680                 685

Val Gln Glu His Lys Leu Lys Arg Ile Ile Thr His Pro Ser Phe Asn
            690                 695                 700

Asp Phe Thr Phe Asp Tyr Asp Ile Ala Leu Leu Glu Leu Glu Lys Pro
705                 710                 715                 720

Ala Glu Tyr Ser Thr Val Val Arg Pro Ile Cys Leu Pro Asp Asn Thr
                725                 730                 735

His Val Phe Pro Ala Gly Lys Ala Ile Trp Val Thr Gly Trp Gly His
            740                 745                 750

Thr Lys Glu Gly Gly Thr Gly Ala Leu Ile Leu Gln Lys Gly Glu Ile
            755                 760                 765

Arg Val Ile Asn Gln Thr Thr Cys Glu Glu Leu Leu Pro Gln Gln Ile
770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Val Glu Lys Asp Gly
                805                 810                 815

Arg Ile Phe Gln Ala Gly Val Val Ser Trp Gly Glu Gly Cys Ala Gln
```

```
                    820                 825                 830
Arg Asn Lys Pro Gly Val Tyr Thr Arg Ile Pro Glu Val Arg Asp Trp
                835                 840                 845

Ile Lys Glu Gln Thr Gly Val
            850                 855

<210> SEQ ID NO 5
<211> LENGTH: 855
<212> TYPE: PRT
<213> ORGANISM: Pan troglodytes
<220> FEATURE:
<221> NAME/KEY: misc_feature
<222> LOCATION: (561)..(561)
<223> OTHER INFORMATION: Xaa can be any naturally occurring amino acid

<400> SEQUENCE: 5

Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
                20                  25                  30

Glu Glu Gly Val Glu Phe Leu Pro Val Asn Asn Val Lys Lys Val Glu
            35                  40                  45

Lys His Gly Pro Gly Arg Trp Val Val Leu Ala Ala Val Leu Ile Gly
        50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
            100                 105                 110

Phe Val Ser Leu Ala Ser Lys Val Lys Asp Ala Leu Lys Leu Leu Tyr
        115                 120                 125

Ser Gly Val Pro Phe Leu Gly Pro Tyr His Lys Glu Ser Ala Val Thr
130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
            180                 185                 190

Val Thr Ser Val Val Ala Phe Pro Thr Asp Ser Lys Thr Val Gln Arg
        195                 200                 205

Thr Gln Asp Asn Ser Cys Ser Phe Gly Leu His Ala Arg Gly Val Glu
210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
            260                 265                 270

Ser Asp Leu Val Met Val Tyr Asn Thr Leu Ser Pro Met Glu Pro His
        275                 280                 285

Ala Leu Val Gln Leu Cys Gly Thr Tyr Pro Pro Ser Tyr Asn Leu Thr
290                 295                 300

Phe His Ser Ser Gln Asn Val Leu Leu Val Thr Leu Ile Thr Asn Thr
305                 310                 315                 320
```

-continued

Arg Arg Arg His Pro Gly Phe Glu Ala Thr Phe Phe Gln Leu Pro Arg
                325                 330                 335

Met Arg Ser Cys Gly Gly Arg Leu Arg Lys Ala Gln Gly Thr Phe Asn
                340                 345                 350

Ser Pro Tyr Tyr Pro Gly His Tyr Pro Pro Asn Ile Asp Cys Thr Trp
                355                 360                 365

Asn Ile Glu Val Pro Asn Asn Gln His Val Lys Val Arg Phe Lys Phe
370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Gly Glu Arg Ser Gln Phe
                405                 410                 415

Val Val Thr Ser Asn Ser Asn Lys Ile Thr Val Arg Phe His Ser Asp
                420                 425                 430

Gln Ser Tyr Thr Asp Thr Gly Phe Leu Ala Glu Tyr Val Ser Tyr Asp
                435                 440                 445

Ser Ser Asp Pro Cys Pro Gly Gln Phe Thr Cys Arg Thr Gly Arg Cys
450                 455                 460

Ile Arg Lys Glu Leu Arg Cys Asp Gly Trp Ala Asp Cys Thr Asp His
465                 470                 475                 480

Ser Asp Glu Leu Asn Cys Ser Cys Asp Ala Ser His Gln Phe Thr Cys
                485                 490                 495

Lys Asn Lys Phe Cys Lys Pro Leu Phe Trp Val Cys Asp Ser Val Asn
                500                 505                 510

Asp Cys Gly Asp Asn Ser Asp Glu Gln Gly Cys Ser Cys Pro Ala Gln
                515                 520                 525

Thr Phe Arg Cys Ser Asn Gly Lys Cys Leu Ser Lys Ser Gln Gln Cys
                530                 535                 540

Asn Gly Lys Asp Asp Cys Gly Asp Gly Ser Asp Glu Ala Ser Cys Pro
545                 550                 555                 560

Xaa Val Asn Val Val Thr Cys Thr Lys His Thr Tyr Arg Cys Leu Asn
                565                 570                 575

Gly Leu Cys Leu Ser Lys Gly Asn Pro Glu Cys Asp Gly Lys Glu Asp
                580                 585                 590

Cys Ser Asp Gly Ser Asp Glu Lys Asp Cys Asp Cys Gly Leu Arg Ser
                595                 600                 605

Phe Thr Arg Gln Ala Arg Val Val Gly Gly Thr Asp Ala Asp Glu Gly
                610                 615                 620

Glu Trp Pro Trp Gln Val Ser Leu His Ala Leu Gly Gln Gly His Ile
625                 630                 635                 640

Cys Gly Ala Ser Leu Ile Ser Pro Asn Trp Leu Val Ser Ala Ala His
                645                 650                 655

Cys Tyr Ile Asp Asp Arg Gly Phe Arg Tyr Ser Asp Pro Thr Gln Trp
                660                 665                 670

Thr Ala Phe Leu Gly Leu His Asp Gln Ser Gln Arg Ser Ala Pro Gly
                675                 680                 685

Val Gln Glu Arg Arg Leu Lys Arg Ile Ile Ser His Pro Phe Phe Asn
                690                 695                 700

Asp Phe Thr Phe Asp Tyr Asp Ile Ala Leu Leu Glu Leu Glu Lys Pro
705                 710                 715                 720

Ala Glu Tyr Ser Ser Met Val Arg Pro Ile Cys Leu Pro Asp Ala Ser
                725                 730                 735

```
His Val Phe Pro Ala Gly Lys Ala Ile Trp Val Thr Gly Trp His
                740                 745                 750

Thr Gln Tyr Gly Gly Thr Gly Ala Leu Ile Leu Gln Lys Gly Glu Ile
            755                 760                 765

Arg Val Ile Asn Gln Thr Thr Cys Glu Asn Leu Leu Pro Gln Gln Ile
        770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Val Glu Ala Asp Gly
                805                 810                 815

Arg Ile Phe Gln Ala Gly Val Val Ser Trp Gly Asp Gly Cys Ala Gln
            820                 825                 830

Arg Asn Lys Pro Gly Val Tyr Thr Arg Leu Pro Leu Phe Arg Asp Trp
        835                 840                 845

Ile Lys Glu Asn Thr Gly Val
    850                 855

<210> SEQ ID NO 6
<211> LENGTH: 21
<212> TYPE: DNA
<213> ORGANISM: Artificial Sequence
<220> FEATURE:
<223> OTHER INFORMATION: Matriptase/MT-SP1 - sense sequence of siRNA

<400> SEQUENCE: 6
gcaagaucac uguucgcuut t                                              21

<210> SEQ ID NO 7
<211> LENGTH: 21
<212> TYPE: DNA
<213> ORGANISM: Artificial Sequence
<220> FEATURE:
<223> OTHER INFORMATION: Matriptase/MT-SP1 Antisense sequence of siRNA

<400> SEQUENCE: 7
aagcgaacag ugaucuugct g                                              21

<210> SEQ ID NO 8
<211> LENGTH: 21
<212> TYPE: DNA
<213> ORGANISM: Artificial Sequence
<220> FEATURE:
<223> OTHER INFORMATION: C1ra - Sense sequence of siRNA

<400> SEQUENCE: 8
gaugucuuuu cucaaaauat t                                              21

<210> SEQ ID NO 9
<211> LENGTH: 21
<212> TYPE: DNA
<213> ORGANISM: Artificial Sequence
<220> FEATURE:
<223> OTHER INFORMATION: C1ra - Antisense sequence of siRNA

<400> SEQUENCE: 9
uauuuugaga aaagacauca t                                              21

<210> SEQ ID NO 10
<211> LENGTH: 21
<212> TYPE: DNA
<213> ORGANISM: Artificial Sequence
<220> FEATURE:
<223> OTHER INFORMATION: Gm5077 - sense sequence of siRNA
```

```
<400> SEQUENCE: 10
cgcugaacgu gugauuauut t                                              21

<210> SEQ ID NO 11
<211> LENGTH: 21
<212> TYPE: DNA
<213> ORGANISM: Artificial Sequence
<220> FEATURE:
<223> OTHER INFORMATION: Gm5077 - Antisense sequence of siRNA

<400> SEQUENCE: 11
aauaaucaca cguucagcgg t                                              21

<210> SEQ ID NO 12
<211> LENGTH: 21
<212> TYPE: DNA
<213> ORGANISM: Artificial Sequence
<220> FEATURE:
<223> OTHER INFORMATION: Plat - Sense sequence of siRNA

<400> SEQUENCE: 12
gaaacaagau gaagacagat t                                              21

<210> SEQ ID NO 13
<211> LENGTH: 21
<212> TYPE: DNA
<213> ORGANISM: Artificial Sequence
<220> FEATURE:
<223> OTHER INFORMATION: Plat - Antisense sequence of siRNA

<400> SEQUENCE: 13
ucugucuuca ucuuguuucc c                                              21

<210> SEQ ID NO 14
<211> LENGTH: 21
<212> TYPE: DNA
<213> ORGANISM: Artificial Sequence
<220> FEATURE:
<223> OTHER INFORMATION: Prss35 - Sense sequence of siRNA

<400> SEQUENCE: 14
ggccuuagac uacgacuaut t                                              21

<210> SEQ ID NO 15
<211> LENGTH: 21
<212> TYPE: DNA
<213> ORGANISM: Artificial Sequence
<220> FEATURE:
<223> OTHER INFORMATION: Prss35 - Antisense sequence of siRNA

<400> SEQUENCE: 15
auagucguag ucuaaggccg g                                              21

<210> SEQ ID NO 16
<211> LENGTH: 21
<212> TYPE: DNA
<213> ORGANISM: Artificial Sequence
<220> FEATURE:
<223> OTHER INFORMATION: Matriptase/MT-SP1 - Forward Primer Sequence

<400> SEQUENCE: 16
cgctgagtac ctgtcctacg a                                              21

<210> SEQ ID NO 17
```

```
<211> LENGTH: 23
<212> TYPE: DNA
<213> ORGANISM: Artificial Sequence
<220> FEATURE:
<223> OTHER INFORMATION: Matriptase/MT-SP1 - Reverse Primer Sequence

<400> SEQUENCE: 17
accgtccagt gttacacatg aac                                              23

<210> SEQ ID NO 18
<211> LENGTH: 16
<212> TYPE: DNA
<213> ORGANISM: Artificial Sequence
<220> FEATURE:
<223> OTHER INFORMATION: Matriptase/MT-SP1 Reporter 1 Sequence

<400> SEQUENCE: 18
ccaatgaccc atgccc                                                      16

<210> SEQ ID NO 19
<211> LENGTH: 20
<212> TYPE: DNA
<213> ORGANISM: Artificial Sequence
<220> FEATURE:
<223> OTHER INFORMATION: C1ra Forward Primer Sequence

<400> SEQUENCE: 19
acctgcaaac aaggctacca                                                  20

<210> SEQ ID NO 20
<211> LENGTH: 20
<212> TYPE: DNA
<213> ORGANISM: Artificial Sequence
<220> FEATURE:
<223> OTHER INFORMATION: C1ra Reverse Primer Sequence

<400> SEQUENCE: 20
tggcaaacag ctgtgaagga                                                  20

<210> SEQ ID NO 21
<211> LENGTH: 15
<212> TYPE: DNA
<213> ORGANISM: Artificial Sequence
<220> FEATURE:
<223> OTHER INFORMATION: C1ra Reporter 1 Sequence

<400> SEQUENCE: 21
cagcacctgg tttcc                                                       15

<210> SEQ ID NO 22
<211> LENGTH: 24
<212> TYPE: DNA
<213> ORGANISM: Artificial Sequence
<220> FEATURE:
<223> OTHER INFORMATION: Gm5077 Forward Primer Sequence

<400> SEQUENCE: 22
tgcgaggagc catattacta catg                                             24

<210> SEQ ID NO 23
<211> LENGTH: 17
<212> TYPE: DNA
<213> ORGANISM: Artificial Sequence
<220> FEATURE:
<223> OTHER INFORMATION: Gm5077 Reverse Primer Sequence

<400> SEQUENCE: 23
```

```
gcagcgcagc gatactc                                                      17

<210> SEQ ID NO 24
<211> LENGTH: 16
<212> TYPE: DNA
<213> ORGANISM: Artificial Sequence
<220> FEATURE:
<223> OTHER INFORMATION: Gm5077 Reporter 1 Sequence

<400> SEQUENCE: 24
ccgccgtgtt cttcat                                                       16

<210> SEQ ID NO 25
<211> LENGTH: 24
<212> TYPE: DNA
<213> ORGANISM: Artificial Sequence
<220> FEATURE:
<223> OTHER INFORMATION: Plat Forward Primer Sequence

<400> SEQUENCE: 25
agctgacatg ggaatactgt gatg                                              24

<210> SEQ ID NO 26
<211> LENGTH: 25
<212> TYPE: DNA
<213> ORGANISM: Artificial Sequence
<220> FEATURE:
<223> OTHER INFORMATION: Plat Reverse Primer Sequence

<400> SEQUENCE: 26
cctttaattc gaaactgtgg ctgtt                                             25

<210> SEQ ID NO 27
<211> LENGTH: 15
<212> TYPE: DNA
<213> ORGANISM: Artificial Sequence
<220> FEATURE:
<223> OTHER INFORMATION: Plat Reporter 1 Sequence

<400> SEQUENCE: 27
ccgtgctcca cctgc                                                        15

<210> SEQ ID NO 28
<211> LENGTH: 21
<212> TYPE: DNA
<213> ORGANISM: Artificial Sequence
<220> FEATURE:
<223> OTHER INFORMATION: Prss35 Forward Primer Sequence

<400> SEQUENCE: 28
aggagagcac cacacaaaga c                                                 21

<210> SEQ ID NO 29
<211> LENGTH: 20
<212> TYPE: DNA
<213> ORGANISM: Artificial Sequence
<220> FEATURE:
<223> OTHER INFORMATION: Prss35 Reverse Primer Sequence

<400> SEQUENCE: 29
acacgagtcc actggaagga                                                   20

<210> SEQ ID NO 30
<211> LENGTH: 16
<212> TYPE: DNA
```

```
<213> ORGANISM: Artificial Sequence
<220> FEATURE:
<223> OTHER INFORMATION: Prss35 Reporter 1 Sequence

<400> SEQUENCE: 30
ccccggaccc ctcctg                                                    16

<210> SEQ ID NO 31
<211> LENGTH: 345
<212> TYPE: DNA
<213> ORGANISM: Cricetulus griseus

<400> SEQUENCE: 31 tttttttgccc agtcctggtt cttccaaact cacaggtgtc actgaacctc cggggctggg    60
aagctattgt cggggagcgt ctctgagtcc tgaaatatct ttctgtttag aacatgaatg   120
gctttgagga gggtgtggag tttctgcctg tgaataatgc caagaaagtg gagaagcgag   180
gcccccggcg ctgtgtggtg cttgtggtcc tgctggtcag tttcctcttt ctctcactcg   240
tggctggctt cctggtgtgg cacttcctct gtgagtacag tggggctgtg gggagggcga   300
cagaggggta gtgttctctc ttctctcaga ggacagacca aaggg                   345

<210> SEQ ID NO 32
<211> LENGTH: 20
<212> TYPE: DNA
<213> ORGANISM: Artificial Sequence
<220> FEATURE:
<223> OTHER INFORMATION: Forward Primer Sequence

<400> SEQUENCE: 32 tttttttgccc agtcctggtt                                               20

<210> SEQ ID NO 33
<211> LENGTH: 20
<212> TYPE: DNA
<213> ORGANISM: Artificial Sequence
<220> FEATURE:
<223> OTHER INFORMATION: Reverse Primer Sequence

<400> SEQUENCE: 33
ccctttggtc tgtcctctga                                                20

<210> SEQ ID NO 34
<211> LENGTH: 20
<212> TYPE: DNA
<213> ORGANISM: Artificial Sequence
<220> FEATURE:
<223> OTHER INFORMATION: Cut. Primer

<400> SEQUENCE: 34
gtggagtttc tgcctgtgaa                                                20

<210> SEQ ID NO 35
<211> LENGTH: 160
<212> TYPE: DNA
<213> ORGANISM: Cricetulus griseus

<400> SEQUENCE: 35
aacatgaatg gctttgagga gggtgtggag tttctgcctg tgaataatgc caagaaagtg    60
gagaagcgag gcccccggcg ctgtgtggtg cttgtggtcc tgctggtcag tttcctcttt   120
ctctcactcg tggctggctt cctggtgtgg cacttcctct                         160
```

-continued

```
<210> SEQ ID NO 36
<211> LENGTH: 156
<212> TYPE: DNA
<213> ORGANISM: Cricetulus griseus

<400> SEQUENCE: 36
aacatgaatg gctttgagga gggtgtggag ttcctgtgaa taatgccaag aaagtggaga      60
agcgaggccc ccggcgctgt gtggtgcttg tggtcctgct ggtcagtttc ctctttctct     120
cactcgtggc tggcttcctg gtgtggcact tcctct                               156

<210> SEQ ID NO 37
<211> LENGTH: 156
<212> TYPE: DNA
<213> ORGANISM: Cricetulus griseus

<400> SEQUENCE: 37
aacatgaatg gctttgagga gggtgtggag tttctgtgaa taatgccaag aaagtggaga      60
agcgaggccc ccggcgctgt gtggtgcttg tggtcctgct ggtcagtttc ctctttctct     120
cactcgtggc tggcttcctg gtgtggcact tcctct                               156

<210> SEQ ID NO 38
<211> LENGTH: 143
<212> TYPE: DNA
<213> ORGANISM: Cricetulus griseus

<400> SEQUENCE: 38
aacatgaatg gctttgagga gggtgaataa tgccaagaaa gtggagaagc gaggcccccg      60
gcgctgtgtg gtgcttgtgg tcctgctggt cagtttcctc tttctctcac tcgtggctgg     120
cttcctggtg tggcacttcc tct                                             143

<210> SEQ ID NO 39
<211> LENGTH: 17
<212> TYPE: DNA
<213> ORGANISM: Cricetulus griseus

<400> SEQUENCE: 39
tggagtttct gcctgtg                                                     17

<210> SEQ ID NO 40
<211> LENGTH: 146
<212> TYPE: DNA
<213> ORGANISM: Cricetulus griseus

<400> SEQUENCE: 40
aacatgaatg gctttgagga gggtgtggaa taatgccaag aaagtggaga agcgaggccc      60
ccggcgctgt gtggtgcttg tggtcctgct ggtcagtttc ctctttctct cactcgtggc     120
tggcttcctg gtgtggcact tcctct                                          146

<210> SEQ ID NO 41
<211> LENGTH: 14
<212> TYPE: DNA
<213> ORGANISM: Cricetulus griseus

<400> SEQUENCE: 41
gtttctgcct gtga                                                        14

<210> SEQ ID NO 42
<211> LENGTH: 156
<212> TYPE: DNA
```

<213> ORGANISM: Cricetulus griseus

<400> SEQUENCE: 42

| | | | | | |
|---|---|---|---|---|---|
| aacatgaatg | gctttgagga | gggtgtggag | tgcctgtgaa | taatgccaag | aaagtggaga | 60 |
| agcgaggccc | ccggcgctgt | gtggtgcttg | tggtcctgct | ggtcagtttc | ctctttctct | 120 |
| cactcgtggc | tggcttcctg | gtgtggcact | tcctct | | | 156 |

<210> SEQ ID NO 43
<211> LENGTH: 149
<212> TYPE: DNA
<213> ORGANISM: Cricetulus griseus

<400> SEQUENCE: 43

| | | | | | |
|---|---|---|---|---|---|
| aacatgaatg | gctttgagga | gggtgtggag | taataatgcc | aagaaagtgg | agaagcgagg | 60 |
| cccccggcgc | tgtgtggtgc | ttgtggtcct | gctggtcagt | ttcctctttc | tctcactcgt | 120 |
| ggctggcttc | ctggtgtggc | acttcctct | | | | 149 |

<210> SEQ ID NO 44
<211> LENGTH: 11
<212> TYPE: DNA
<213> ORGANISM: Cricetulus griseus

<400> SEQUENCE: 44
ttctgcctgt g         11

<210> SEQ ID NO 45
<211> LENGTH: 153
<212> TYPE: DNA
<213> ORGANISM: Cricetulus griseus

<400> SEQUENCE: 45

| | | | | | |
|---|---|---|---|---|---|
| aacatgaatg | gctttgagga | gggtgtgggc | ctgtgaataa | tgccaagaaa | gtggagaagc | 60 |
| gaggcccccg | gcgctgtgtg | gtgcttgtgg | tcctgctggt | cagtttcctc | tttctctcac | 120 |
| tcgtggctgg | cttcctggtg | tggcacttcc | tct | | | 153 |

<210> SEQ ID NO 46
<211> LENGTH: 145
<212> TYPE: DNA
<213> ORGANISM: Cricetulus griseus

<400> SEQUENCE: 46

| | | | | | |
|---|---|---|---|---|---|
| aacatgaatg | gctttgagga | gggtgtgaat | aatgccaaga | aagtggagaa | gcgaggcccc | 60 |
| cggcgctgtg | tggtgcttgt | ggtcctgctg | gtcagtttcc | tctttctctc | actcgtggct | 120 |
| ggcttcctgg | tgtggcactt | cctct | | | | 145 |

<210> SEQ ID NO 47
<211> LENGTH: 15
<212> TYPE: DNA
<213> ORGANISM: Cricetulus griseus

<400> SEQUENCE: 47
gagtttctgc ctgtg         15

<210> SEQ ID NO 48
<211> LENGTH: 124
<212> TYPE: PRT
<213> ORGANISM: Cricetulus griseus

<400> SEQUENCE: 48

```
Met Gly Ser Asn Arg Gly Arg Lys Ala Gly Gly Ser Ser Lys Asp Phe
1               5                   10                  15

Gly Ala Arg Leu Lys Tyr Ser Ser Gly Leu Glu Asn Met Asn Gly Phe
            20                  25                  30

Glu Glu Gly Val Glu Phe Leu Pro Val Asn Asn Ala Lys Lys Val Glu
        35                  40                  45

Lys Arg Gly Pro Arg Arg Cys Val Val Leu Val Leu Leu Val Ser
    50                  55                  60

Phe Leu Phe Leu Ser Leu Val Ala Gly Phe Leu Val Trp His Phe Leu
65              70                  75                  80

Tyr Ser Asn Val Arg Ile Gln Lys Val Phe Asn Gly His Leu Arg Val
                85                  90                  95

Thr Asn Glu Asn Phe Leu Asp Ala Tyr Glu Asn Ser Asn Ser Thr Glu
            100                 105                 110

Phe Lys Asp Leu Ala Asn Gln Val Lys Glu Ala Leu
            115                 120
```

<210> SEQ ID NO 49
<211> LENGTH: 39
<212> TYPE: PRT
<213> ORGANISM: Cricetulus griseus

<400> SEQUENCE: 49

```
Met Gly Ser Asn Arg Gly Arg Lys Ala Gly Gly Ser Ser Lys Asp Phe
1               5                   10                  15

Gly Ala Arg Leu Lys Tyr Ser Ser Gly Leu Glu Asn Met Asn Gly Phe
            20                  25                  30

Glu Glu Gly Val Glu Phe Leu
        35
```

<210> SEQ ID NO 50
<211> LENGTH: 52
<212> TYPE: PRT
<213> ORGANISM: Cricetulus griseus

<400> SEQUENCE: 50

```
Ile Met Pro Arg Lys Trp Arg Ser Glu Ala Pro Gly Ala Val Trp Cys
1               5                   10                  15

Leu Trp Ser Cys Trp Ser Val Ser Ser Phe Ser His Ser Trp Leu Ala
            20                  25                  30

Ser Trp Cys Gly Thr Ser Ser Thr Gln Met Phe Gly Ser Lys Arg Ser
            35                  40                  45

Ser Met Val Ile
    50
```

<210> SEQ ID NO 51
<211> LENGTH: 25
<212> TYPE: PRT
<213> ORGANISM: Cricetulus griseus

<400> SEQUENCE: 51

```
Gly Ser Gln Met Arg Thr Phe Trp Met Pro Met Arg Thr Gln Thr Pro
1               5                   10                  15

Gln Ser Ser Lys Thr Trp Pro Thr Arg
            20                  25
```

<210> SEQ ID NO 52
<211> LENGTH: 39

```
<212> TYPE: PRT
<213> ORGANISM: Cricetulus griseus

<400> SEQUENCE: 52

Met Gly Ser Asn Arg Gly Arg Lys Ala Gly Gly Ser Ser Lys Asp Phe
1               5                   10                  15

Gly Ala Arg Leu Lys Tyr Ser Ser Gly Leu Glu Asn Met Asn Gly Phe
            20                  25                  30

Glu Glu Gly Val Glu Phe Leu
        35

<210> SEQ ID NO 53
<211> LENGTH: 52
<212> TYPE: PRT
<213> ORGANISM: Cricetulus griseus

<400> SEQUENCE: 53

Ile Met Pro Arg Lys Trp Arg Ser Glu Ala Pro Gly Ala Val Trp Cys
1               5                   10                  15

Leu Trp Ser Cys Trp Ser Val Ser Ser Phe Ser His Ser Trp Leu Ala
            20                  25                  30

Ser Trp Cys Gly Thr Ser Ser Thr Gln Met Phe Gly Ser Lys Arg Ser
        35                  40                  45

Ser Met Val Ile
    50

<210> SEQ ID NO 54
<211> LENGTH: 25
<212> TYPE: PRT
<213> ORGANISM: Cricetulus griseus

<400> SEQUENCE: 54

Gly Ser Gln Met Arg Thr Phe Trp Met Pro Met Arg Thr Gln Thr Pro
1               5                   10                  15

Gln Ser Ser Lys Thr Trp Pro Thr Arg
            20                  25

<210> SEQ ID NO 55
<211> LENGTH: 36
<212> TYPE: PRT
<213> ORGANISM: Cricetulus griseus

<400> SEQUENCE: 55

Met Gly Ser Asn Arg Gly Arg Lys Ala Gly Gly Ser Ser Lys Asp Phe
1               5                   10                  15

Gly Ala Arg Leu Lys Tyr Ser Ser Gly Leu Glu Asn Met Asn Gly Phe
            20                  25                  30

Glu Glu Gly Glu
        35

<210> SEQ ID NO 56
<211> LENGTH: 55
<212> TYPE: PRT
<213> ORGANISM: Cricetulus griseus

<400> SEQUENCE: 56

Cys Gln Glu Ser Gly Glu Ala Arg Pro Pro Ala Leu Cys Gly Ala Cys
1               5                   10                  15

Gly Pro Ala Gly Gln Phe Pro Leu Ser Leu Thr Arg Gly Trp Leu Pro
            20                  25                  30
```

Gly Val Ala Leu Pro Leu Leu Lys Cys Ser Asp Pro Lys Gly Leu Gln
        35                  40                  45

Trp Ser Ser Glu Gly His Lys
    50                  55

<210> SEQ ID NO 57
<211> LENGTH: 6
<212> TYPE: PRT
<213> ORGANISM: Cricetulus griseus

<400> SEQUENCE: 57

Glu Leu Ser Gly Cys Leu
1               5

<210> SEQ ID NO 58
<211> LENGTH: 23
<212> TYPE: PRT
<213> ORGANISM: Cricetulus griseus

<400> SEQUENCE: 58

Glu Leu Lys Leu His Arg Val Gln Arg Pro Gly Gln Pro Gly Glu Gly
1               5                   10                  15

Ser Ala Glu Ala Val Val Gln
            20

<210> SEQ ID NO 59
<211> LENGTH: 37
<212> TYPE: PRT
<213> ORGANISM: Cricetulus griseus

<400> SEQUENCE: 59

Met Gly Ser Asn Arg Gly Arg Lys Ala Gly Gly Ser Ser Lys Asp Phe
1               5                   10                  15

Gly Ala Arg Leu Lys Tyr Ser Ser Gly Leu Glu Asn Met Asn Gly Phe
            20                  25                  30

Glu Glu Gly Val Glu
        35

<210> SEQ ID NO 60
<211> LENGTH: 55
<212> TYPE: PRT
<213> ORGANISM: Cricetulus griseus

<400> SEQUENCE: 60

Cys Gln Glu Ser Gly Glu Ala Arg Pro Pro Ala Leu Cys Gly Ala Cys
1               5                   10                  15

Gly Pro Ala Gly Gln Phe Pro Leu Ser Leu Thr Arg Gly Trp Leu Pro
            20                  25                  30

Gly Val Ala Leu Pro Leu Leu Lys Cys Ser Asp Pro Lys Gly Leu Gln
        35                  40                  45

Trp Ser Ser Glu Gly His Lys
    50                  55

<210> SEQ ID NO 61
<211> LENGTH: 6
<212> TYPE: PRT
<213> ORGANISM: Cricetulus griseus

<400> SEQUENCE: 61

Glu Leu Ser Gly Cys Leu
1               5

```
<210> SEQ ID NO 62
<211> LENGTH: 23
<212> TYPE: PRT
<213> ORGANISM: Cricetulus griseus

<400> SEQUENCE: 62

Glu Leu Lys Leu His Arg Val Gln Arg Pro Gly Gln Pro Gly Glu Gly
1               5                   10                  15

Ser Ala Glu Ala Val Val Gln
            20

<210> SEQ ID NO 63
<211> LENGTH: 39
<212> TYPE: PRT
<213> ORGANISM: Cricetulus griseus

<400> SEQUENCE: 63

Met Gly Ser Asn Arg Gly Arg Lys Ala Gly Gly Ser Ser Lys Asp Phe
1               5                   10                  15

Gly Ala Arg Leu Lys Tyr Ser Ser Gly Leu Glu Asn Met Asn Gly Phe
            20                  25                  30

Glu Glu Gly Val Glu Cys Leu
        35

<210> SEQ ID NO 64
<211> LENGTH: 52
<212> TYPE: PRT
<213> ORGANISM: Cricetulus griseus

<400> SEQUENCE: 64

Ile Met Pro Arg Lys Trp Arg Ser Glu Ala Pro Gly Ala Val Trp Cys
1               5                   10                  15

Leu Trp Ser Cys Trp Ser Val Ser Ser Phe Ser His Ser Trp Leu Ala
            20                  25                  30

Ser Trp Cys Gly Thr Ser Ser Thr Gln Met Phe Gly Ser Lys Arg Ser
            35                  40                  45

Ser Met Val Ile
    50

<210> SEQ ID NO 65
<211> LENGTH: 25
<212> TYPE: PRT
<213> ORGANISM: Cricetulus griseus

<400> SEQUENCE: 65

Gly Ser Gln Met Arg Thr Phe Trp Met Pro Met Arg Thr Gln Thr Pro
1               5                   10                  15

Gln Ser Ser Lys Thr Trp Pro Thr Arg
            20                  25

<210> SEQ ID NO 66
<211> LENGTH: 37
<212> TYPE: PRT
<213> ORGANISM: Cricetulus griseus

<400> SEQUENCE: 66

Met Gly Ser Asn Arg Gly Arg Lys Ala Gly Gly Ser Ser Lys Asp Phe
1               5                   10                  15

Gly Ala Arg Leu Lys Tyr Ser Ser Gly Leu Glu Asn Met Asn Gly Phe
            20                  25                  30
```

```
Glu Glu Gly Val Glu
        35

<210> SEQ ID NO 67
<211> LENGTH: 55
<212> TYPE: PRT
<213> ORGANISM: Cricetulus griseus

<400> SEQUENCE: 67

Cys Gln Glu Ser Gly Glu Ala Arg Pro Pro Ala Leu Cys Gly Ala Cys
1               5                   10                  15

Gly Pro Ala Gly Gln Phe Pro Leu Ser Leu Thr Arg Gly Trp Leu Pro
            20                  25                  30

Gly Val Ala Leu Pro Leu Leu Lys Cys Ser Asp Pro Lys Gly Leu Gln
        35                  40                  45

Trp Ser Ser Glu Gly His Lys
        50                  55

<210> SEQ ID NO 68
<211> LENGTH: 6
<212> TYPE: PRT
<213> ORGANISM: Cricetulus griseus

<400> SEQUENCE: 68

Glu Leu Ser Gly Cys Leu
1               5

<210> SEQ ID NO 69
<211> LENGTH: 23
<212> TYPE: PRT
<213> ORGANISM: Cricetulus griseus

<400> SEQUENCE: 69

Glu Leu Lys Leu His Arg Val Gln Arg Pro Gly Gln Pro Gly Glu Gly
1               5                   10                  15

Ser Ala Glu Ala Val Val Gln
            20
```